(12) United States Patent
Fetner et al.

(10) Patent No.: US 7,837,832 B2
(45) Date of Patent: *Nov. 23, 2010

(54) ADDITIVE COMPOSITIONS FOR TREATING VARIOUS BASE SHEETS

(75) Inventors: Christopher B. Fetner, Neenah, WI (US); Thomas J. Dyer, Neenah, WI (US); Michael R. Lostocco, Appleton, WI (US); Deborah J. Nickel, Appleton, WI (US); Troy M. Runge, Neenah, WI (US); Kenneth J. Zwick, Neenah, WI (US); Mike T. Goulet, Neenah, WI (US); Jeffrey J. Timm, Menasha, WI (US); Perry H. Clough, Neenah, WI (US); Michael J. Rekoske, Appleton, WI (US)

(73) Assignee: Dow Global Technologies, Inc., Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/763,262

(22) Filed: Jun. 14, 2007

(65) Prior Publication Data

US 2007/0295464 A1 Dec. 27, 2007

Related U.S. Application Data

(63) Continuation-in-part of application No. 11/303,002, filed on Dec. 15, 2005, and a continuation-in-part of application No. 11/304,490, filed on Dec. 15, 2005, and a continuation-in-part of application No. 11/303,036, filed on Dec. 15, 2005, and a continuation-in-part of application No. 11/304,998, filed on Dec. 15, 2005, and a continuation-in-part of application No. 11/304,063, filed on Dec. 15, 2005, and a continuation-in-part of application No. 11/635,385, filed on Dec. 7, 2006.

(51) Int. Cl.
*D21H 17/34* (2006.01)
*D21H 19/20* (2006.01)
*D21H 21/18* (2006.01)

(52) U.S. Cl. ............. 162/168.1; 162/112; 162/123; 162/135; 162/158; 162/164.1; 162/184

(58) Field of Classification Search ............. 162/112, 162/123, 135, 158, 164.1, 168.1, 184
See application file for complete search history.

(56) References Cited

U.S. PATENT DOCUMENTS 3,879,257 A * 4/1975 Gentile et al. ............. 162/112

(Continued)

*Primary Examiner*—Matthew J. Daniels
*Assistant Examiner*—Dennis Cordray

(57) ABSTRACT

Wiping products are disclosed comprising a sheet and an additive composition. The additive composition, for instance, comprises an aqueous dispersion containing an alpha-olefin polymer, an ethylene-carboxylic acid copolymer, or mixtures thereof. The alpha-olefin polymer may comprise an interpolymer of ethylene and octene, while the ethylene-carboxylic acid copolymer may comprise ethylene-acrylic acid copolymer. The additive composition may also contain a dispersing agent, such as a fatty acid. The additive composition may be incorporated into the sheet by being combined with the fibers that are used to form the sheet. Alternatively, the additive composition may be topically applied to the sheet after the sheet has been formed. For instance, in one embodiment, the additive composition may be applied to the sheet as a creping adhesive during a creping operation. The additive composition may improve the strength of the sheet and/or improve the perceived softness of the sheet.

22 Claims, 32 Drawing Sheets

U.S. PATENT DOCUMENTS

| | | | |
|---|---|---|---|
| 2004/0099388 A1* | 5/2004 | Chen et al. | 162/134 |
| 2004/0118532 A1* | 6/2004 | Sarbo et al. | 162/109 |
| 2005/0045292 A1* | 3/2005 | Lindsay et al. | 162/109 |
| 2005/0100754 A1* | 5/2005 | Moncla et al. | 428/523 |

* cited by examiner

Control Sample at 500x magnification.

6.8% by weight of the additive composition at 500x magnification.

13% by weight of the additive composition at 500x magnification.

SEM surface image, magnification = 15X

SEM surface image, magnification = 30X

SEM surface image, magnification = 15X

SEM surface image, magnification = 30X

SEM surface image, magnification = 150X

SEM surface image, magnification = 750X

ADDITIVE COMPOSITIONS FOR TREATING VARIOUS BASE SHEETS

RELATED APPLICATIONS

The present application claims priority to and is a continuation-in-part application of U.S. Ser. No. 11/303,002 filed on Dec. 15, 2005, U.S. Ser. No. 11/304,490 filed on Dec. 15, 2005, U.S. Ser. No. 11/303,036 filed on Dec. 15, 2005, U.S. Ser. No. 11/304,998 filed on Dec. 15, 2005, U.S. Ser. No. 11/304,063 filed on Dec. 15, 2005 and U.S. Ser. No. 11/635,385 filed on Dec. 7, 2006.

FIELD OF INVENTION

The instant invention relates to additive compositions for treating various base sheets.

BACKGROUND

Absorbent tissue products such as paper towels, facial tissues, bath tissues and other similar products are designed to include several important properties. For example, the products should have good bulk, a soft feel and should be highly absorbent. The product should also have good strength and resist tearing, even while wet. Unfortunately, it is very difficult to produce a high strength tissue product that is also soft and highly absorbent. Usually, when steps are taken to increase one property of the product, other characteristics of the product are adversely affected.

For instance, softness is typically increased by decreasing or reducing cellulosic fiber bonding within the tissue product. Inhibiting or reducing fiber bonding, however, adversely affects the strength of the base web.

In other embodiments, softness is enhanced by the topical addition of a softening agent to the outer surfaces of the base web. The softening agent may comprise, for instance, a silicone. The silicone may be applied to the web by printing, coating or spraying. Although silicones make the base webs feel softer, silicones can be relatively expensive and may lower sheet durability as measured by tensile strength and/or tensile energy absorbed.

In order to improve durability, in the past, various strength agents have been added to tissue products. The strength agents may be added to increase the dry strength of the base web or the wet strength of the base web. Some strength agents are considered temporary, since they only maintain wet strength in the tissue for a specific length of time. Temporary wet strength agents, for instance, may add strength to bath tissues during use while not preventing the bath tissues from disintegrating when dropped in a commode and flushed into a sewer line or septic tank.

Bonding agents have also been topically applied to tissue products alone or in combination with creping operations. For example, one particular process that has proved to be very successful in producing paper towels and wipers is disclosed in U.S. Pat. No. 3,879,257 to Gentile, et al., which is incorporated herein by reference in its entirety. In Gentile, et al., a process is disclosed in which a bonding material is applied in a fine, defined pattern to one side of a fibrous web. The web is then adhered to a heated creping surface and creped from the surface. A bonding material is applied to the opposite side of the web and the web is similarly creped. The process disclosed in Gentile, et al. produces wiper products having exceptional bulk, outstanding softness and good absorbency. The surface regions of the web also provide excellent strength, abrasion resistance, and wipe-dry properties.

Although the process and products disclosed in Gentile, et al. have provided many advances in the art of making paper wiping products, further improvements in various aspects of paper wiping products remain desired. For example, particular strength agents are still needed that can be incorporated into base webs without significantly adversely impacting the softness of the webs. A need also exists for a strength agent that can be incorporated into the web at any point during its production. For instance, a need exists for a strength agent that can be added to a pulpsheet prior to slurry formation, an aqueous suspension of fibers used to form a base web, a formed base web prior to drying, and/or to a base web that has been dried.

Furthermore, in the past, additive compositions topically applied to base webs had a tendency, under some circumstances, to create blocking problems, which refers to the tendency of two adjacent tissue sheets to stick together. As such, a need also exists for an additive composition or strength agent that is topically applied to a base web without creating blocking problems.

SUMMARY

In general, the present disclosure is directed to wet and dry wiping products having improved properties due to the presence of an additive composition. The wiping product may comprise, for instance, a bath tissue, a facial tissue, a paper towel, an industrial wiper, a premoistened wiper and the like. The product may contain one ply or may contain multiple plies. The additive composition can be incorporated into the wiping product in order to improve the strength of the product without significantly affecting the softness and/or blocking behavior of the product in a negative manner. In fact, the additive composition may actually improve softness in conjunction with improving strength. The additive composition can also increase strength without associated problems with blocking. The additive composition may comprise, for instance, an aqueous dispersion containing a thermoplastic resin. In one embodiment, the additive composition is applied topically to a web such as during a creping operation.

The additive composition may comprise a non-fibrous olefin polymer. The additive composition, for instance, may comprise a film-forming composition and the olefin polymer may comprise an interpolymer of ethylene and at least one comonomer comprising an alkene, such as 1-octene. The additive composition may also contain a dispersing agent, such as a carboxylic acid. Examples of particular dispersing agents, for instance, include fatty acids, such as oleic acid or stearic acid.

In one particular embodiment, the additive composition may contain an ethylene and octene copolymer in combination with an ethylene-acrylic acid copolymer. The ethylene-acrylic acid copolymer is not only a thermoplastic resin, but may also serve as a dispersing agent. The ethylene and octene copolymer may be present in combination with the ethylene-acrylic acid copolymer in a weight ratio of from about 1:10 to about 10:1, such as from about 2:3 to about 3:2.

The olefin polymer composition may exhibit a crystallinity of less than about 50%, such as less than about 20%. The olefin polymer may also have a melt index of less than about 1000 g/10 min, such as less than about 700 g/10 min. The olefin polymer may also have a relatively small particle size, such as from about 0.1 micron to about 5 microns when contained in an aqueous dispersion.

In an alternative embodiment, the additive composition may contain an ethylene-acrylic acid copolymer. The ethylene-acrylic acid copolymer may be present in the additive composition in combination with a dispersing agent, such as a fatty acid.

In one embodiment, the additive composition can be topically applied to one or both sides of a base web. Once applied to a base web, it has been discovered that the additive composition may form a discontinuous but interconnected film depending upon the amount applied to the web. In this manner, the additive composition increases the strength of the web without significantly interfering with the ability of the web to absorb fluids. For example, the discontinuous film that is formed includes openings that allow liquids to be absorbed by the base web.

In other embodiments, the additive composition may be applied to a base web in relatively light amounts such that the additive composition forms discrete treated areas on the surface of the web. Even at such low amounts, however, the additive composition can still enhance one or more properties of the web.

Also of advantage, the additive composition does not substantially penetrate into the base web when applied. For instance, the additive composition penetrates the base web in an amount less than about 30% of the thickness of the web, such as less than about 20%, such as less than about 10% of the thickness of the web. By remaining primarily on the surface of the web, the additive composition does not interfere with the liquid absorption capacity properties of the web. Further, the additive composition does not substantially increase the stiffness of the web and, as described above, without creating problems with blocking.

In one embodiment, the additive composition may be applied to one side of a base web for adhering the base web to a creping drum and for creping the base web from the drum surface. In this embodiment, for instance, the additive composition may be applied to one side of the base web according to a pattern. The pattern may comprise, for instance, a pattern of discrete shapes, a reticulated pattern, or a combination of both. In order to apply the additive composition to the base web, the additive composition may be printed onto the base web according to the pattern. For instance, in one embodiment, a rotogravure printer may be used.

The additive composition may be applied to one side of the base web in an amount from about 0.1% to about 30% by weight. In some embodiments, after the additive composition is applied to the web, the web can be dried at a temperature in the range of equal to or greater than the melting point temperature of the base polymer in the additive composition. Once applied, the additive composition stays substantially on the surface of the base web for increasing strength without interfering with the absorption properties of the web. For instance, when applied to the base web, the additive composition may penetrate the base web less than about 10% of the thickness of the base web, such as less than about 5% of the thickness of the web. The additive composition may form a discontinuous film on the surface of the base web for providing strength while also providing untreated areas where liquids may be quickly absorbed by the web.

When the base web is adhered to the creping drum, if desired, the creping drum may be heated. For instance, the creping surface may be heated to a temperature of from about 80° C. to about 200° C., such as from about 100° C. to about 150° C. The additive composition may be applied only to a single side of the base web or may be applied to both sides of the web according to the same or different patterns. When applied to both sides of the web, both sides of the web may be creped from a creping drum or only one side of the web may be creped.

The base web treated with the additive composition may, in one embodiment, comprise an uncreped through-air dried web prior to applying the additive composition. Once creped from the creping surface, the web may have a a bulk in the range of greater than 3 cc/g, such as greater than about 10 cc/g. In the alternative, once creped from creping surface, the web may have a bulk in the range of less 3 cc/g. The wiping product may be used as a single ply product or may be incorporated into a multiple ply product.

As described above, the additive composition may improve various properties of the base sheet. For instance, the additive composition provides the base sheet with a lotiony and soft feel. One test that measures one aspect of softness is called the Stick-Slip Test. During the Stick-Slip Test, a sled is pulled over a surface of the base sheet while the resistive force is measured. A higher stick-slip number indicates a more lotiony surface with lower drag forces. Base webs treated in accordance with the present disclosure, for instance, can have a stick-slip on one side of greater than about −0.01, such as from about −0.006 to about 0.7, such as from about 0 to about 0.7.

In addition, the properties of the base sheet are improved without creating any significant blocking problems. For instance, wiping products treated in accordance with the present disclosure when stacked together can have a sheet blocking of less than 15 gf, such as less than about 10 gf. For example, in certain embodiments, stacked products can have a sheet blocking of less than about 5 gf, such as even less than about 2 gf.

The base sheets treated in accordance with the present disclosure can be made entirely from natural or synthetic cellulosic fibers, such as pulp fibers, or can be made from a mixture of fibers. For instance, the base sheets can comprise cellulosic fibers in combination with synthetic fibers. The base sheet may, for example, comprise less than 50 percent by weight of cellulosic fibers based on the weight of the base sheet; for example, the base sheet may comprise 0 to 49 percent by weight of cellulosic fibers based on the weight of the sheet. In the alternative, a portion of the fibers, such as greater than 50 percent by dry weight, or from 55 to 99 percent by dry weight, can be synthetic fibers such as rayon, polyolefin fibers, polyester fibers, bicomponent sheath-core fibers, multi-component binder fibers, and the like. In the alternative, the base sheet can be made entirely from synthetic fibers such as rayon, polyolefin fibers, polyester fibers, bicomponent sheath-core fibers, multi-component binder fibers, and the like.

Base sheets that may be treated in accordance with the present disclosure include wet-laid base webs. In other embodiments, however, the base sheet may comprise an air-laid web, a hydroentangled web, a coform web, and the like. In another alternative, the base sheet may be a non-woven material, a woven material, or a knitted material.

Other features and aspects of the present invention are discussed in greater detail below.

BRIEF DESCRIPTION OF THE DRAWINGS

For the purpose of illustrating the instant invention, there is shown in the drawings a form that is presently preferred; it being understood, however, that this invention is not limited to the precise arrangements and instrumentalities shown.

Figure 1:
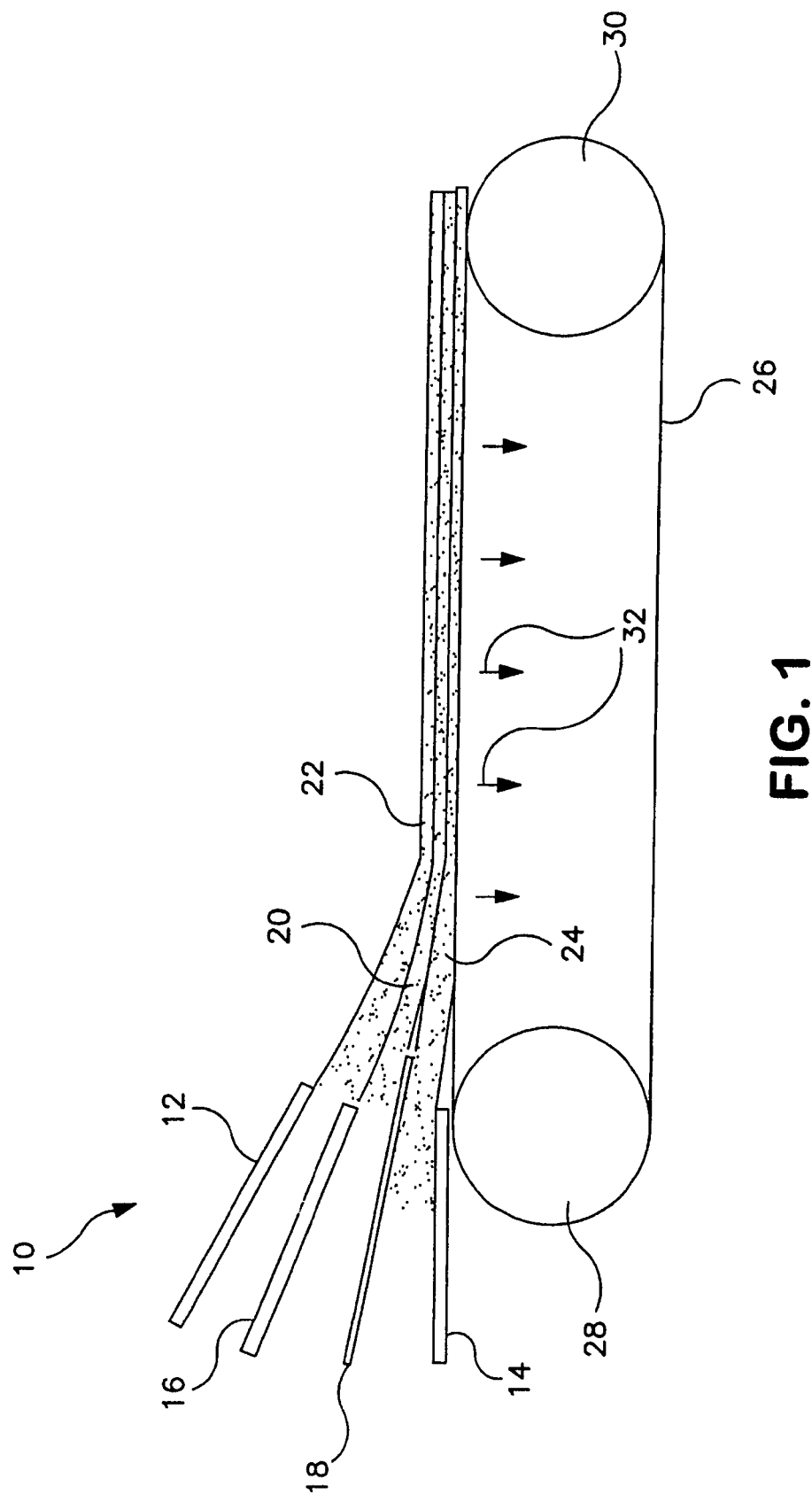
FIG. 1 is a schematic diagram of a base web forming machine, illustrating the formation of a stratified base web having multiple layers in accordance with the present disclosure.

Repeat use of reference characters in the present specification and drawings is intended to represent same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to the incorporation of an additive composition into a wiping product, such as a base web, in order to improve the strength of the web. The strength of the web can be increased without significantly adversely affecting the perceived softness properties of the web. In fact, the softness can be increased in some applications. The additive composition may comprise a polyolefin dispersion. For example, the polyolefin dispersion may contain polymeric particles having a relatively small size, such as less than about 5 microns, in an aqueous medium when applied or incorporated into a base web. Once dried, however, the polymeric particles are generally indistinguishable. For example, in one embodiment, the additive composition may comprise a film-forming composition that forms a discontinuous film and/or forms discrete treated areas on the base sheet. In some embodiments, the polyolefin dispersion may also contain a dispersing agent.

As will be described in greater detail below, the additive composition can be incorporated into a base web using various techniques and during different stages of production of the tissue product. For example, in one embodiment, the additive composition can be combined with an aqueous suspension of fibers that is used to form the base web. In an alternative embodiment, the additive composition can be applied to a dry pulp sheet that is used to form an aqueous suspension of fibers.

In still another embodiment, the additive composition may be topically applied to the base web while the base web is wet or after the base web has been dried. For instance, in one embodiment, the additive composition may be applied topically to the base web. For example, the additive composition may be applied to a base web during a creping operation. In particular, the additive composition has been found well-suited for adhering a base web to a creping surface during a creping process.

The use of the additive composition containing a polyolefin dispersion has been found to provide various benefits and advantages depending upon the particular embodiment. For example, the additive composition has been found to improve the geometric mean tensile strength and the geometric mean tensile energy absorbed of treated base webs in comparison to untreated webs. Further, the above strength properties may be improved without significantly adversely impacting the stiffness of the base webs in relation to untreated webs and in relation to base webs treated with a silicone composition, as has been commonly done in the past. Thus, base webs made according to the present disclosure may have a perceived softness that is similar to or equivalent with base webs treated with a silicone composition. Base webs made according to the present disclosure, however, may have significantly improved strength properties at the same perceived softness levels.

The increase in strength properties is also comparable to prior art base webs treated with a bonding material, such as an ethylene-vinyl acetate copolymer. Problems with sheet blocking, however, which is the tendency of adjacent sheets to stick together, is significantly reduced when base webs are made in accordance with the present disclosure as compared to those treated with an ethylene-vinyl acetate copolymer additive composition, as has been done in the past.

The above advantages and benefits may be obtained by incorporating the additive composition into the base web at virtually any point during the manufacture of the web. The additive composition generally contains an aqueous dispersion comprising at least one thermoplastic resin, water, and, optionally, at least one dispersing agent. The thermoplastic resin is present within the dispersion at a relatively small particle size. For example, the average volumetric particle size of the polymer may be less than about 5 microns. The actual particle size may depend upon various factors including the thermoplastic polymer that is present in the dispersion. Thus, the average volumetric particle size may be from about 0.05 microns to about 5 microns, such as less than about 4 microns, such as less than about 3 microns, such as less than about 2 microns, such as less than about 1 micron. Particle sizes can be measured on a Coulter LS230 light-scattering particle size analyzer or other suitable device. When present in the aqueous dispersion and when present in the base web, the thermoplastic resin is typically found in a non-fibrous form.

The particle size distribution of the polymer particles in the dispersion may be less than or equal to about 2.0, such as less than 1.9, 1.7 or 1.5.

Examples of aqueous dispersions that may be incorporated into the additive composition of the present disclosure are disclosed, for instance, in U.S. Patent Application Publication No. 2005/0100754, U.S. Patent Application Publication No. 2005/0192365, PCT Publication No. WO 2005/021638, and PCT Publication No. WO 2005/021622, which are all incorporated herein by reference.

In one embodiment, the additive composition may comprise a film forming composition capable of forming a film on the surface of a base web. For instance, when topically applied to a base web, the additive composition can form a discontinuous but interconnected film. In other words, the additive composition forms an interconnected polymer network over the surface of the base web. The film or polymer network, however, is discontinuous in that various openings are contained within the film. The size of the openings can vary depending upon the amount of additive composition that is applied to the web and the manner in which the additive composition is applied. Of particular advantage, the openings allow liquids to be absorbed through the discontinuous film and into the interior of the base web. In this regard, the wicking properties of the base web are not substantially affected by the presence of the additive composition.

In other embodiments, when the additive composition is added in relatively small amounts to the base web, the additive composition does not form an interconnected network but, instead, appears on the base sheet as treated discrete areas. Even at relatively low amounts, however, the additive composition can still enhance at least one property of the base sheet. For instance, the feel of the base sheet can be improved even in amounts less than about 2.5% by weight, such as less than 2% by weight, such as less than 1.5% by weight, such as less than 1% by weight, such as even less than 0.5% by weight.

Further, in some embodiments, the additive composition remains primarily on the surface of the base web and does not penetrate the web once applied. In this manner, not only does the discontinuous film allow the base web to absorb fluids that contact the surface but also does not significantly interfere with the ability of the base web to absorb relatively large amounts of fluid. Thus, the additive composition does not significantly interfere with the liquid absorption properties of the web while increasing the strength of the web without substantially impacting adversely on the stiffness of the web.

The thickness of the additive composition when present on the surface of a base sheet can vary depending upon the ingredients of the additive composition and the amount applied. In general, for instance, the thickness can vary from about 0.01 microns to about 10 microns. At higher add-on levels, for instance, the thickness may be from about 3 microns to about 8 microns. At lower add-on levels, however, the thickness may be from about 0.1 microns to about 1 micron, such as from about 0.3 microns to about 0.7 microns.

At relatively low add-on levels, the additive composition may also deposit differently on the base sheet than when at relatively high add-on levels. For example, at relatively low add-on levels, not only do discrete treated areas form on the base sheet, but the additive composition may better follow the topography of the base sheet. For instance, in one embodiment, it has been discovered that the additive composition follows the crepe pattern of a base sheet when the base sheet is creped.

The thermoplastic resin contained within the additive composition may vary depending upon the particular application and the desired result. In one embodiment, for instance, thermoplastic resin is an olefin polymer. As used herein, an olefin polymer refers to a class of unsaturated open-chain hydrocarbons having the general formula $C_nH_{2n}$. The olefin polymer may be present as a copolymer, such as an interpolymer. As used herein, a substantially olefin polymer refers to a polymer that contains less than about 1% substitution.

In one particular embodiment, for instance, the olefin polymer may comprise an alpha-olefin interpolymer of ethylene with at least one comonomer selected from the group consisting of a $C_4$-$C_{20}$ linear, branched or cyclic diene, or an ethylene vinyl compound, such as vinyl acetate, and a compound represented by the formula $H_2C=CHR$ wherein R is a $C_1$-$C_{20}$ linear, branched or cyclic alkyl group or a $C_6$-$C_{20}$ aryl group. Examples of comonomers include propylene, 1-butene, 3-methyl-1-butene, 4-methyl-1-pentene, 3-methyl-1-pentene, 1-heptene, 1-hexene, 1-octene, 1-decene, and 1-dodecene. In some embodiments, the interpolymer of ethylene has a density of less than about 0.92 g/cc.

In other embodiments, the thermoplastic resin comprises an alpha-olefin interpolymer of propylene with at least one comonomer selected from the group consisting of ethylene, a $C_4$-$C_{20}$ linear, branched or cyclic diene, and a compound represented by the formula $H_2C=CHR$ wherein R is a $C_1$-$C_{20}$ linear, branched or cyclic alkyl group or a $C_6$-$C_{20}$ aryl group. Examples of comonomers include ethylene, 1-butene, 3-methyl-1-butene, 4-methyl-1-pentene, 3-methyl-1-pentene, 1-heptene, 1-hexene, 1-octene, 1-decene, and 1-dodecene. In some embodiments, the comonomer is present at about 5% by weight to about 25% by weight of the interpolymer. In one embodiment, a propylene-ethylene interpolymer is used.

Other examples of thermoplastic resins which may be used in the present disclosure include homopolymers and copolymers (including elastomers) of an olefin such as ethylene, propylene, 1-butene, 3-methyl-1-butene, 4-methyl-1-pentene, 3-methyl-1-pentene, 1-heptene, 1-hexene, 1-octene, 1-decene, and 1-dodecene as typically represented by polyethylene, polypropylene, poly-1-butene, poly-3-methyl-1-butene, poly-3-methyl-1-pentene, poly-4-methyl-1-pentene, ethylene-propylene copolymer, ethylene-1-butene copolymer, and propylene-1-butene copolymer; copolymers (including elastomers) of an alpha-olefin with a conjugated or non-conjugated diene as typically represented by ethylene-butadiene copolymer and ethylene-ethylidene norbornene copolymer; and polyolefins (including elastomers) such as copolymers of two or more alpha-olefins with a conjugated or non-conjugated diene as typically represented by ethylene-propylene-butadiene copolymer, ethylene-propylene-dicyclopentadiene copolymer, ethylene-propylene-1,5-hexadiene copolymer, and ethylene-propylene-ethylidene norbornene copolymer; ethylene-vinyl compound copolymers such as ethylene-vinyl acetate copolymers with N-methylol functional comonomers, ethylene-vinyl alcohol copolymers with N-methylol functional comonomers, ethylene-vinyl chloride copolymer, ethylene acrylic acid or ethylene-(meth)acrylic acid copolymers, and ethylene-(meth)acrylate copolymer; styrenic copolymers (including elastomers) such as polystyrene, ABS, acrylonitrile-styrene copolymer, methylstyrene-styrene copolymer; and styrene block copolymers (including elastomers) such as styrene-butadiene copolymer and hydrate thereof, and styrene-isoprene-styrene triblock copolymer; polyvinyl compounds such as polyvinyl chloride, polyvinylidene chloride, vinyl chloride-vinylidene chloride copolymer, polymethyl acrylate, and polymethyl methacrylate; polyamides such as nylon 6, nylon 6,6, and nylon 12; thermoplastic polyesters such as polyethylene terephthalate and polybutylene terephthalate; polycarbonate, polyphenylene oxide, and the like. These resins may be used either alone or in combinations of two or more.

In particular embodiments, polyolefins such as polypropylene, polyethylene, and copolymers thereof and blends thereof, as well as ethylene-propylene-diene terpolymers are used. In some embodiments, the olefinic polymers include homogeneous polymers described in U.S. Pat. No. 3,645,992 by Elston; high density polyethylene (HDPE) as described in U.S. Pat. No. 4,076,698 to Anderson; heterogeneously branched linear low density polyethylene (LLDPE); heterogeneously branched ultra low linear density (ULDPE); homogeneously branched, linear ethylene/alpha-olefin copolymers; homogeneously branched, substantially linear ethylene/alpha-olefin polymers which can be prepared, for example, by a process disclosed in U.S. Pat. Nos. 5,272,236 and 5,278,272, the disclosure of which process is incorporated herein by reference; and high pressure, free radical polymerized ethylene polymers and copolymers such as low density polyethylene (LDPE). In still another embodiment of the present invention, the thermoplastic resin comprises an ethylene-carboxylic acid copolymer, such as ethylene-acrylic acid (EAA) and ethylene-methacrylic acid copolymers such as for example those available under the tradenames PRIMACOR™ from The Dow Chemical Company, NUCREL™ from DuPont, and ESCOR™ from ExxonMobil, and described in U.S. Pat. Nos. 4,599,392, 4,988,781, and 5,384,373, each of which is incorporated herein by reference in its entirety, and ethylene-vinyl acetate (EVA) copolymers. Polymer compositions described in U.S. Pat. Nos. 6,538,070, 6,566,446, 5,869,575, 6,448,341, 5,677,383, 6,316,549, 6,111,023, or 5,844,045, each of which is incorporated herein by reference in its entirety, are also suitable in some embodiments. Of course, blends of polymers can be used as well. In some embodiments, the blends include two different Ziegler-Natta polymers. In other embodiments, the blends can include blends of a Ziegler-Natta and a metallocene polymer. In still other embodiments, the thermoplastic resin used herein is a blend of two different metallocene polymers.

In one particular embodiment, the thermoplastic resin comprises an alpha-olefin interpolymer of ethylene with a comonomer comprising an alkene, such as 1-octene. The ethylene and octene copolymer may be present alone in the additive composition or in combination with another thermoplastic resin, such as ethylene-acrylic acid copolymer. Of particular advantage, the ethylene-acrylic acid copolymer not only is a thermoplastic resin, but also serves as a dispersing agent. For some embodiments, the additive composition should comprise a film-forming composition. It has been found that the ethylene-acrylic acid copolymer may assist in forming films, while the ethylene and octene copolymer lowers the stiffness. When applied to a base web, the composition may or may not form a film within the product, depending upon how the composition is applied and the amount of the composition that is applied. When forming a film on the base web, the film may be continuous or discontinuous. When present together, the weight ratio between the ethylene and octene copolymer and the ethylene-acrylic acid copolymer may be from about 1:10 to about 10:1, such as from about 3:2 to about 2:3.

The thermoplastic resin, such as the ethylene and octene copolymer, may have a crystallinity of less than about 50%, such as less than about 25%. The polymer may have been produced using a single site catalyst and may have a weight average molecular weight of from about 15,000 to about 5 million, such as from about 20,000 to about 1 million. The molecular weight distribution of the polymer may be from about 1.01 to about 40, such as from about 1.5 to about 20, such as from about 1.8 to about 10.

Depending upon the thermoplastic polymer, the melt index of the polymer may range from about 0.001 g/10 min to about 1,000 g/10 min, such as from about 0.5 g/10 min to about 800 g/10 min. For example, in one embodiment, the melt index of the thermoplastic resin may be from about 100 g/10 min to about 700 g/10 min.

The thermoplastic resin may also have a relatively low melting point. For instance, the melting point of the thermoplastic resin may be less than about 140° C., such as less than 130° C., such as less than 120° C. For instance, in one embodiment, the melting point may be less than about 90° C. The glass transition temperature of the thermoplastic resin may also be relatively low. For instance, the glass transition temperature may be less than about 50° C., such as less than about 40° C.

The one or more thermoplastic resins may be contained within the additive composition in an amount from about 1% by weight to about 96% by weight. For instance, the thermoplastic resin may be present in the aqueous dispersion in an amount from about 10% by weight to about 70% by weight, such as from about 20% to about 50% by weight.

In addition to at least one thermoplastic resin, the aqueous dispersion may also contain a dispersing agent. A dispersing agent is an agent that aids in the formation and/or the stabilization of the dispersion. One or more dispersing agents may be incorporated into the additive composition.

In general, any suitable dispersing agent can be used. In one embodiment, for instance, the dispersing agent comprises at least one carboxylic acid, a salt of at least one carboxylic acid, or carboxylic acid ester or salt of the carboxylic acid ester. Examples of carboxylic acids useful as a dispersant comprise fatty acids such as montanic acid, stearic acid, oleic acid, and the like. In some embodiments, the carboxylic acid, the salt of the carboxylic acid, or at least one carboxylic acid fragment of the carboxylic acid ester or at least one carboxylic acid fragment of the salt of the carboxylic acid ester has fewer than 25 carbon atoms. In other embodiments, the carboxylic acid, the salt of the carboxylic acid, or at least one carboxylic acid fragment of the carboxylic acid ester or at least one carboxylic acid fragment of the salt of the carboxylic acid ester has 12 to 25 carbon atoms. In some embodiments, carboxylic acids, salts of the carboxylic acid, at least one carboxylic acid fragment of the carboxylic acid ester or its salt has 15 to 25 carbon atoms are preferred. In other embodiments, the number of carbon atoms is 25 to 60. Some examples of salts comprise a cation selected from the group consisting of an alkali metal cation, alkaline earth metal cation, or ammonium or alkyl ammonium cation.

In still other embodiments, the dispersing agent is selected from the group consisting of ethylene-carboxylic acid polymers, and their salts, such as ethylene-acrylic acid copolymers or ethylene-methacrylic acid copolymers.

In other embodiments, the dispersing agent is selected from alkyl ether carboxylates, petroleum sulfonates, sulfonated polyoxyethylenated alcohol, sulfated or phosphated polyoxyethylenated alcohols, polymeric ethylene oxide/propylene oxide/ethylene oxide dispersing agents, primary and secondary alcohol ethoxylates, alkyl glycosides and alkyl glycerides.

When ethylene-acrylic acid copolymer is used as a dispersing agent, the copolymer may also serve as a thermoplastic resin.

In one particular embodiment, the aqueous dispersion contains an ethylene and octene copolymer, ethylene-acrylic acid copolymer, and a fatty acid, such as stearic acid or oleic acid. The dispersing agent, such as the carboxylic acid, may be present in the aqueous dispersion in an amount from about 0.1% to about 10% by weight.

In addition to the above components, the aqueous dispersion also contains water. Water may be added as deionized water, if desired. The pH of the aqueous dispersion is generally less than about 12, such as from about 5 to about 11.5, such as from about 7 to about 11. The aqueous dispersion may have a solids content of less than about 75%, such as less than about 70%. For instance, the solids content of the aqueous dispersion may range from about 5% to about 60%. In general, the solids content can be varied depending upon the manner in which the additive composition is applied or incorporated into the base web. For instance, when incorporated into the base web during formation, such as by being added with an aqueous suspension of fibers, a relatively high solids content can be used. When topically applied such as by spraying or printing, however, a lower solids content may be used in order to improve processability through the spray or printing device.

While any method may be used to produce the aqueous dispersion, in one embodiment, the dispersion may be formed through a melt-kneading process. For example, the kneader may comprise a Banbury mixer, single-screw extruder or a multi-screw extruder. The melt-kneading may be conducted under the conditions which are typically used for melt-kneading the one or more thermoplastic resins.

In one particular embodiment, the process includes melt-kneading the components that make up the dispersion. The melt-kneading machine may include multiple inlets for the various components. For example, the extruder may include four inlets placed in series. Further, if desired, a vacuum vent may be added at an optional position of the extruder.

In some embodiments, the dispersion is first diluted to contain about 1 to about 3% by weight water and then, subsequently, further diluted to comprise greater than about 25% by weight water.

When treating base webs in accordance with the present disclosure, the additive composition containing the aqueous polymer dispersion can be applied to the base web topically or can be incorporated into the base web by being pre-mixed with the fibers that are used to form the web. When applied topically, the additive composition can be applied to the base web when wet or dry. In one embodiment, the additive composition may be applied topically to the web during a creping process. For instance, in one embodiment, the additive composition may be sprayed onto the web or onto a heated dryer drum in order to adhere the web to the dryer drum. The web can then be creped from the dryer drum. When the additive composition is applied to the web and then adhered to the dryer drum, the composition may be uniformly applied over the surface area of the web or may be applied according to a particular pattern.

When topically applied to a base web, the additive composition may be sprayed onto the web, extruded onto the web, or printed onto the web. When extruded onto the web, any suitable extrusion device may be used, such as a slot-coat extruder or a meltblown dye extruder. When printed onto the web, any suitable printing device may be used. For example, an inkjet printer or a rotogravure printing device may be used.

In one embodiment, the additive composition may be heated prior to or during application to a base web. Heating the composition can lower the viscosity for facilitating application. For instance, the additive composition may be heated to a temperature of from about 50° C. to about 150° C.

Wiping products made according to the present disclosure may include single-ply tissue products or multiple-ply tissue products. For instance, in one embodiment, the product may include two plies or three plies.

In general, any suitable base web may be treated in accordance with the present disclosure. For example, in one embodiment, the base sheet can be a tissue product, such as a bath tissue, a facial tissue, a paper towel, an industrial wiper, and the like. Such tissue products may have a bulk density in the range of less than 3 cc/g; or in the alternative, such tissue products may have a bulk of at least 3 cc/g. The tissue products can contain one or more plies and can be made from any suitable types of fiber.

Fibers suitable for making base webs comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628 issued Jan. 21, 1997, to Gordon et al.

The base sheet may, for example, comprise less than 50 percent by weight of cellulosic fibers based on the weight of the base sheet; for example, the base sheet may comprise 0 to 49 percent by weight of cellulosic fibers based on the weight of the sheet. In the alternative, a portion of the fibers, such as greater than 50 percent by dry weight, or from 55 to 99 percent by dry weight, can be synthetic fibers such as rayon, polyolefin fibers, polyester fibers, bicomponent sheath-core fibers, multi-component binder fibers, and the like. In alternative, the base sheet may comprise entirely from a non-cellulosic material. For example, the base sheet can be made entirely from synthetic fibers such as rayon, polyolefin fibers, polyester fibers, bicomponent sheath-core fibers, multi-component binder fibers, and the like. An exemplary polyethylene fiber is Fybrel®, available from Minifibers, Inc. (Jackson City, Tenn.). Any known bleaching method can be used. Synthetic cellulose fiber types include rayon in all its varieties and other fibers derived from viscose or chemically-modified cellulose. Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a base sheet can also be utilized in the present disclosure. For example, a papermaking process of the present disclosure can utilize creping, wet creping, double creping, embossing, wet pressing, air pressing, through-air drying, creped through-air drying, uncreped through-air drying, hydroentangling, air laying, coform methods, as well as other steps known in the art.

Also suitable for products of the present disclosure are wiping sheets that are pattern densified or imprinted, such as the tissue sheets disclosed in any of the following U.S. Pat. No. 4,514,345 issued on Apr. 30, 1985, to Johnson et al.; U.S. Pat. No. 4,528,239 issued on Jul. 9, 1985, to Trokhan; U.S. Pat. No. 5,098,522 issued on Mar. 24, 1992; U.S. Pat. No. 5,260,171 issued on Nov. 9, 1993, to Smurkoski et al.; U.S. Pat. No. 5,275,700 issued on Jan. 4, 1994, to Trokhan; U.S. Pat. No. 5,328,565 issued on Jul. 12, 1994, to Rasch et al.; U.S. Pat. No. 5,334,289 issued on Aug. 2, 1994, to Trokhan et al.; U.S. Pat. No. 5,431,786 issued on Jul. 11, 1995, to Rasch et al.; U.S. Pat. No. 5,496,624 issued on Mar. 5, 1996, to Steltjes, Jr. et al.; U.S. Pat. No. 5,500,277 issued on Mar. 19, 1996, to Trokhan et al.; U.S. Pat. No. 5,514,523 issued on May 7, 1996, to Trokhan et al.; U.S. Pat. No. 5,554,467 issued on Sep. 10, 1996, to Trokhan et al.; U.S. Pat. No. 5,566,724 issued on Oct. 22, 1996, to Trokhan et al.; U.S. Pat. No. 5,624,790 issued on Apr. 29, 1997, to Trokhan et al.; and, U.S. Pat. No. 5,628,876 issued on May 13, 1997, to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

The base web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents that may be used in the present disclosure include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 to Kaun which is incorporated herein by reference. In particular, Kaun discloses the use of cationic silicone compositions as debonding agents.

In one embodiment, the debonding agent used in the process of the present disclosure is an organic quaternary ammonium chloride and, particularly, a silicone-based amine salt of a quaternary ammonium chloride. For example, the debonding agent can be PROSOFT® TQ1003, marketed by the Hercules Corporation. The debonding agent can be added to the fiber slurry in an amount of from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corporation. The imidazoline-based debonding agent can be added in an amount of between 2.0 to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to forming a nonwoven web.

Optional chemical additives may also be added to the aqueous papermaking furnish or to the formed embryonic web to impart additional benefits to the product and process and are not antagonistic to the intended benefits of the invention. The following materials are included as examples of additional chemicals that may be applied to the web along with the additive composition of the present invention. The chemicals are included as examples and are not intended to limit the scope of the invention. Such chemicals may be added at any point in the papermaking process, including being added simultaneously with the additive composition in the pulp making process, wherein said additive or additives are blended directly with the additive composition.

Additional types of chemicals that may be added to the paper web include, but is not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamine, silicone, lotions in general and the like may also be incorporated into the finished products.

In general, the products of the present invention can be used in conjunction with any known materials and chemicals that are not antagonistic to its intended use. Examples of such materials include but are not limited to odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like.

The different chemicals and ingredients that may be incorporated into the base sheet may depend upon the end use of the product. For instance, various wet strength agents may be incorporated into the product. For bath tissue products, for example, temporary wet strength agents may be used. As used herein, wet strength agents are materials used to immobilize the bonds between fibers in the wet state. Typically, the means by which fibers are held together in paper and tissue products involve hydrogen bonds and sometimes combinations of hydrogen bonds and covalent and/or ionic bonds. In some applications, it may be useful to provide a material that will allow bonding to the fibers in such a way as to immobilize the fiber-to-fiber bond points and make them resistant to disruption in the wet state. The wet state typically means when the product is largely saturated with water or other aqueous solutions.

Any material that when added to a paper or tissue web results in providing the sheet with a mean wet geometric tensile strength:dry geometric tensile strength ratio in excess of 0.1 may be termed a wet strength agent.

Temporary wet strength agents, which are typically incorporated into bath tissues, are defined as those resins which, when incorporated into paper or tissue products, will provide a product which retains less than 50% of its original wet strength after exposure to water for a period of at least 5 minutes. Temporary wet strength agents are well known in the art. Examples of temporary wet strength agents include polymeric aldehyde-functional compounds such as glyoxylated polyacrylamide, such as a cationic glyoxylated polyacrylamide.

Such compounds include PAREZ 631 NC wet strength resin available from Cytec Industries of West Patterson, N.J., chloroxylated polyacrylamides, and HERCOBOND 1366, manufactured by Hercules, Inc. of Wilmington, Del. Another example of a glyoxylated polyacrylamide is PAREZ 745, which is a glyoxylated poly (acrylamide-co-diallyl dimethyl ammonium chloride).

For facial tissues and other tissue products, on the other hand, permanent wet strength agents may be incorporated into the base sheet. Permanent wet strength agents are also well known in the art and provide a product that will retain more than 50% of its original wet strength after exposure to water for a period of at least 5 minutes.

Once formed, the products may be packaged in different ways. For instance, in one embodiment, the wiping product may be cut into individual sheets and stacked prior to being placed into a package. Alternatively, the wiping product may be spirally wound. When spirally wound together, each individual sheet may be separated from an adjacent sheet by a line of weakness, such as a perforation line. Bath tissues and paper towels, for instance, are typically supplied to a consumer in a spirally wound configuration.

Base webs that may be treated in accordance with the present disclosure may include a single homogenous layer of fibers or may include a stratified or layered construction. For instance, the base web ply may include two or three layers of fibers. Each layer may have a different fiber composition. For example, referring to FIG. 1, one embodiment of a device for forming a multi-layered stratified pulp furnish is illustrated. As shown, a three-layered headbox 10 generally includes an upper head box wall 12 and a lower head box wall 14. Headbox 10 further includes a first divider 16 and a second divider 18, which separate three fiber stock layers.

Each of the fiber layers comprise a dilute aqueous suspension of papermaking fibers. The particular fibers contained in each layer generally depends upon the product being formed and the desired results. For instance, the fiber composition of each layer may vary depending upon whether a bath tissue product, facial tissue product or paper towel is being produced. In one embodiment, for instance, middle layer 20 contains southern softwood kraft fibers either alone or in combination with other fibers such as high yield fibers. Outer layers 22 and 24, on the other hand, contain softwood fibers, such as northern softwood kraft.

In an alternative embodiment, the middle layer may contain softwood fibers for strength, while the outer layers may comprise hardwood fibers, such as eucalyptus fibers, for a perceived softness.

An endless traveling forming fabric 26, suitably supported and driven by rolls 28 and 30, receives the layered papermaking stock issuing from headbox 10.

Once retained on fabric 26, the layered fiber suspension passes water through the fabric as shown by the arrows 32. Water removal is achieved by combinations of gravity, centrifugal force and vacuum suction depending on the forming configuration.

Forming multi-layered paper webs is also described and disclosed in U.S. Pat. No. 5,129,988 to Farrington, Jr., which is incorporated herein by reference.

In accordance with the present disclosure, the additive composition, in one embodiment, may be combined with the aqueous suspension of fibers that are fed to the headbox 10. The additive composition, for instance, may be applied to only a single layer in the stratified fiber furnish or to all layers. When added during the wet end of the process or otherwise combined with the aqueous suspension of fibers, the additive composition becomes incorporated throughout the fibrous layer.

When combined at the wet end with the aqueous suspension of fibers, a retention aid may also be present within the additive composition. For instance, in one particular embodiment, the retention aid may comprise polydiallyl dimethyl ammonium chloride. The additive composition may be incorporated into the base web in an amount from about 0.01% to about 30% by weight, such as from about 0.5% to about 20% by weight. For instance, in one embodiment, the additive composition may be present in an amount up to about 10% by weight. The above percentages are based upon the solids that are added to the base web.

The basis weight of base webs made in accordance with the present disclosure can vary depending upon the final product. For example, the process may be used to produce bath tissues, facial tissues, paper towels, industrial wipers, and the like. In general, the basis weight of the tissue products may vary from about 10 gsm to about 110 gsm, such as from about 20 gsm to about 90 gsm. For bath tissue and facial tissues, for instance, the basis weight may range from about 10 gsm to about 40 gsm. For paper towels, on the other hand, the basis weight may range from about 25 gsm to about 80 gsm.

The wiping product may have any bulk; for example, the wiping product may have a bulk of less than 3 cc/g; or in the alternative, the wiping product may have a bulk in the range of equal or greater than 3 cc/g; such as 3 cc/g to 20 cc/g, such as from about 5 cc/g to 15 cc/g. The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc., Newberg, Oreg. The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

In multiple ply products, the basis weight of each base web present in the product can also vary. In general, the total basis weight of a multiple ply product will generally be the same as indicated above, such as from about 20 gsm to about 110 gsm. Thus, the basis weight of each ply can be from about 10 gsm to about 60 gsm, such as from about 20 gsm to about 40 gsm.

Figure 2:
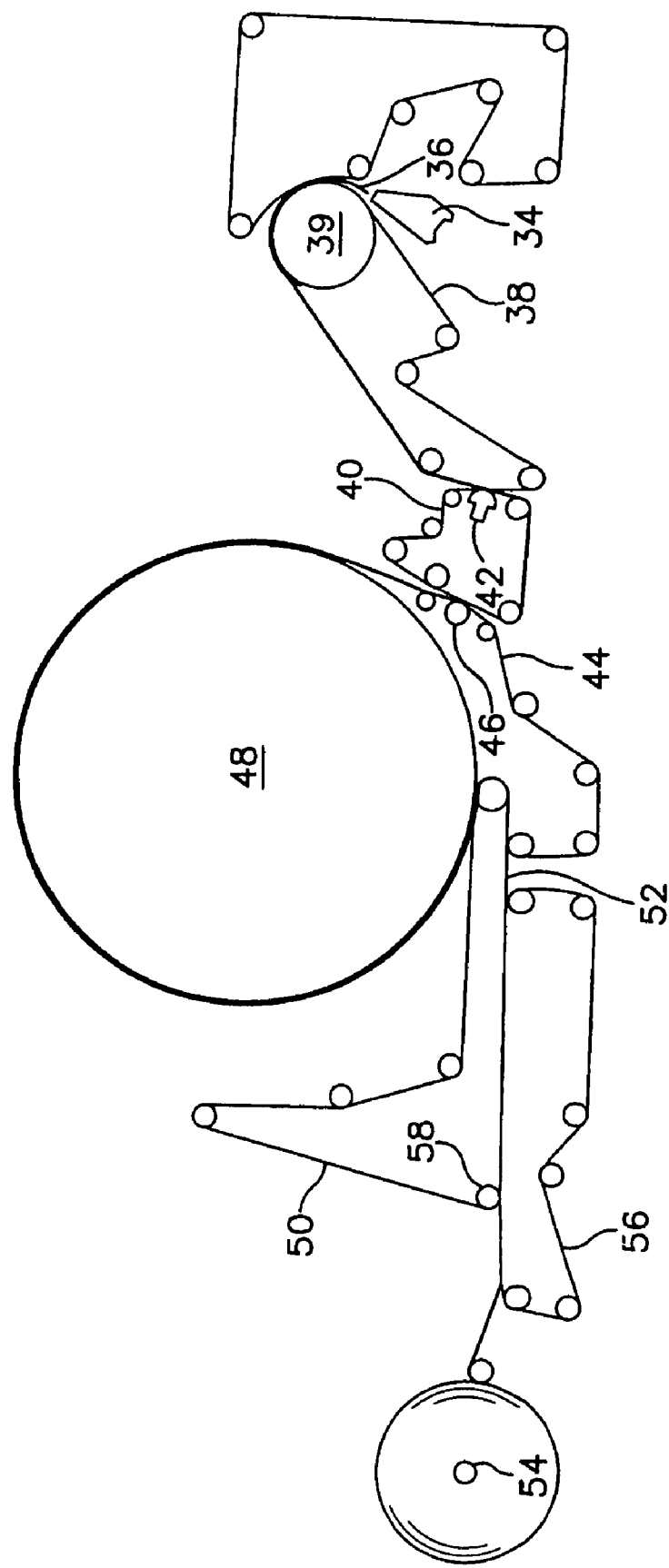
FIG. 2 is a schematic diagram of one embodiment of a process for forming uncreped through-dried base webs for use in the present disclosure.

In one embodiment, once the aqueous suspension of fibers is formed into a base web, the base web may be processed using various techniques and methods. For example, referring to FIG. 2, shown is a method for making throughdried tissue sheets. (For simplicity, the various tensioning rolls schematically used to define the several fabric runs are shown, but not numbered. It will be appreciated that variations from the apparatus and method illustrated in FIG. 2 can be made without departing from the general process). Shown is a twin wire former having a papermaking headbox 34, such as a layered headbox, which injects or deposits a stream 36 of an aqueous suspension of papermaking fibers onto the forming fabric 38 positioned on a forming roll 39. The forming fabric serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 40. In one embodiment, the transfer fabric can be traveling at a slower speed than the forming fabric in order to impart increased stretch into the web. This is commonly referred to as a "rush" transfer. Preferably the transfer fabric can have a void volume that is equal to or less than that of the forming fabric. The relative speed difference between the two fabrics can be from 0-60 percent, more specifically from about 15-45 percent. Transfer is preferably carried out with the assistance of a vacuum shoe 42 such that the forming fabric and the transfer fabric simultaneously converge and diverge at the leading edge of the vacuum slot.

The web is then transferred from the transfer fabric to the throughdrying fabric 44 with the aid of a vacuum transfer roll 46 or a vacuum transfer shoe, optionally again using a fixed gap transfer as previously described. The throughdrying fabric can be traveling at about the same speed or a different speed relative to the transfer fabric. If desired, the throughdrying fabric can be run at a slower speed to further enhance stretch. Transfer can be carried out with vacuum assistance to ensure deformation of the sheet to conform to the throughdrying fabric, thus yielding desired bulk and appearance if desired. Suitable throughdrying fabrics are described in U.S. Pat. No. 5,429,686 issued to Kai F. Chiu et al. and U.S. Pat. No. 5,672,248 to Wendt, et al. which are incorporated by reference.

In one embodiment, the throughdrying fabric contains high and long impression knuckles. For example, the throughdrying fabric can have about from about 5 to about 300 impression knuckles per square inch which are raised at least about 0.005 inches above the plane of the fabric. During drying, the web can be macroscopically arranged to conform to the surface of the throughdrying fabric and form a three-dimensional surface. Flat surfaces, however, can also be used in the present disclosure.

The side of the web contacting the throughdrying fabric is typically referred to as the "fabric side" of the paper web. The fabric side of the paper web, as described above, may have a shape that conforms to the surface of the throughdrying fabric after the fabric is dried in the throughdryer. The opposite side of the paper web, on the other hand, is typically referred to as the "air side". The air side of the web is typically smoother than the fabric side during normal throughdrying processes.

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric, the web is finally dried to a consistency of about 94 percent or greater by the throughdryer 48 and thereafter transferred to a carrier fabric 50. The dried base sheet 52 is transported to the reel 54 using carrier fabric 50 and an optional carrier fabric 56. An optional pressurized turning roll 58 can be used to facilitate transfer of the web from carrier fabric 50 to fabric 56. Suitable carrier fabrics for this purpose are Albany International 84M or 94M and Asten 959 or 937, all of which are relatively smooth fabrics having a fine pattern. Although not shown, reel calendering or subsequent off-line calendering can be used to improve the smoothness and softness of the base sheet.

In one embodiment, the reel 54 shown in FIG. 2 can run at a speed slower than the fabric 56 in a rush transfer process for building crepe into the paper web 52. For instance, the relative speed difference between the reel and the fabric can be from about 5% to about 25% and, particularly from about 12% to about 14%. Rush transfer at the reel can occur either alone or in conjunction with a rush transfer process upstream, such as between the forming fabric and the transfer fabric.

In one embodiment, the paper web 52 is a textured web which has been dried in a three-dimensional state such that the hydrogen bonds joining fibers were substantially formed while the web was not in a flat, planar state. For instance, the web can be formed while the web is on a highly textured throughdrying fabric or other three-dimensional substrate. Processes for producing uncreped throughdried fabrics are, for instance, disclosed in U.S. Pat. No. 5,672,248 to Wendt, et al.; U.S. Pat. No. 5,656,132 to Farrington, et al.; U.S. Pat. No. 6,120,642 to Lindsay and Burazin; U.S. Pat. No. 6,096,169 to Hermans, et al.; U.S. Pat. No. 6,197,154 to Chen, et al.; and U.S. Pat. No. 6,143,135 to Hada, et al., all of which are herein incorporated by reference in their entireties.

As described above, the additive composition can be combined with the aqueous suspension of fibers used to form the base web 52. Alternatively, the additive composition may be topically applied to the base web after it has been formed. For instance, as shown in FIG. 2, the additive composition may be applied to the base web prior to the dryer 48 or after the dryer 48.

In FIG. 2, a process is shown for producing uncreped through-air dried base webs. It should be understood, however, that the additive composition may be applied to base webs in other tissue making processes. For example, referring to FIG. 3, one embodiment of a process for forming wet pressed creped base webs is shown. In this embodiment, a headbox 60 emits an aqueous suspension of fibers onto a forming fabric 62 which is supported and driven by a plurality of guide rolls 64. A vacuum box 66 is disposed beneath forming fabric 62 and is adapted to remove water from the fiber furnish to assist in forming a web. From forming fabric 62, a formed web 68 is transferred to a second fabric 70, which may be either a wire or a felt. Fabric 70 is supported for movement around a continuous path by a plurality of guide rolls 72. Also included is a pick up roll 74 designed to facilitate transfer of web 68 from fabric 62 to fabric 70.

From fabric 70, web 68, in this embodiment, is transferred to the surface of a rotatable heated dryer drum 76, such as a Yankee dryer.

In accordance with the present disclosure, the additive composition can be incorporated into the base web 68 by being combined with an aqueous suspension of fibers contained in the headbox 60 and/or by topically applying the additive composition during the process. In one particular embodiment, the additive composition of the present disclosure may be applied topically to the base web 68 while the web is traveling on the fabric 70 or may be applied to the surface of the dryer drum 76 for transfer onto one side of the base web 68. In this manner, the additive composition is used to adhere the base web 68 to the dryer drum 76. In this embodiment, as web 68 is carried through a portion of the rotational path of the dryer surface, heat is imparted to the web causing most of the moisture contained within the web to be evaporated. Web 68 is then removed from dryer drum 76 by a creping blade 78. Creping web 78 as it is formed further reduces internal bonding within the web and increases softness. Applying the additive composition to the web during creping, on the other hand, may increase the strength of the web.

Figure 35:
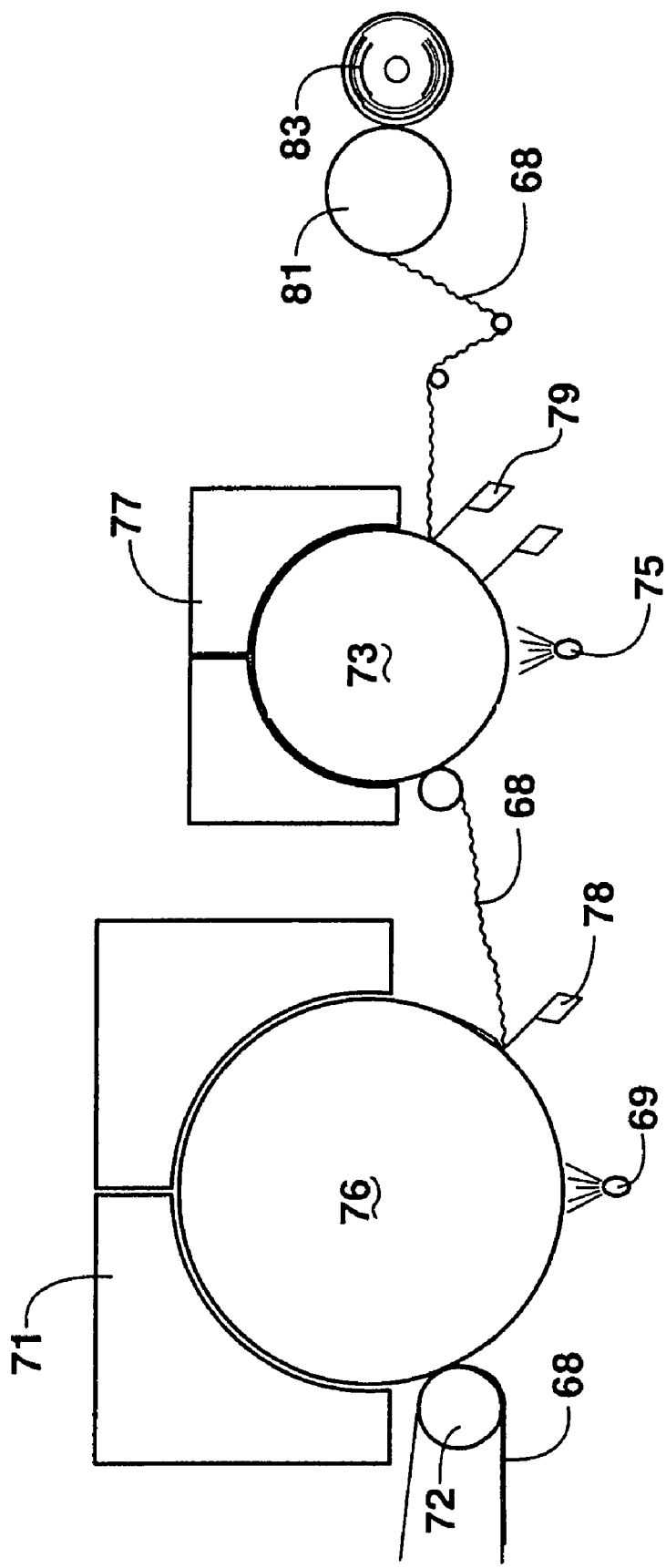
FIG. 35 is a schematic diagram of another embodiment of a process for forming creped base webs in accordance with the present disclosure.

Referring to FIG. 35, another alternative embodiment of a process for forming creped base webs is shown. Like reference numerals have been used to indicate similar elements with respect to the process illustrated in FIG. 3.

As shown in FIG. 35, the formed web 68 is transferred to the surface of the rotatable heated dryer drum 76, which may be a Yankee dryer. The press roll 72 may, in one embodiment, comprise a suction breast roll. In order to adhere the web 68 to the surface of the dryer drum 76, a creping adhesive may be applied to the surface of the dryer drum by a spraying device 69. The spraying device 69 may emit an additive composition made in accordance with the present disclosure or may emit a conventional creping adhesive.

As shown in FIG. 35, the web is adhered to the surface of the dryer drum 76 and then creped from the drum using the creping blade 78. If desired, the dryer drum 76 may be associated with a hood 71. The hood 71 may be used to force air against or through the web 68.

Once creped from the dryer drum 76, the web 68 is then adhered to a second dryer drum 73. The second dryer drum 73 may comprise, for instance, a heated drum surrounded by a hood 77. The drum may be heated to a temperature of from about 25° C. to about 200° C., such as from about 100° C. to about 150° C.

In order to adhere the web 68 to the second dryer drum 73, a second spray device 75 may emit an adhesive onto the surface of the dryer drum. In accordance with the present disclosure, for instance, the second spray device 75 may emit an additive composition as described above. The additive composition not only assists in adhering the base web 68 to the dryer drum 73, but also is transferred to the surface of the web as the web is creped from the dryer drum 73 by the creping blade 79.

Once creped from the second dryer drum 73, the web 68 may, optionally, be fed around a cooling reel drum 81 and cooled prior to being wound on a reel 83.

The additive composition may also be used in post-forming processes. For example, in one embodiment, the additive composition may be used during a print-creping process and applied to a preformed web. Specifically, once topically applied to a base web, the additive composition has been found well-suited to adhering the base web to a creping surface, such as in a print-creping operation.

For example, once a base web is formed and dried, in one embodiment, the additive composition may be applied to at least one side of the web and then at least one side of the web may then be creped. In general, the additive composition may be applied to only one side of the web and only one side of the web may be creped, the additive composition may be applied to both sides of the web and only one side of the web is creped, or the additive composition may be applied to each side of the web and each side of the web may be creped.

Figure 3:
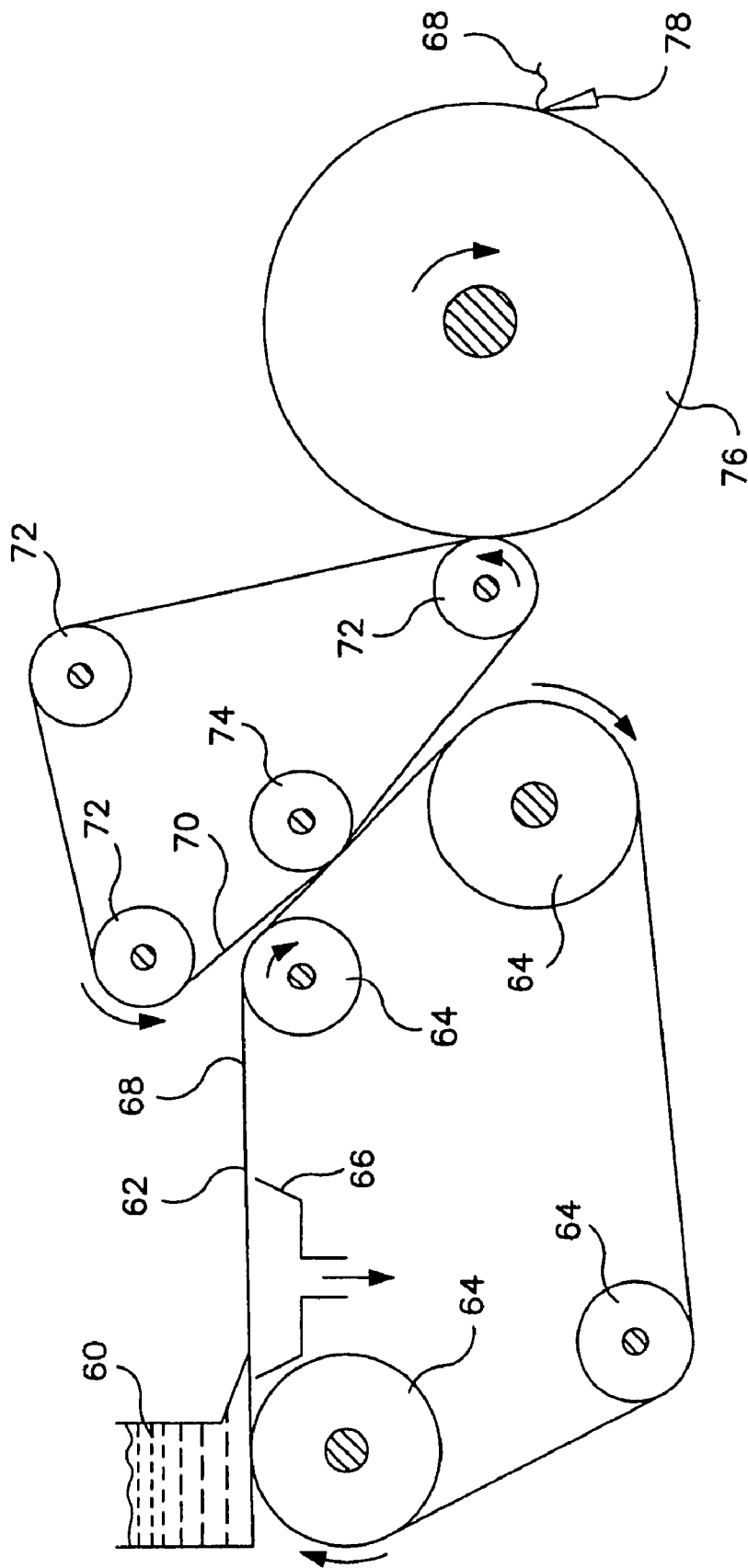
FIG. 3 is a schematic diagram of one embodiment of a process for forming wet pressed, creped base webs for use in the present disclosure.
Figure 4:
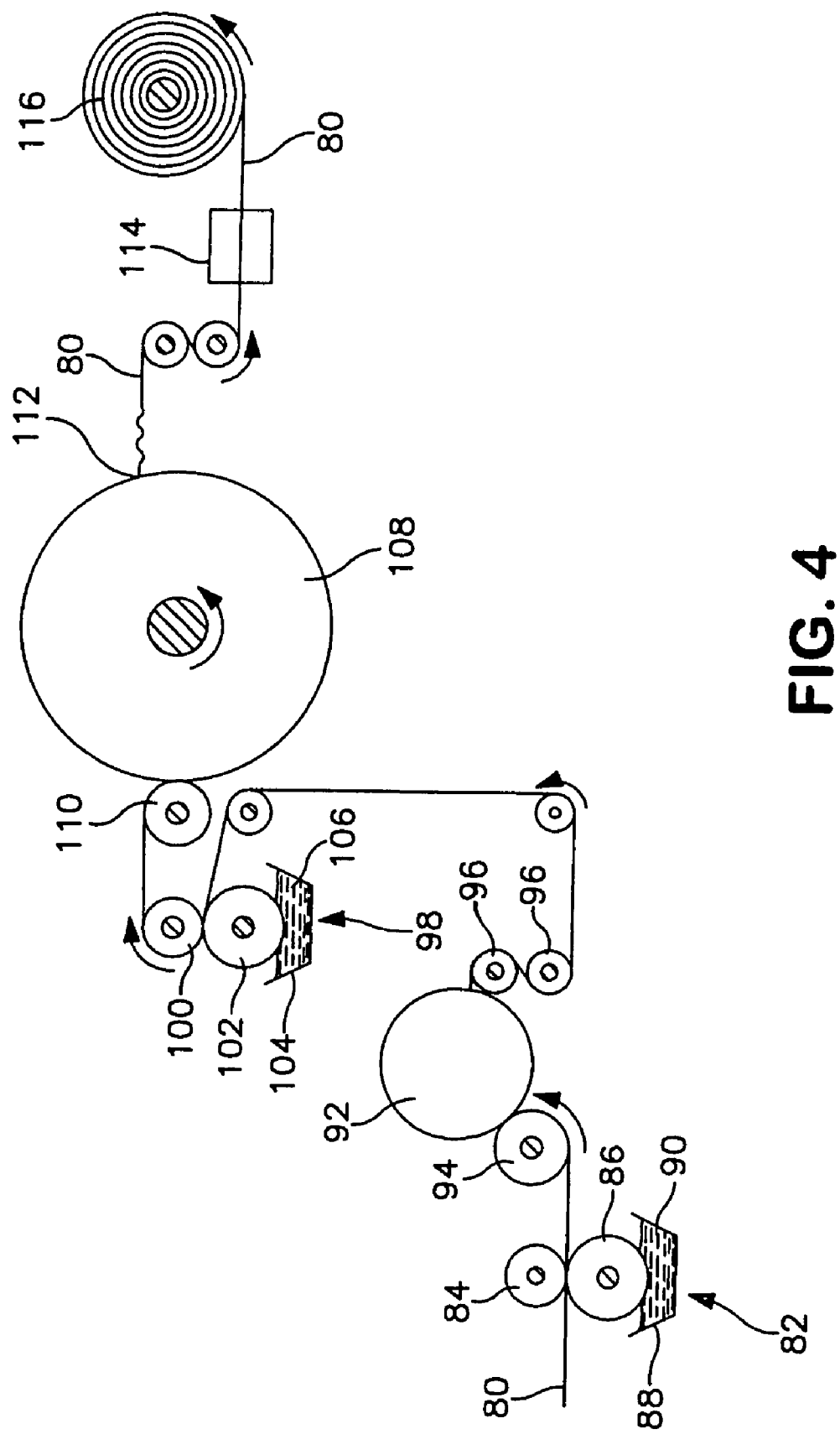
FIG. 4 is a schematic diagram of one embodiment of a process for applying additive compositions to each side of a base web and creping one side of the web in accordance with the present disclosure.

Referring to FIG. 4 one embodiment of a system that may be used to apply the additive composition to the base web and to crepe one side of the web is illustrated. The embodiment shown in FIG. 4 can be an in-line or off-line process. As shown, base web 80 made according to the process illustrated in FIG. 2 or FIG. 3 or according to a similar process, is passed through a first additive composition application station generally 82. Station 82 includes a nip formed by a smooth rubber press roll 84 and a patterned rotogravure roll 86. Rotogravure roll 86 is in communication with a reservoir 88 containing a first additive composition 90. Rotogravure roll 86 applies the additive composition 90 to one side of web 80 in a preselected pattern.

Web 80 is then contacted with a heated roll 92 after passing a roll 94. The heated roll 92 can be heated to a temperature, for instance, up to about 200° C. and particularly from about 100° C. to about 150° C. In general, the web can be heated to a temperature sufficient to dry the web and evaporate any water.

It should be understood, that the besides the heated roll 92, any suitable heating device can be used to dry the web. For example, in an alternative embodiment, the web can be placed in communication with an infra-red heater in order to dry the web. Besides using a heated roll or an infra-red heater, other heating devices can include, for instance, any suitable convective oven or microwave oven.

From the heated roll 92, the web 80 can be advanced by pull rolls 96 to a second additive composition application station generally 98. Station 98 includes a transfer roll 100 in contact with a rotogravure roll 102, which is in communication with a reservoir 104 containing a second additive composition 106. Similar to station 82, second additive composition 106 is applied to the opposite side of web 80 in a preselected pattern. Once the second additive composition is applied, web 80 is adhered to a creping roll 108 by a press roll 110. Web 80 is carried on the surface of the creping drum 108 for a distance and then removed therefrom by the action of a creping blade 112. The creping blade 112 performs a controlled pattern creping operation on the second side of the base web.

Once creped, base web 80, in this embodiment, is pulled through a drying station 114. Drying station 114 can include any form of a heating unit, such as an oven energized by infra-red heat, microwave energy, hot air or the like. Drying station 114 may be necessary in some applications to dry the web and/or cure the additive composition. Depending upon the additive composition selected, however, in other applications drying station 114 may not be needed.

The amount that the base web is heated within the drying station 114 can depend upon the particular thermoplastic resins used in the additive composition, the amount of the composition applied to the web, and the type of web used. In some applications, for instance, the base web can be heated using a gas stream such as air at a temperature of about 100° C. to about 200° C.

In the embodiment illustrated in FIG. 4, although the additive composition is being applied to each side of the base web, only one side of the web undergoes a creping process. It should be understood, however, that in other embodiments both sides of the web may be creped. For instance, the heated roll 92 may be replaced with a creping drum such as 108 shown in FIG. 4.

Creping the base web as shown in FIG. 4 increases the softness of the web by breaking apart fiber-to-fiber bonds contained within the base web. Applying the additive composition to the outside of the paper web, on the other hand, not only assists in creping the web but also adds dry strength, wet strength, stretchability and tear resistance to the web. Further, the additive composition reduces the release of lint from the base web.

In general, the first additive composition and the second additive composition applied to the base web as shown in FIG. 4 may contain the same ingredients or may contain different ingredients. Alternatively, the additive compositions may contain the same ingredients in different amounts as desired.

The additive composition is applied to the base web as described above in a preselected pattern. In one embodiment, for instance, the additive composition can be applied to the web in a reticular pattern, such that the pattern is interconnected forming a net-like design on the surface.

In an alternative embodiment, however, the additive composition is applied to the web in a pattern that represents a succession of discrete shapes. Applying the additive composition in discrete shapes, such as dots, provides sufficient strength to the web without covering a substantial portion of the surface area of the web.

According to the present disclosure, the additive composition is applied to each side of the paper web so as to cover from about 15% to about 75% of the surface area of the web. More particularly, in most applications, the additive composition will cover from about 20% to about 60% of the surface area of each side of the web. The total amount of additive composition applied to each side of the web can be in the range of from about 1% to about 30% by weight, based upon the total weight of the web, such as from about 1% to about 20% by weight, such as from about 2% to about 10% by weight.

At the above amounts, the additive composition can penetrate the base web after being applied in an amount up to about 30% of the total thickness of the web, depending upon various factors. It has been discovered, however, that most of the additive composition primarily resides on the surface of the web after being applied to the web. For instance, in some embodiments, the additive composition penetrates the web less than 5%, such as less than 3%, such as less than 1% of the thickness of the web.

Figure 5:
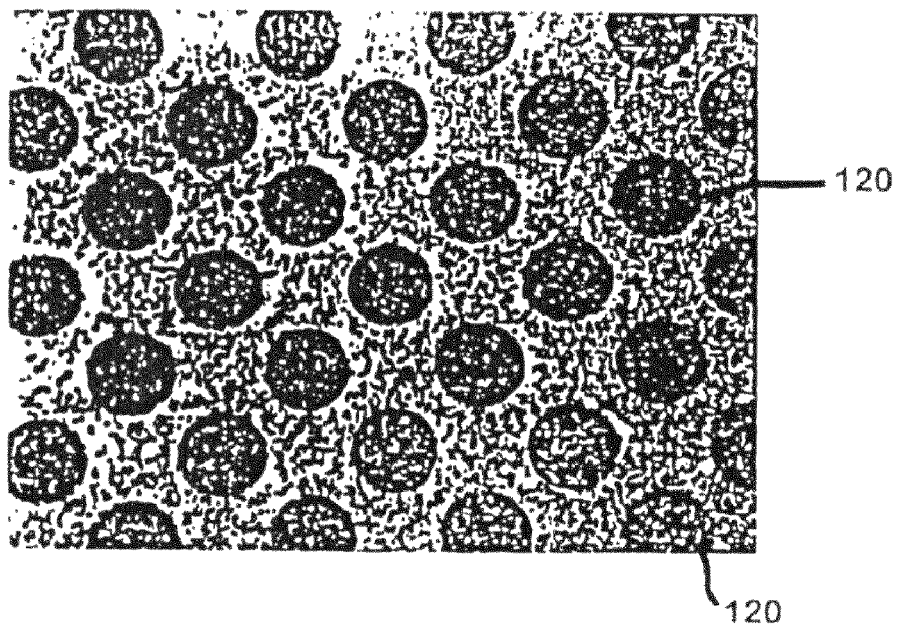
FIG. 5 is a plan view of one embodiment of a pattern that is used to apply additive compositions to base webs made in accordance with the present disclosure.

Referring to FIG. 5, one embodiment of a pattern that can be used for applying an additive composition to a paper web in accordance with the present disclosure is shown. As illustrated, the pattern shown in FIG. 5 represents a succession of discrete dots 120. In one embodiment, for instance, the dots can be spaced so that there are approximately from about 25 to about 35 dots per inch in the machine direction or the cross-machine direction. The dots can have a diameter, for example, of from about 0.01 inches to about 0.03 inches. In one particular embodiment, the dots can have a diameter of about 0.02 inches and can be present in the pattern so that approximately 28 dots per inch extend in either the machine direction or the cross-machine direction. In this embodiment, the dots can cover from about 20% to about 30% of the surface area of one side of the paper web and, more particularly, can cover about 25% of the surface area of the web.

Figure 7:
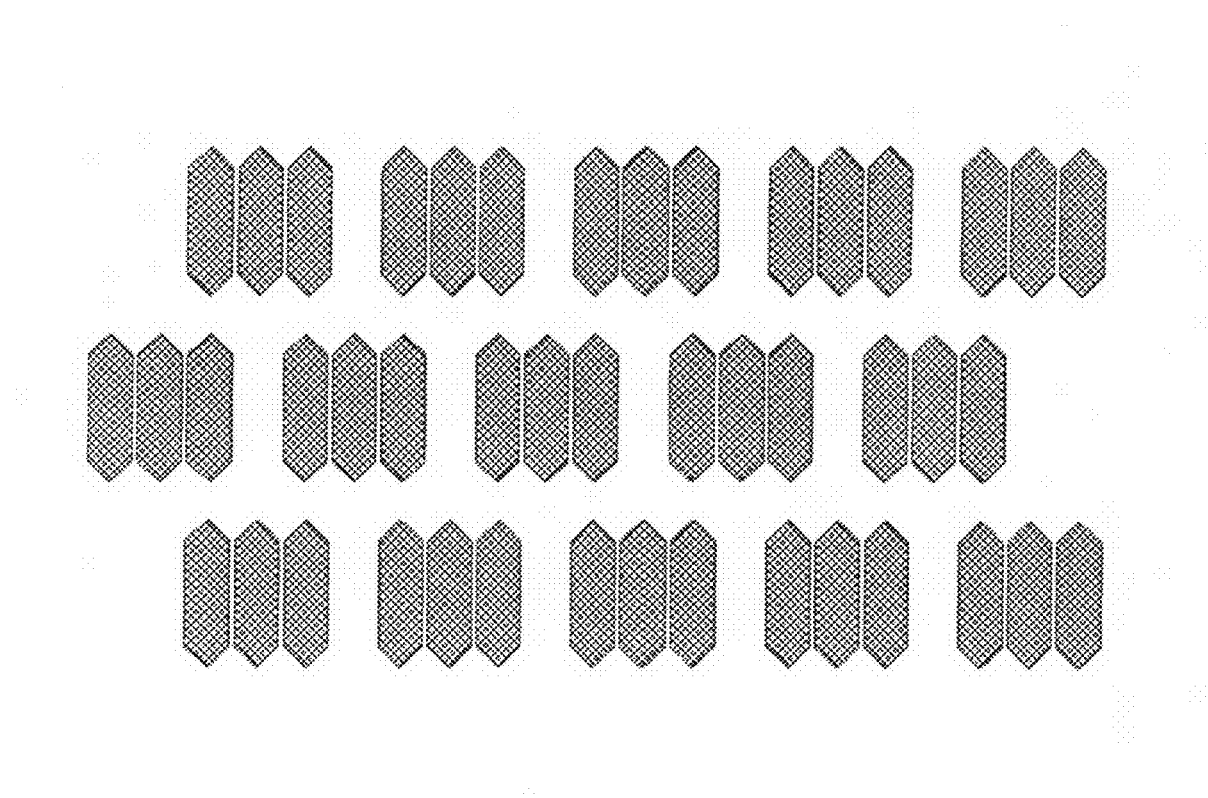
FIG. 7 is a plan view of another alternative embodiment of a pattern that is used to apply additive compositions to base webs in accordance with the present disclosure.

Besides dots, various other discrete shapes can also be used. For example, as shown in FIG. 7, a pattern is illustrated in which the pattern is made up of discrete shapes that are each comprised of three elongated hexagons. In one embodiment, the hexagons can be about 0.02 inches long and can have a width of about 0.006 inches. Approximately 35 to 40 hexagons per inch can be spaced in the machine direction and the cross-machine direction. When using hexagons as shown in FIG. 7, the pattern can cover from about 40% to about 60% of the surface area of one side of the web, and more particularly can cover about 50% of the surface area of the web.

Figure 6:
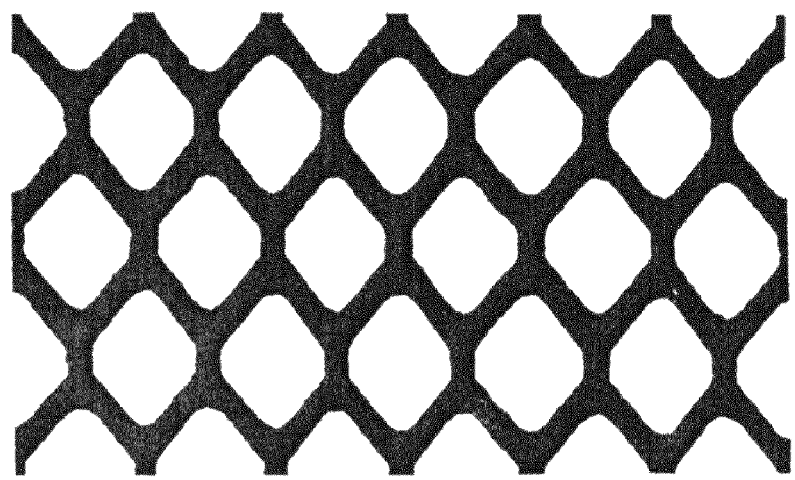
FIG. 6 is another embodiment of a pattern that is used to apply additive compositions to base webs in accordance with the present disclosure.

Referring to FIG. 6, another embodiment of a pattern for applying an additive composition to a paper web is shown. In this embodiment, the pattern is a reticulated grid. More specifically, the reticulated pattern is in the shape of diamonds. When used, a reticulated pattern may provide more strength to the web in comparison to patterns that are made up on a succession of discrete shapes.

The process that is used to apply the additive composition to the base web in accordance with the present disclosure can vary. For example, various printing methods can be used to print the additive composition onto the base sheet depending upon the particular application. Such printing methods can include direct gravure printing using two separate gravures for each side, offset gravure printing using duplex printing (both sides printed simultaneously) or station-to-station printing (consecutive printing of each side in one pass). In another embodiment, a combination of offset and direct gravure printing can be used. In still another embodiment, flexographic printing using either duplex or station-to-station printing can also be utilized to apply the additive composition.

According to the process of the current disclosure, numerous and different tissue products can be formed. For instance, the tissue products may be single-ply wiper products. The products can be, for instance, facial tissues, bath tissues, paper towels, napkins, industrial wipers, and the like. As stated above, the basis weight can range anywhere from about 10 gsm to about 110 gsm.

Wiping products made according to the above processes can have relatively good bulk characteristics. For example, wiping products made according to instant invention may have a bulk density in the range of less than 3 cc/g; or in the alternative, such wiping products may have a bulk of at least 3 cc/g.

In one embodiment, base webs made according to the present disclosure can be incorporated into multiple-ply products. For instance, in one embodiment, a base web made according to the present disclosure can be attached to one or more other base webs for forming a wiping product having desired characteristics. The other webs laminated to the base web of the present disclosure can be, for instance, a wet-creped web, a calendered web, an embossed web, a through-air dried web, a creped through-air dried web, an uncreped through-air dried web, a hydroentangled web, a coform web, an airlaid web, and the like.

In one embodiment, when incorporating a base web made according to the present disclosure into a multiple-ply product, it may be desirable to only apply the additive composition to one side of the base web and to thereafter crepe the treated side of the web. The creped side of the web is then used to form an exterior surface of a multiple ply product. The untreated and uncreped side of the web, on the other hand, is attached by any suitable means to one or more plies.

Figure 8:
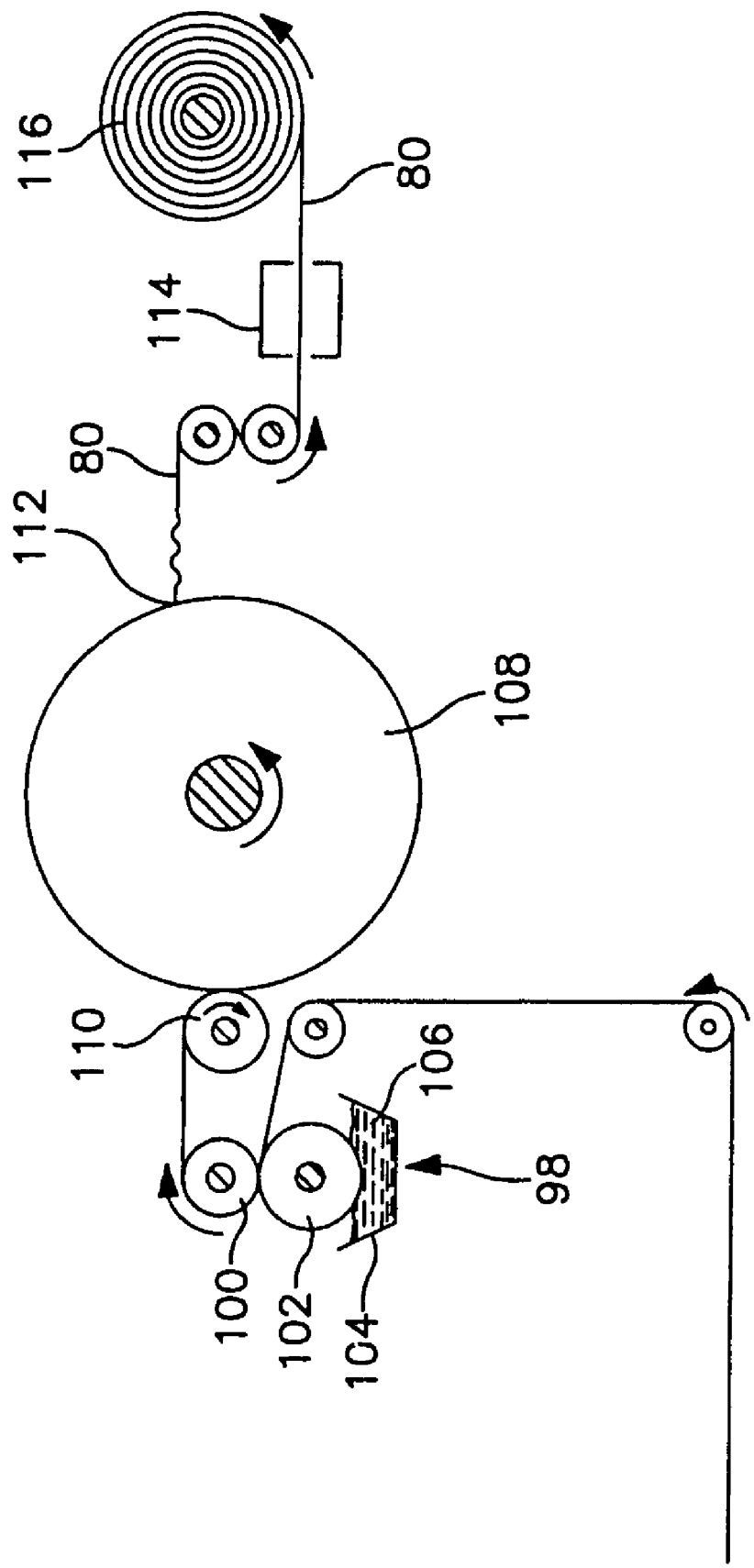
FIG. 8 is a schematic diagram of an alternative embodiment of a process for applying an additive composition to one side of the base web and creping one side of the web in accordance with the present disclosure.
Figure 9:
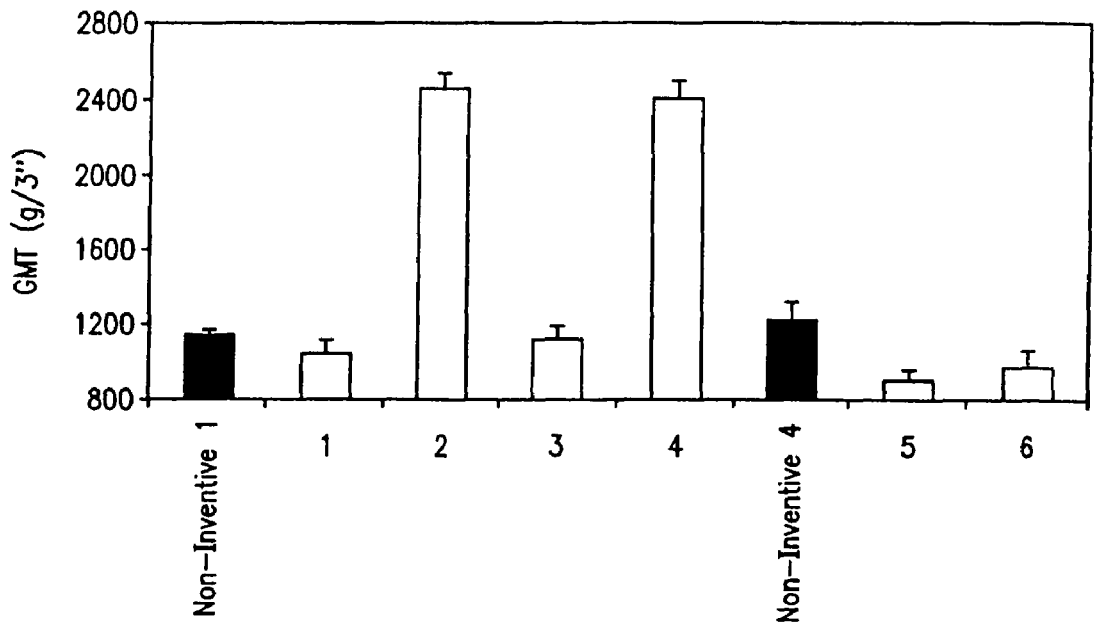
FIGS. 9-26 and 28-34 are the results obtained in the Examples as described below.
Figure 10:
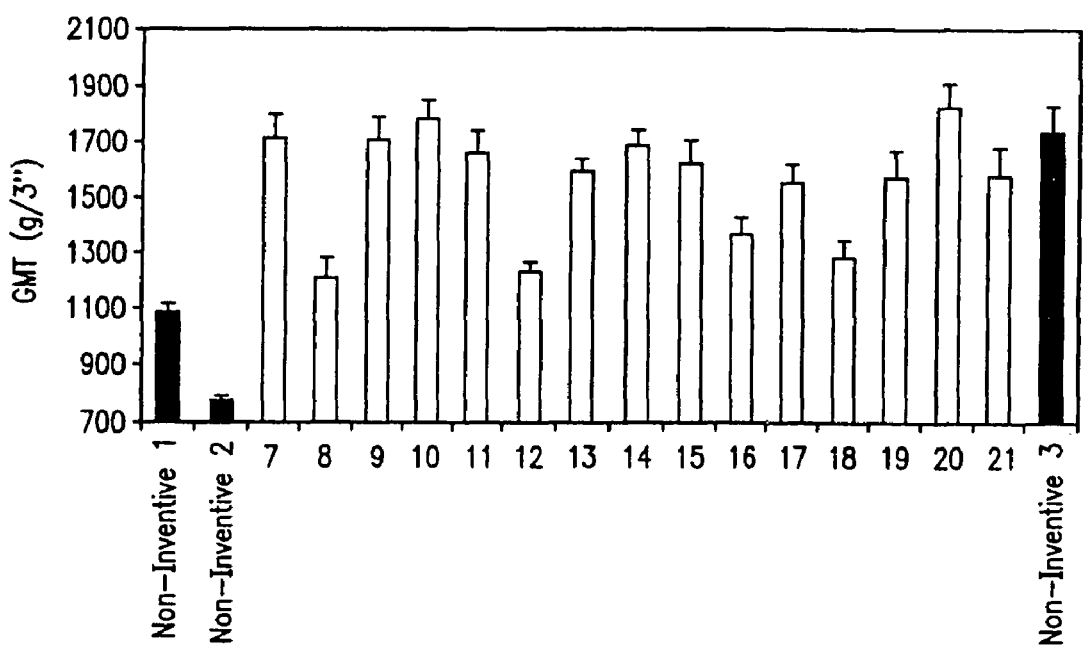
Figure 11:
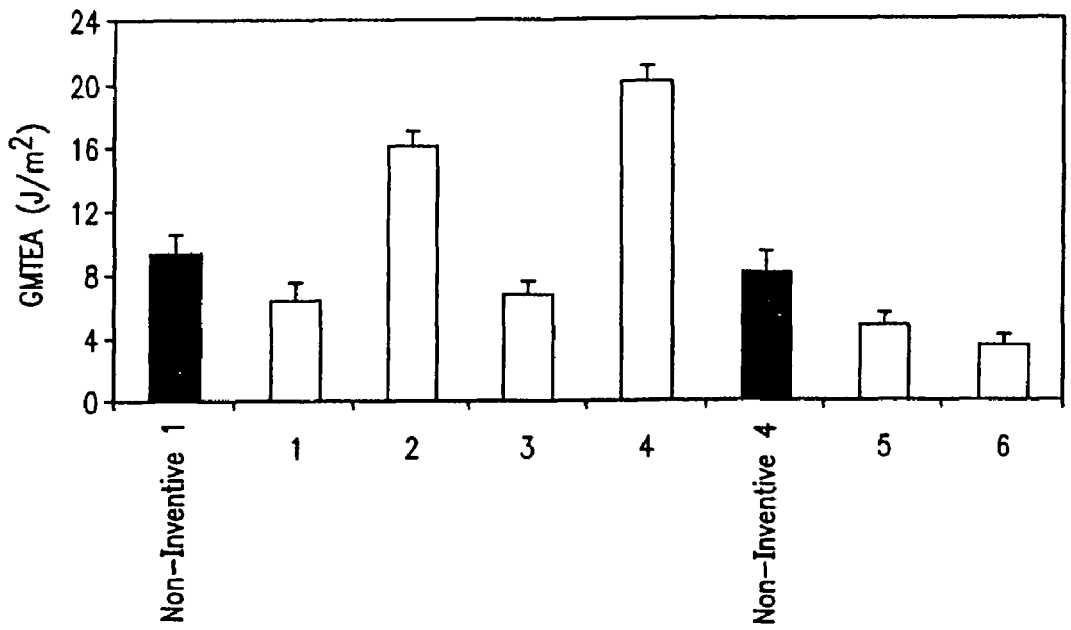
Figure 12:
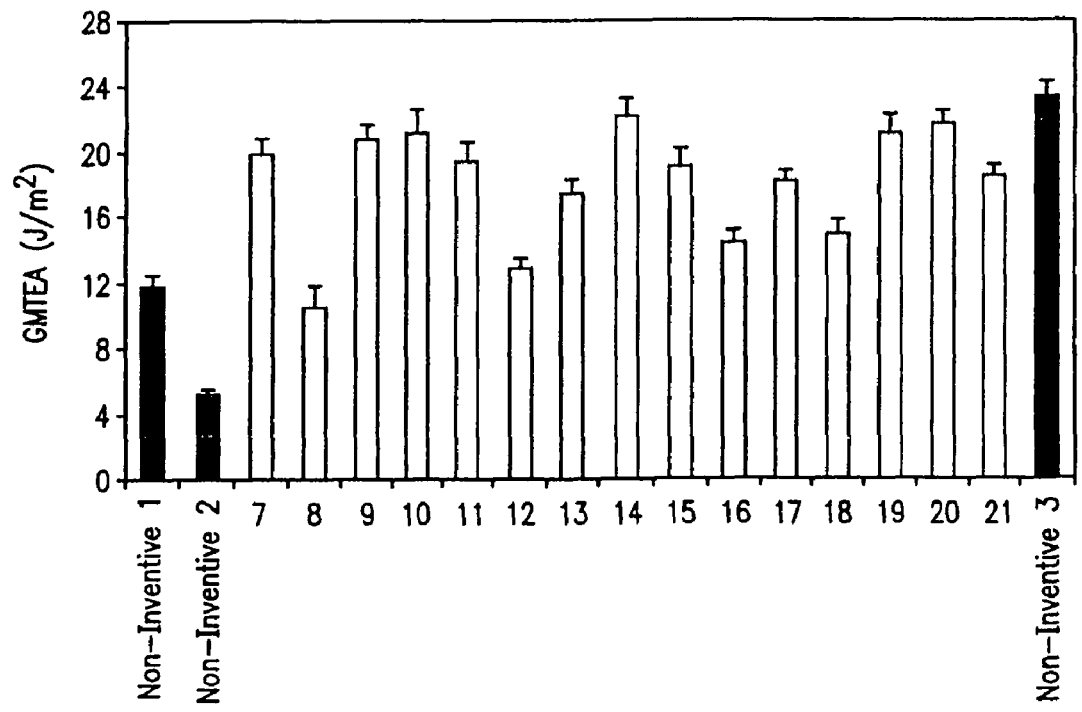
Figure 13:
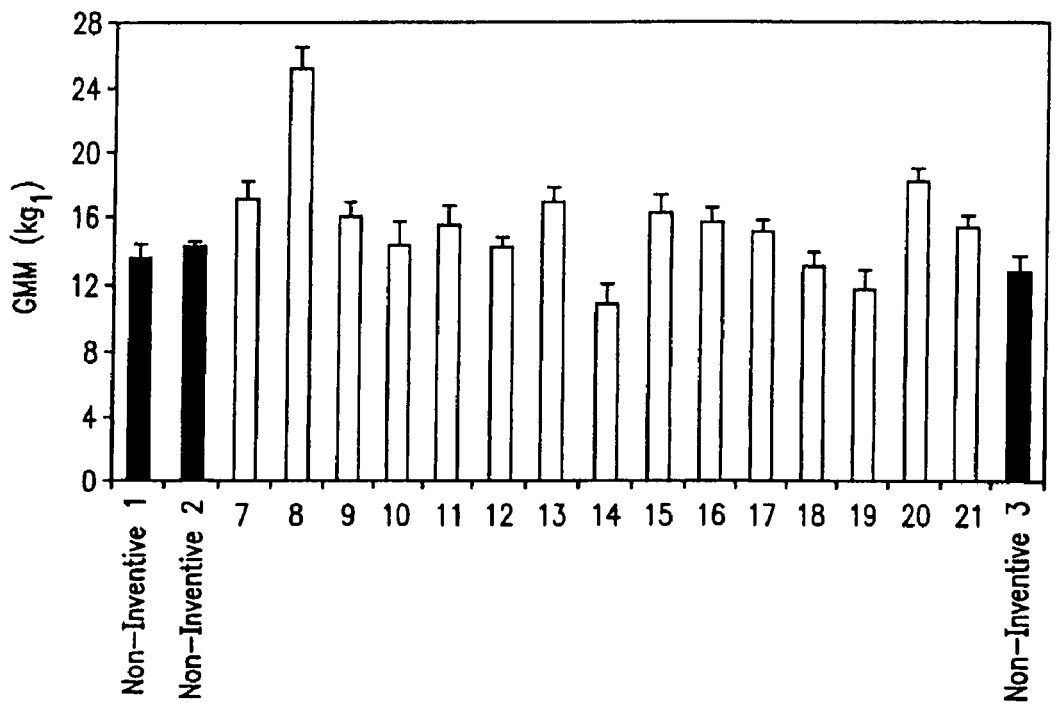
Figure 14:
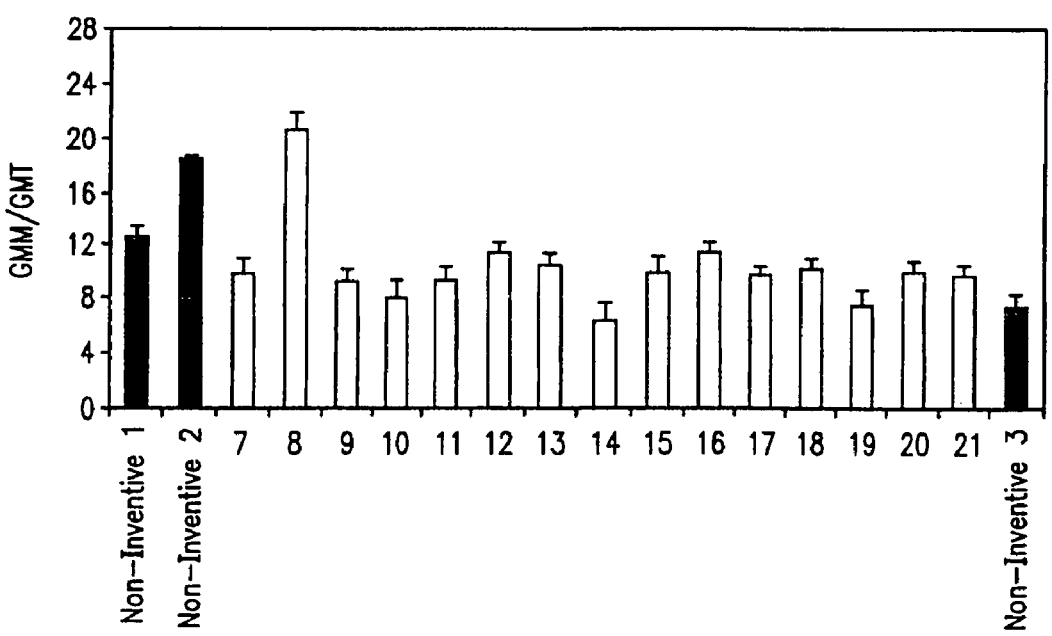
Figure 15:
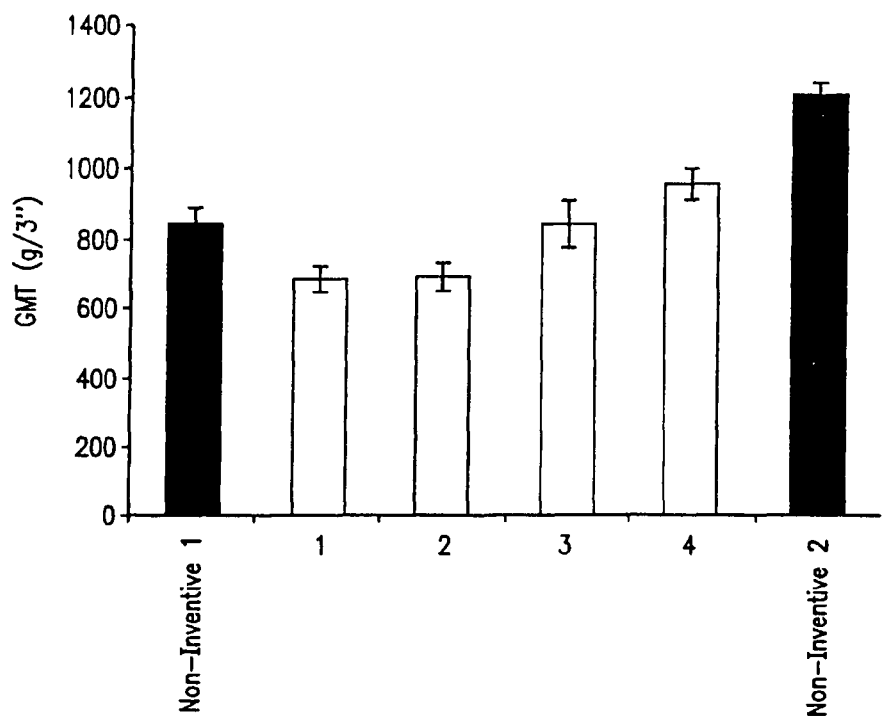
Figure 16:
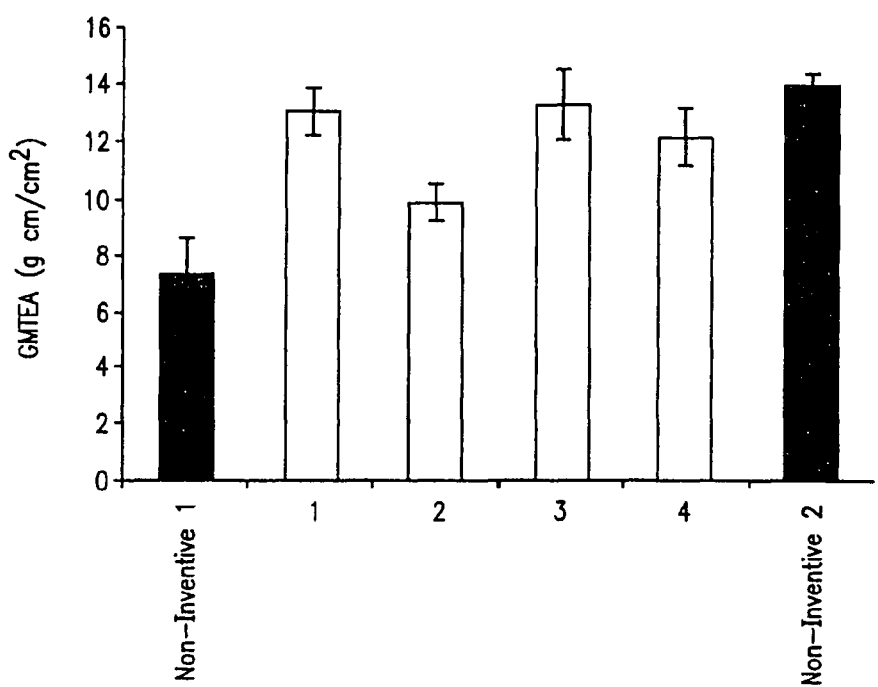
Figure 17:
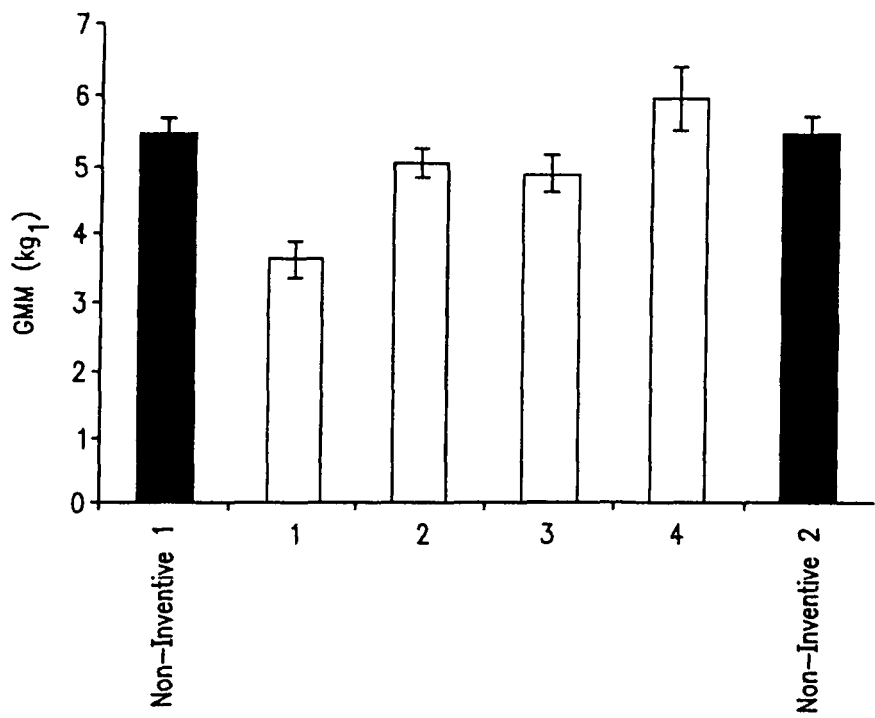
Figure 18:
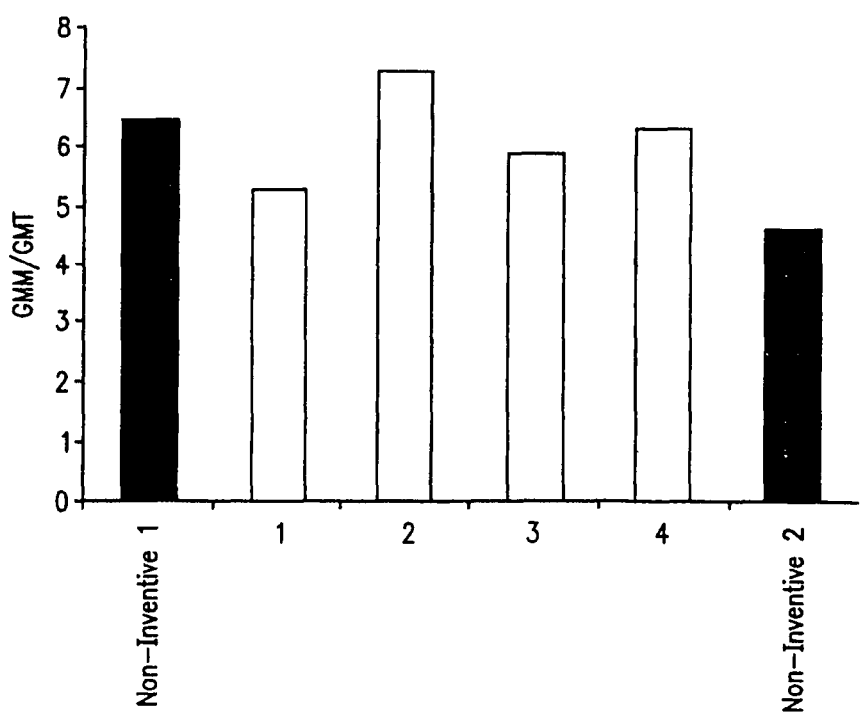
Figure 19:
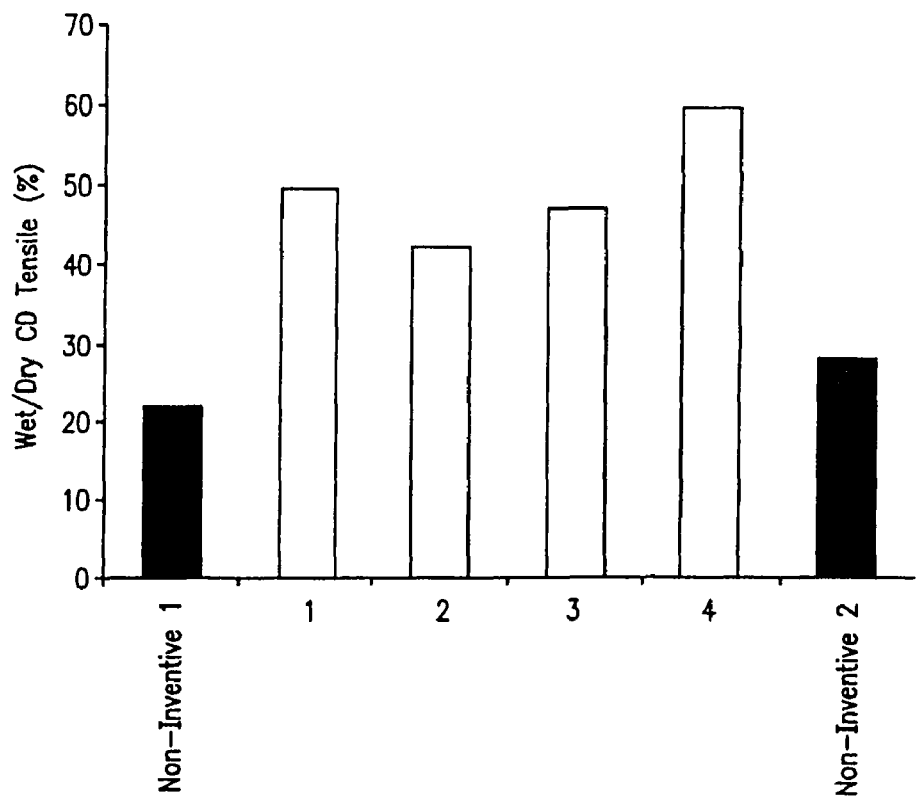

For example, referring to FIG. 8, one embodiment of a process for applying the additive composition to only one side of a base web in accordance with the present disclosure is shown. The process illustrated in FIG. 8 is similar to the process shown in FIG. 4. In this regard, like reference numerals have been used to indicate similar elements.

As shown, a web 80 is advanced to an additive composition application station generally 98. Station 98 includes a transfer roll 100 in contact with a rotogravure roll 102, which is in communication with a reservoir 104 containing an additive composition 106. At station 98, the additive composition 106 is applied to one side of the web 80 in a preselected pattern.

Once the additive composition is applied, web 80 is adhered to a creping roll 108 by a press roll 110. Web 80 is carried on the surface of the creping drum 108 for a distance and then removed therefrom by the action of a creping blade 112. The creping blade 112 performs a controlled pattern creping operation on the treated side of the web.

From the creping drum 108, the base web 80 is fed through a drying station 114 which dries and/or cures the additive composition 106. The web 80 is then wound into a roll 116 for use in forming multiple ply products or a single ply product.

Figure 36:
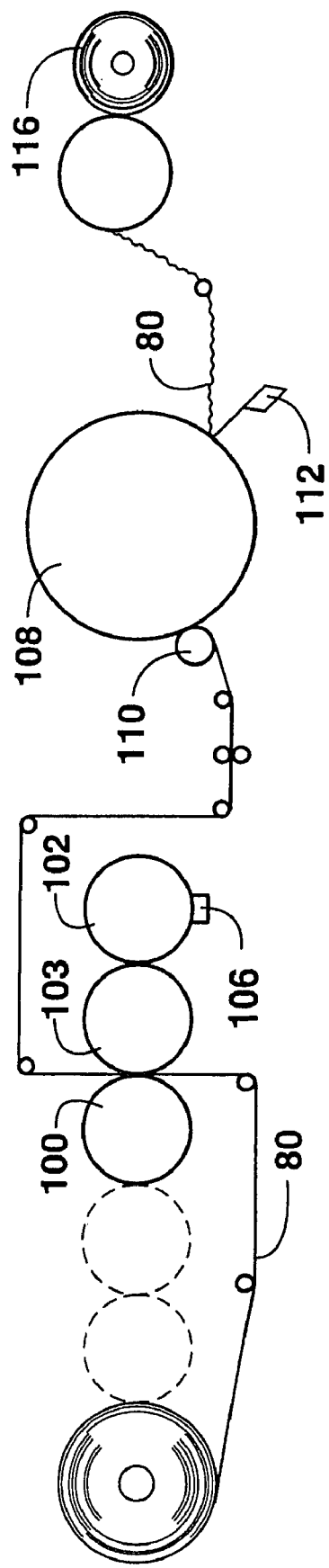
FIG. 36 is a schematic diagram of still another embodiment of a process for applying an additive composition to one side of a base web and creping one side of the web in accordance with the present disclosure.

Referring to FIG. 36, another embodiment of a process for applying the additive composition to only one side of a base web in accordance with the present disclosure is shown. Like reference numerals have been used to indicate similar elements.

The process illustrated in FIG. 36 is similar to the process illustrated in FIG. 8. In the process shown in FIG. 36, however, the additive composition is indirectly applied to the base web 80 by an offset printing apparatus in an offset printing arrangement.

For instance, as shown in FIG. 36, the additive composition 106 is first transferred to a first print roll 102. From the print roll 102, the additive composition is then transferred to an analog roll 103 prior to being applied to the base web 80. From the analog roll 103, the additive composition is pressed onto the base web 80 through the assistance of a rubber backing roll 100.

Similar to FIG. 8, once the additive composition is applied to the base web 80, the web is then adhered to a heated creping drum 108 and creped from the drum using a creping blade 112 prior to being wound into a roll 116.

Figure 37:
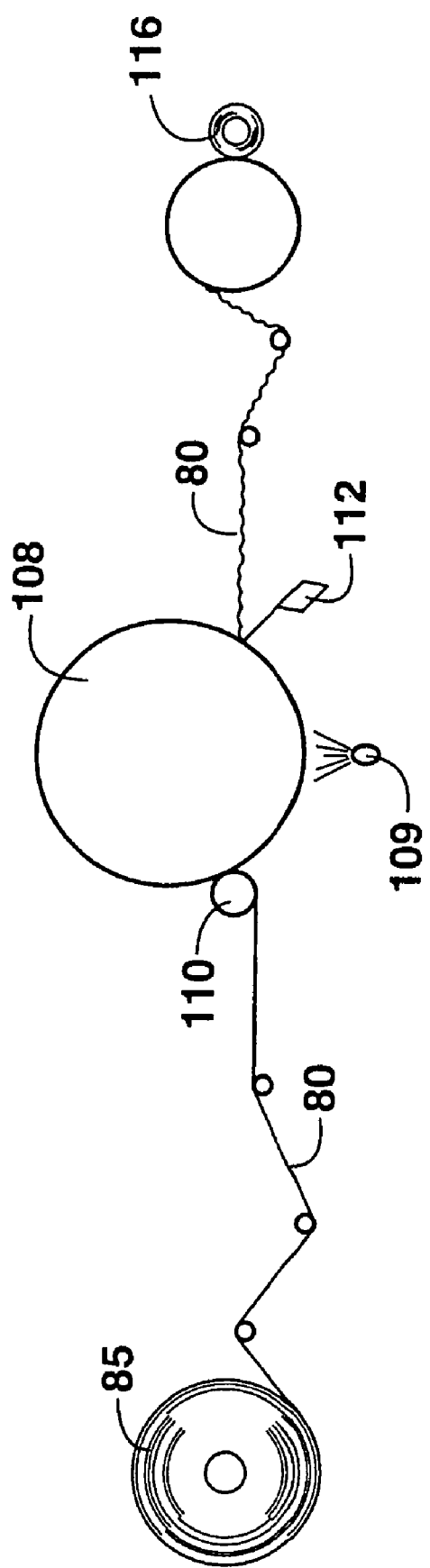
FIG. 37 is a schematic diagram of still another embodiment of a process for applying an additive composition to one side of a base web and creping one side of the web in accordance with the present disclosure.

Referring to FIG. 37, still another embodiment of a process for applying the additive composition to only one side of the base web in accordance with the present disclosure is illustrated. As shown, in this embodiment, a formed base web 80 is unwound from a roll 85 and fed into the process. This process may be considered an off-line process, although the application method may also be installed in-line.

As illustrated in FIG. 37, the dried base web 80 is pressed against a dryer drum 108 by a press roll 110. A spray device 109 applies the additive composition of the present disclosure to the surface of the dryer drum. The additive composition thus not only adheres the base web 80 to the surface of the dryer drum 108, but also transfers to the base web as the web is creped from the drum using a creping blade 112. Once creped from the dryer drum 108, the base web 80 is wound into a roll 116.

The embodiment illustrated in FIG. 37 may be considered a spray crepe process. During the process, the dryer drum 108 can be heated to temperatures as described above with respect to the other embodiments illustrated in the figures.

When only treating one side of the base web 80 with an additive composition, in one embodiment, it may be desirable to apply the additive composition according to a pattern that covers greater than about 40% of the surface area of one side of the web. For instance, the pattern may cover from about 40% to about 90% of the surface area of one side of the web such as from about 40% to about 60%. In one particular example, for instance, the additive composition can be applied according to the pattern shown in FIG. 7.

In one specific embodiment of the present disclosure, a two-ply product is formed from a first paper web and a second paper web in which both paper webs are generally made according to the process shown in FIG. 8. For instance, a first paper web made according to the present disclosure can be attached to a second paper web made according to the present disclosure in a manner such that the creped sides of the webs form the exterior surfaces of the resulting product. The creped surfaces are generally softer and smoother creating a two-ply product having improved overall characteristics.

The manner in which the first paper web is laminated to the second paper web may vary depending upon the particular application and desired characteristics. In some applications, the alpha-olefin interpolymer of the present disclosure may serve as the ply-bonding agent. In other applications, a binder material, such as an adhesive or binder fibers, is applied to one or both webs to join the webs together. The adhesive can be, for instance, a latex adhesive, a starch-based adhesive, an acetate such as an ethylene-vinyl acetate adhesive, a polyvinyl alcohol adhesive, and the like. It should be understood, however, that other binder materials, such as thermoplastic films and fibers can also be used to join the webs. The binder material may be spread evenly over the surfaces of the web in order to securely attach the webs together or may be applied at selected locations.

In addition to wet lay processes as shown in FIGS. 2 and 3, it should be understood that various other base sheets may be treated in accordance with the present disclosure. For instance, other base sheets that may be treated in accordance with the present disclosure include airlaid webs, coform webs, and hydroentangled webs. When treating these types of base sheets, the additive composition is generally topically applied to the base sheets. For instance, the additive composition can be sprayed or printed onto the surface of the base sheet.

Airlaid webs are formed in an air forming process in which a fibrous nonwoven layer is created. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air or a spray adhesive. The production of airlaid nonwoven composites is well defined in the literature and documented in the art. Examples include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

Other materials containing cellulosic fibers include coform webs and hydroentangled webs. In the coform process, at least one meltblown diehead is arranged near a chute through which other materials are added to a meltblown web while it is forming. Such other materials may be natural fibers, superabsorbent particles, natural polymer fibers (for example, rayon) and/or synthetic polymer fibers (for example, polypropylene or polyester), for example, where the fibers may be of staple length.

Coform processes are shown in commonly assigned U.S. Pat. Nos. 4,818,464 to Lau and 4,100,324 to Anderson et al., which are incorporated herein by reference. Webs produced by the coform process are generally referred to as coform materials. More particularly, one process for producing coform nonwoven webs involves extruding a molten polymeric material through a die head into fine streams and attenuating the streams by converging flows of high velocity, heated gas (usually air) supplied from nozzles to break the polymer streams into discontinuous microfibers of small diameter. The die head, for instance, can include at least one straight row of extrusion apertures. In general, the microfibers may have an average fiber diameter of up to about 10 microns. The average diameter of the microfibers can be generally greater than about 1 micron, such as from about 2 microns to about 5 microns. While the microfibers are predominantly discontinuous, they generally have a length exceeding that normally associated with staple fibers.

In order to combine the molten polymer fibers with another material, such as pulp fibers, a primary gas stream is merged with a secondary gas stream containing the individualized wood pulp fibers. Thus, the pulp fibers become integrated with the polymer fibers in a single step. The wood pulp fibers can have a length of from about 0.5 millimeters to about 10 millimeters. The integrated air stream is then directed onto a forming surface to air form the nonwoven fabric. The nonwoven fabric, if desired, may be passed into the nip of a pair of vacuum rolls in order to further integrate the two different materials.

Natural fibers that may be combined with the meltblown fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Cellulose Fibers Incorporated of Axis, Ala.

When containing cellulosic materials such as pulp fibers, a coform material may contain the cellulosic material in an amount from about 10% by weight to about 80% by weight, such as from about 10% by weight to about 49% by weight. For example, in one embodiment, a coform material may be produced containing pulp fibers in an amount from about 30% by weight to about 45% by weight.

In addition to coform webs, hydroentangled webs can also contain synthetic and pulp fibers. Hydroentangled webs refer to webs that have been subjected to columnar jets of a fluid that cause the fibers in the web to entangle. Hydroentangling a web typically increases the strength of the web. In one embodiment, pulp fibers can be hydroentangled into a continuous filament material, such as a spunbond web. The hydroentangled resulting nonwoven composite may contain pulp fibers in an amount from about 10% to about 80% by weight, such as in an amount of about 45% by weight. Commercially available hydroentangled composite webs as described above are commercially available from the Kimberly-Clark Corporation under the name HYDROKNIT. Hydraulic entangling is described in, for example, U.S. Pat. No. 5,389,202 to Everhart, which is incorporated herein by reference.

The present disclosure may be better understood with reference to the following examples.

EXAMPLE 1

To illustrate the properties of wiping products made in accordance with the present disclosure, various tissue samples were treated with an additive composition and subjected to standardized tests. For purposes of comparison, an untreated tissue sample, a tissue sample treated with a silicone composition, and a tissue sample treated with an ethylene vinyl acetate binder were also tested.

More particularly, the tissue samples comprised tissue sheets containing three plies. Each ply of the three ply tissue samples was formed in a process similar to that shown in FIG. 3. Each ply had a basis weight of about 13.5 gsm. More specifically, each ply was made from a stratified fiber furnish containing a center layer of fibers positioned between two outer layers of fibers. The outer layers of each ply contained eucalyptus kraft pulp, obtained from Aracruz with offices in Miami, Fla., USA. Each of the two outer layers was approximately 33% of the total fiber weight of the sheet. The center layer, which was approximately 34% of the total fiber weight of the sheet, was comprised of 100% of northern softwood kraft pulp, obtained from Neenah Paper Inc. with offices in Alpharetta, Ga., USA. The three plies were attached together such that the tissue sides pressed on the dryer faced the outside surfaces of the 3-ply tissue sample.

The 3-ply tissue sheets were coated with additive compositions made according to the present disclosure. A second set of samples were coated with a silicone composition, while a third set of samples were coated with an ethylene vinyl acetate copolymer.

The tissue sheets were coated with the above compositions using a rotogravure printer. The tissue web was fed into the rubber-rubber nip of the rotogravure printer to apply the above compositions to both sides of the web. The gravure rolls were electronically engraved, chrome over copper rolls supplied by Specialty Systems, Inc., Louisville, Ky. The rolls had a line screen of 200 cells per lineal inch and a volume of 8.0 Billion Cubic Microns (BCM) per square inch of roll surface. Typical cell dimensions for this roll were 140 microns in width and 33 microns in depth using a 130 degree engraving stylus. The rubber backing offset applicator rolls were a 75 shore A durometer cast polyurethane supplied by Amerimay Roller company, Union Grove, Wis. The process was set up to a condition having 0.375 inch interference between the gravure rolls and the rubber backing rolls and 0.003 inch clearance between the facing rubber backing rolls. The simultaneous offset/offset gravure printer was run at a speed of 150 feet per minute using gravure roll speed adjustment (differential) to meter the above compositions to obtain the desired addition rate. The process yielded an add-on level of 6.0 weight percent total add-on based on the weight of the tissue (3.0% each side).

For samples treated with additive compositions made in accordance with the present disclosure, the following table provides the components of the additive composition for each sample. In the table below, AFFINITY™ EG8200 plastomer is an alpha-olefin interpolymer comprising an ethylene and octene copolymer that was obtained from The Dow Chemical Company of Midland, Mich., U.S.A. PRIMACOR™ 5980i copolymer is an ethylene-acrylic acid copolymer also obtained from The Dow Chemical Company. The ethylene-acrylic acid copolymer can serve not only as a thermoplastic polymer but also as a dispersing agent. INDUSTRENE® 106 comprises oleic acid, which is marketed by Chemtura Corporation, Middlebury, Conn. The polymer designated as "PBPE" is an experimental propylene-based plastomer or elastomer ("PBPE") having a density of 0.867 grams/cm$^3$ as measured by ASTM D792, a melt flow rate of 25 g/10 min. at 230° C. at 2.16 kg as measured by ASTM D1238, and an ethylene content of 12% by weight of the PBPE. These PBPE materials are taught in WO03/040442 and U.S. application 60/709,688 (filed Aug. 19, 2005), each of which is hereby incorporated by reference in its entirety. AFFINITY™ PL1280 plastomer is an alpha-olefin intepolymer comprising an ethylene and octene copolymer that was also obtained from The Dow Chemical Company. UNICID® 350 dispersing agent is a linear, primary carboxylic acid-functionalized surfactant with the hydrophobe comprising an average 26-carbon chain obtained from Baker-Petrolite Inc., Sugar Land, Tex., U.S.A. AEROSOL® OT-100 dispersing agent is a dioctyl sodium sulfosuccinate obtained from Cytec Industries, Inc., of West Paterson, N.J., U.S.A. PRIMACOR™ 5980i copolymer contains 20.5% by weight acrylic acid and has a melt flow rate of 13.75 g/10 min at 125° C. and 2.16 kg as measured by ASTM D1238. AFFINITY™ EG8200G plastomer has a density of 0.87 g/cc as measured by ASTM D792 and has a melt flow rate of 5 g/10 min at 190° C. and 2.16 kg as measured by ASTM D1238. AFFINITY™ PL1280G plastomer, on the other hand, has a density of 0.90 g/cc as measured by ASTM D792 and has a melt flow rate of 6 g/10 min at 190° C. and 2.16 kg as measured by ASTM D1238.

The additive composition in each of the samples also contained DOWICIL™ 200 antimicrobial obtained from The Dow Chemical Company, which is a preservative with the active composition of 96%c is 1-(3-chloroallyl)-3,5,7-triaza-1-azoniaadamantane chloride (also known as Quaternium-15).

| Sample No. | Polymer (wt. ratios in parentheses) | Dispersing Agent | Dispersing Agent conc. (wt. %) |
|---|---|---|---|
| 1 | AFFINITY ™ EG8200 | Unicid ® 350 | 3.0 |
| 2 | AFFINITY ™ EG8200/PRIMACOR ™ 5980i (70/30) | PRIMACOR ™ 5980i | 30.0 |
| 3 | PBPE | Unicid ® 350/AEROSOL ® OT-100 | 3.0/2.5 |
| 4 | PBPE/PRIMACOR ™ 5980i (70/30) | PRIMACOR ™ 5980i | 30.0 |
| 5 | AFFINITY ™ EG8200/AFFINITY ™ PL1280 (80/20) | Unicid ® 350/Industrene ® 106 | 2.0/2.0 |
| 6 | AFFINITY ™ EG8200/AFFINITY ™ PL1280 (50/50) | Unicid ® 350/Industrene ® 106 | 2.0/2.0 |
| 7 | AFFINITY ™ EG8200/PRIMACOR ™ 5980i (75/25) | PRIMACOR ™ 5980i/Industrene ® 106 | 25.0/3.0 |
| 8 | AFFINITY ™ EG8200/PRIMACOR ™ 5980i (90/10) | PRIMACOR ™ 5980i | 10.0 |
| 9 | AFFINITY ™ EG8200/PRIMACOR ™ 5980i (75/25) | PRIMACOR ™ 5980i/Industrene ® 106 | 25.0/3.0 |
| 10 | AFFINITY ™ EG8200/PRIMACOR ™ 5980i (60/40) | PRIMACOR ™ 5980i/Industrene ® 106 | 40.0/6.0 |
| 11 | AFFINITY ™ EG8200/PRIMACOR ™ 5980i (75/25) | PRIMACOR ™ 5980i/Industrene ® 106 | 25.0/3.0 |
| 12 | AFFINITY ™ EG8200/PRIMACOR ™ 5980i (90/10) | PRIMACOR ™ 5980i/Industrene ® 106 | 10.0/6.0 |
| 13 | AFFINITY ™ EG8200/PRIMACOR ™ 5980i (90/10) | PRIMACOR ™ 5980i | 10.0 |
| 14 | AFFINITY ™ EG8200/PRIMACOR ™ 5980i (60/40) | PRIMACOR ™ 5980i/Industrene ® 106 | 40.0/6.0 |
| 15 | AFFINITY ™ EG8200/PRIMACOR ™ 5980i (75/25) | PRIMACOR ™ 5980i/Industrene ® 106 | 25.0/3.0 |
| 16 | AFFINITY ™ EG8200/PRIMACOR ™ 5980i (90/10) | PRIMACOR ™ 5980i | 10.0 |
| 17 | AFFINITY ™ EG8200/PRIMACOR ™ 5980i (75/25) | PRIMACOR ™ 5980i/Industrene ® 106 | 25.0/3.0 |
| 18 | AFFINITY ™ EG8200/PRIMACOR ™ 5980i (90/10) | PRIMACOR ™ 5980i/Industrene ® 106 | 10.0/6.0 |
| 19 | AFFINITY ™ EG8200/PRIMACOR ™ 5980i (60/40) | PRIMACOR ™ 5980i | 40.0 |
| 20 | AFFINITY ™ EG8200/PRIMACOR ™ 5980i (60/40) | PRIMACOR ™ 5980i | 40.0 |
| 21 | AFFINITY ™ EG8200/PRIMACOR ™ 5980i (60/40) | PRIMACOR ™ 5980i/Industrene ® 106 | 40.0/6.0 |

| Sample No. | Polymer Particle size (um) | Poly-dispersity | Solids (wt. %) | pH | Viscosity (cp) | Temp (° C.) | RPM | Spindle |
|---|---|---|---|---|---|---|---|---|
| 1 | 1.08 | 1.83 | 54.7 | 10.0 | 83 | 22 | 50 | RV2 |
| 2 | 1.48 | 2.40 | 41.0 | 10.5 | 338 | 20 | 50 | RV3 |
| 3 | 0.72 | 1.42 | 55.5 | 10.2 | 626 | 21.1 | 50 | RV3 |
| 4 | 0.85 | 2.06 | 42.8 | 10.2 | 322 | 21.5 | 50 | RV3 |
| 5 | 0.86 | 1.68 | 55.2 | 9.7 | 490 | 55.0 | 50 | RV3 |
| 6 | 1.08 | 1.85 | 52.4 | 10.9 | 296 | 21.7 | 50 | RV3 |
| 7 | 1.86 | 4.46 | 50.1 | 9.4 | 538 | 21.1 | 50 | RV3 |
| 8 | 5.55 | 2.67 | 49.3 | 9.0 | <75 | 21.6 | 100 | RV3 |
| 9 | 1.18 | 2.48 | 46.1 | 10.5 | 270 | 21.2 | 50 | RV3 |
| 10 | 1.60 | 1.58 | 41.1 | 8.7 | 368 | 21.7 | 50 | RV3 |
| 11 | 1.69 | 3.68 | 48.8 | 9.7 | 306 | 22.1 | 50 | RV3 |
| 12 | 1.34 | 2.24 | 51.0 | 10.2 | 266 | 21.4 | 50 | RV3 |
| 13 | 1.16 | 2.25 | 46.6 | 10.5 | 85 | 21.5 | 100 | RV3 |
| 14 | 1.01 | 1.57 | 32.1 | 10.3 | 572 | 21.7 | 50 | RV3 |
| 15 | 1.53 | 3.50 | 50.1 | 9.9 | 396 | 22.3 | 50 | RV3 |
| 16 | 9.86 | 4.14 | 51.2 | 8.7 | <75 | 21.5 | 50 | RV3 |
| 17 | 1.57 | 3.26 | 49.8 | 9.9 | 436 | 22.4 | 50 | RV3 |
| 18 | 0.89 | 1.51 | 51.1 | 12.3 | 342 | 21.5 | 50 | RV3 |
| 19 | 0.71 | 2.12 | 40.0 | 11.3 | 448 | 22.1 | 50 | RV3 |
| 20 | 1.63 | 2.23 | 42.0 | 8.6 | 178 | 22.0 | 100 | RV3 |
| 21 | 1.49 | 1.87 | 39.0 | 10.3 | 210 | 20.2 | 50 | RV3 |

For comparative reasons, the following samples were also prepared:

| Sample ID | Composition Applied to the Sample |
|---|---|
| Non-Inventive Sample No. 1 | Untreated |
| Non-Inventive Sample No. 2 | Product No. Y-14868 Emulsified Silicone obtained from G.E. Silicones |
| Non-Inventive Sample No. 3 | AIRFLEX ® 426 Binder comprising a carboxylated vinyl acetate-ethylene terpolymer emulsion obtained from Air Products, Inc. |
| Non-Inventive Sample No. 4 | ELVAX ® 3175 Binder comprising an ethylene vinyl acetate copolymer obtained from E. I. DuPont de Nemours of Wilmington, Delaware having a 28% vinyl acetate content. The ethylene vinyl acetate copolymer was combined with UNICID 425, which is a carboxylic acid-functionalized surfactant with a hydrophobe comprising an average 32-carbon chain obtained from Baker-Petrolite, Inc. of Sugarland, Texas. |

The following tests were conducted on the samples:

Tensile Strength, Geometric Mean Tensile Strength (GMT), and Geometric Mean Tensile Energy Absorbed (GMTEA):

The tensile test that was performed used tissue samples that were conditioned at 23° C.+/−1° C. and 50% +/−2% relative humidity for a minimum of 4 hours. The 2-ply samples were cut into 3 inch wide strips in the machine direction (MD) and cross-machine direction (CD) using a precision sample cutter model JDC 15M-10, available from Thwing-Albert Instruments, a business having offices located in Philadelphia, Pa., U.S.A.

The gauge length of the tensile frame was set to four inches. The tensile frame was an Alliance RT/1 frame run with TestWorks 4 software. The tensile frame and the software are available from MTS Systems Corporation, a business having offices located in Minneapolis, Minn., U.S.A.

A 3" strip was then placed in the jaws of the tensile frame and subjected to a strain applied at a rate of 25.4 cm per minute until the point of sample failure. The stress on the tissue strip is monitored as a function of the strain. The calculated outputs included the peak load (grams-force/3", measured in grams-force), the peak stretch (%, calculated by dividing the elongation of the sample by the original length of the sample and multiplying by 100%), the % stretch @ 500 grams-force, the tensile energy absorption (TEA) at break (grams-force*cm/cm$^2$, calculated by integrating or taking the area under the stress-strain curve up the point of failure where the load falls to 30% of its peak value), and the slope A (kilograms-force, measured as the slope of the stress-strain curve from 57-150 grams-force).

Each tissue code (minimum of five replicates) was tested in the machine direction (MD) and cross-machine direction (CD). Geometric means of the tensile strength and tensile energy absorption (TEA) were calculated as the square root of the product of the machine direction (MD) and the cross-machine direction (CD). This yielded an average value that is independent of testing direction. The samples that were used are shown below.

Elastic Modulus (Maximum Slope) and Geometric Mean Modulus (GMM) as Measures of Sheet Stiffness:

Elastic Modulus (Maximum Slope) $E(kg_f)$ is the elastic modulus determined in the dry state and is expressed in units of kilograms of force. Tappi conditioned samples with a width of 3 inches are placed in tensile tester jaws with a gauge length (span between jaws) of 4 inches. The jaws move apart at a crosshead speed of 25.4 cm/min and the slope is taken as the least squares fit of the data between stress values of 57 grams of force and 150 grams of force. If the sample is too weak to sustain a stress of at least 200 grams of force without failure, an additional ply is repeatedly added until the multi-ply sample can withstand at least 200 grams of force without failure. The geometric mean modulus or geometric mean slope was calculated as the square root of the product of the machine direction (MD) and the cross direction (CD) elastic moduli (maximum slopes), yielding an average value that is independent of testing direction.

The results of the testing are graphically illustrated in FIGS. 9 through 14. As shown by the results, the additive composition of the present disclosure improved the geometric mean tensile strength of the samples and the geometric mean total energy absorbed of the samples without significantly impacting sheet stiffness in comparison to the untreated sample and the sample treated with the silicone composition. Further, the ratio of geometric mean modulus to geometric mean tensile for the samples treated with additive compositions made according to the present disclosure showed similar characteristics in comparison to the sample treated with the ethylene vinyl acetate copolymer binder. It was noticed, however, that the sheet blocking characteristics of the samples treated with the additive compositions were much better in relation to the sample treated with the ethylene vinyl acetate copolymer.

In addition to the results shown in the figures, subjective softness testing was also performed on the samples. The perceived softness of the samples treated with the additive compositions of the present disclosure were equivalent to the perceived softness of the sample treated with the silicone composition.

EXAMPLE 2

In this example, additive compositions made according to the present disclosure were printed onto an uncreped through-air dried (UCTAD) base web according to a pattern and creped from a creping drum. The additive composition was used to adhere the base web to the drum. The samples were then tested and compared to an uncreped through-air dried base web that was not subjected to a print creping process (Non-inventive Sample No. 1) and to an uncreped through-air dried base web that was subjected to a similar print crepe process using an ethylene vinyl acetate copolymer (Non-inventive Sample No. 2).

The uncreped through-air dried base web was formed in a process similar to the process shown in FIG. 2. The basesheet had a basis weight of about 50 gsm. More specifically, the basesheet was made from a stratified fiber furnish containing a center layer of fibers positioned between two outer layers of fibers. Both outer layers of the basesheet contained 100% northern softwood kraft pulp. One outer layer contained about 10.0 kilograms (kg)/metric ton (Mton) of dry fiber of a debonding agent (ProSoft® TQ1003 from Hercules, Inc.). The other outer layer contained about 5.0 kilograms (kg)/metric ton (Mton) of dry fiber of a dry and wet strength agent (KYMENE® 6500, available from Hercules, Incorporated, located in Wilmington, Del., U.S.A.). Each of the outer layers comprised about 30% of the total fiber weight of the sheet. The center layer, which comprised about 40% of the total fiber weight of the sheet, was comprised of 100% by weight of northern softwood kraft pulp. The fibers in this layer were also treated with 3.75 kg/Mton of ProSoft® TQ1003 debonder.

Various samples of the basesheet were then subjected to a print creping process. The print creping process is generally illustrated in FIG. 8. The sheet was fed to a gravure printing line where the additive composition was printed onto the surface of the sheet. One side of the sheet was printed using direct rotogravure printing. The sheet was printed with a 0.020 diameter "dot" pattern as shown in FIG. 5 wherein 28 dots per inch were printed on the sheet in both the machine and cross-machine directions. The resulting surface area coverage was approximately 25%. The sheet was then pressed against and doctored off a rotating drum, causing the sheet temperature to range from about 180° F. to 390° F., such as from about 200° F. to 250° F. Finally the sheet was wound into a roll. Thereafter, the resulting print/print/creped sheet was converted into rolls of single-ply paper toweling in a conventional manner. The finished product had an air dry basis weight of approximately 55.8 gsm.

As described above, for comparative purposes, one sample was subjected to a similar print creping process using AIRFLEX® 426 binder obtained from Air Products, Inc. of Allentown, Pa. AIRFLEX® 426 is a flexible, non-crosslinking carboxylated vinyl acetate-ethylene terpolymer emulsion.

The additive compositions that were applied to the different samples are listed in the following tables. In the tables, AFFINITY™ EG8200 plastomer comprises an interpolymer of an ethylene and octene copolymer, while PRIMACOR™ 5980i comprises an ethylene acrylic acid copolymer. INDUSTRENE® 106 comprises an oleic acid. All three components were obtained from The Dow Chemical Company.

| Sample No | Polymer (wt. ratios in parentheses) | Dispersing Agent | Dispersing Agent conc. (wt. %) |
|---|---|---|---|
| 1 | AFFINITY ™ EG8200/PRIMACOR ™ 5980i (60/40) | PRIMACOR ™ 5980i/Industrene ® 106 | 40.0/6.0 |
| 2 | AFFINITY ™ EG8200/PRIMACOR ™ 5980i (60/40) | PRIMACOR 5980i ™/Industrene ® 106 | 40.0/6.0 |
| 3 | AFFINITY ™ EG8200/PRIMACOR ™ 5980i (60/40) | PRIMACOR 5980i ™ | 40.0 |
| 4 | AFFINITY ™ EG8200/PRIMACOR ™ 5980i (60/40) | PRIMACOR 5980i ™ | 40.0 |

| Sample No | Polymer Particle size (um) | Poly-dispersity | Solids (wt. %) | pH | Viscosity (cp) | Temp (° C.) | RPM | Spindle |
|---|---|---|---|---|---|---|---|---|
| 1 | 1.60 | 1.58 | 41.1 | 8.7 | 368 | 21.7 | 50 | RV3 |
| 2 | 1.01 | 1.57 | 32.1 | 10.3 | 572 | 21.7 | 50 | RV3 |
| 3 | 0.71 | 2.12 | 40.0 | 11.3 | 448 | 22.1 | 50 | RV3 |
| 4 | 1.63 | 2.23 | 42.0 | 8.6 | 178 | 22.0 | 100 | RV3 |

DOWICIL™ 200 antimicrobial, which is a preservative with the active composition of 96% cis 1-(3-chloroallyl)-3,5,7-triaza-1-azoniaadamantane chloride (also known as Quaternium-15) obtained from The Dow Chemical Company was also present in each of the additive compositions.

The samples were subjected to the tests described in Example 1. In addition, the following test was also conducted on the samples.

Wet/Dry Tensile Test (% in the Cross Machine Direction)

The dry tensile test is described in Example 1, with the gauge length (span between jaws) being 2 inches. Wet tensile strength was measured in the same manner as dry strength except that the samples were wetted prior to testing. Specifically, in order to wet the sample, a 3"×5" tray was filled with distilled or deionized water at a temperature of 23±2° C. The water is added to the tray to an approximate one cm depth.

A 3M "Scotch-Brite" general purpose scrubbing pad is then cut to dimensions of 2.5"×4". A piece of masking tape approximately 5" long is placed along one of the 4" edges of the pad. The masking tape is used to hold the scrubbing pad.

The scrubbing pad is then placed into the water with the taped end facing up. The pad remains in the water at all times until testing is completed. The sample to be tested is placed on blotter paper that conforms to TAPPI T205. The scrubbing pad is removed from the water bath and tapped lightly three times on a screen associated with the wetting pan. The scrubbing pad is then gently placed on the sample parallel to the width of the sample in the approximate center. The scrubbing pad is held in place for approximately one second. The sample is then immediately put into the tensile tester and tested.

To calculate the wet/dry tensile strength ratio, the wet tensile strength value was divided by the dry tensile strength value.

The results obtained are illustrated in FIGS. 15-19. As shown in the figures, the additive compositions improved the geometric mean tensile and the geometric mean total energy absorbed of the tissue samples without significantly impacting sheet stiffness relative to the untreated sample. It was also observed during the testing that the additive compositions did not create sheet blocking problems in comparison to the samples treated with the ethylene vinyl acetate copolymer.

EXAMPLE 3

In this example, tissue webs were made generally according to the process illustrated in FIG. 3. In order to adhere the tissue web to a creping surface, which in this embodiment comprised a Yankee dryer, additive compositions made according to the present disclosure were sprayed onto the dryer prior to contacting the dryer with the web. The samples were then subjected to various standardized tests.

For purposes of comparison, samples were also produced using a standard PVOH/KYMENE crepe package.

In this example, 2-ply tissue products were produced and tested according to the same tests described in Examples 1 and 2. The following process was used to produce the samples.

Initially, 80 pounds of air-dried softwood kraft (NSWK) pulp was placed into a pulper and disintegrated for 15 minutes at 4% consistency at 120 degrees F. Then, the NSWK pulp was refined for 15 minutes, transferred to a dump chest and subsequently diluted to approximately 3% consistency. (Note: Refining fibrillates fibers to increase their bonding potential.) Then, the NSWK pulp was diluted to about 2% consistency and pumped to a machine chest, such that the machine chest contained 20 air-dried pounds of NSWK at about 0.2-0.3% consistency. The above softwood fibers were utilized as the inner strength layer in a 3-layer tissue structure.

Two kilograms KYMENE® 6500, available from Hercules, Incorporated, located in Wilmington, Del., U.S.A., per metric ton of wood fiber and two kilograms per metric ton of wood fiber PAREZ® 631 NC, available from LANXESS Corporation., located in Trenton, N.J., U.S.A., was added and allowed to mix with the pulp fibers for at least 10 minutes before pumping the pulp slurry through the headbox.

Forty pounds of air-dried Aracruz ECF, a eucalyptus hardwood Kraft (EHWK) pulp available from Aracruz, located in Rio de Janeiro, RJ, Brazil, was placed into a pulper and disintegrated for 30 minutes at about 4% consistency at 120 degrees Fahrenheit. The EHWK pulp was then transferred to a dump chest and subsequently diluted to about 2% consistency.

Next, the EHWK pulp slurry was diluted, divided into two equal amounts, and pumped at about 1% consistency into two separate machine chests, such that each machine chest contained 20 pounds of air-dried EHWK. This pulp slurry was subsequently diluted to about 0.1% consistency. The two EHWK pulp fibers represent the two outer layers of the 3-layered tissue structure.

Two kilograms KYMENE® 6500 per metric ton of wood fiber was added and allowed to mix with the hardwood pulp fibers for at least 10 minutes before pumping the pulp slurry through the headbox.

The pulp fibers from all three machine chests were pumped to the headbox at a consistency of about 0.1%. Pulp fibers from each machine chest were sent through separate manifolds in the headbox to create a 3-layered tissue structure. The fibers were deposited on a forming fabric. Water was subsequently removed by vacuum.

The wet sheet, about 10-20% consistency, was transferred to a press felt or press fabric where it was further dewatered. The sheet was then transferred to a Yankee dryer through a nip via a pressure roll. The consistency of the wet sheet after the pressure roll nip (post-pressure roll consistency or PPRC) was approximately 40%. The wet sheet adhered to the Yankee dryer due to an adhesive that is applied to the dryer surface. Spray booms situated underneath the Yankee dryer sprayed either an adhesive package, which is a mixture of polyvinyl alcohol/KYMENE®/Rezosol 2008M, or an additive composition according to the present disclosure onto the dryer surface. Rezosol 2008M is available from Hercules, Incorporated, located in Wilmington, Del., U.S.A.

One batch of the typical adhesive package on the continuous handsheet former (CHF) typically consisted of 25 gallons of water, 5000 mL of a 6% solids polyvinyl alcohol solution, 75 mL of a 12.5% solids KYMENE® solution, and 20 mL of a 7.5% solids Rezosol 2008M solution.

The additive compositions according to the present disclosure varied in solids content from 2.5% to 10%.

The sheet was dried to about 95% consistency as it traveled on the Yankee dryer and to the creping blade. The creping blade subsequently scraped the tissue sheet and small amounts of dryer coating off the Yankee dryer. The creped tissue basesheet was then wound onto a 3" core into soft rolls for converting. Two rolls of the creped tissue were then rewound and plied together so that both creped sides were on the outside of the 2-ply structure. Mechanical crimping on the edges of the structure held the plies together. The plied sheet was then slit on the edges to a standard width of approximately 8.5 inches and folded. Tissue samples were conditioned and tested.

The additive compositions of the present disclosure that were applied to the samples and tested in this example are as follows:

| Sample No. | Polymer (wt. ratios in parentheses) | Dispersing Agent | Dispersing Agent conc. (wt. %) | % Solids |
|---|---|---|---|---|
| 1 | AFFINITY ™ EG8200/PRIMACOR ™ 5980i (60/40) | PRIMACOR ™ 5980i/Industrene ® 106 | 40.0/6.0 | 2.5 |
| 2 | AFFINITY ™ EG8200/PRIMACOR ™ 5980i (60/40) | PRIMACOR ™ 5980i | 40.0 | 2.5 |
| 3 | AFFINITY ™ EG8200/PRIMACOR ™ 5980i (60/40) | PRIMACOR ™ 5980i/Industrene ® 106 | 40.0/6.0 | 5 |
| 4 | AFFINITY ™ EG8200/PRIMACOR ™ 5980i (60/40) | PRIMACOR ™ 5980i | 40.0 | 5 |
| 5 | AFFINITY ™ EG8200/PRIMACOR ™ 5980i (60/40) | PRIMACOR ™ 5980i/Industrene ® 106 | 40.0/6.0 | 10 |

| Sample No | Polymer Particle size (um) | Poly-dispersity | Solids (wt. %) | pH | Viscosity (cp) | Temp (° C.) | RPM | Spindle |
|---|---|---|---|---|---|---|---|---|
| 1 | 1.01 | 1.57 | 32.1 | 10.3 | 572 | 21.7 | 50 | RV3 |
| 2 | 0.71 | 2.12 | 40.0 | 11.3 | 448 | 22.1 | 50 | RV3 |
| 3 | 1.01 | 1.57 | 32.1 | 10.3 | 572 | 21.7 | 50 | RV3 |
| 4 | 0.71 | 2.12 | 40.0 | 11.3 | 448 | 22.1 | 50 | RV3 |
| 5 | 1.01 | 1.57 | 32.1 | 10.3 | 572 | 21.7 | 50 | RV3 |

DOWICIL™ 200 antimicrobial, which is a preservative with the active composition of 96% cis 1-(3-chloroallyl)-3,5,7-triaza-1-azoniaadamantane chloride (also known as Quaternium-15) obtained from The Dow Chemical Company, was also present in each of the additive compositions.

As shown above, the percent solids in solution for the different additive compositions was varied. Varying the solids content in solution also varies the amount of solids incorporated into the base web. For instance, at 2.5% solution solids, it is estimated that from about 35 kg/MT to about 60 kg/MT solids is incorporated into the tissue web. At 5% solution solids, it is estimated that from about 70 kg/MT to about 130 kg/MT solids is incorporated into the tissue web. At 10% solution solids, it is estimated that from about 140 kg/MT to about 260 kg/MT solids is incorporated into the tissue web.

Figure 20:
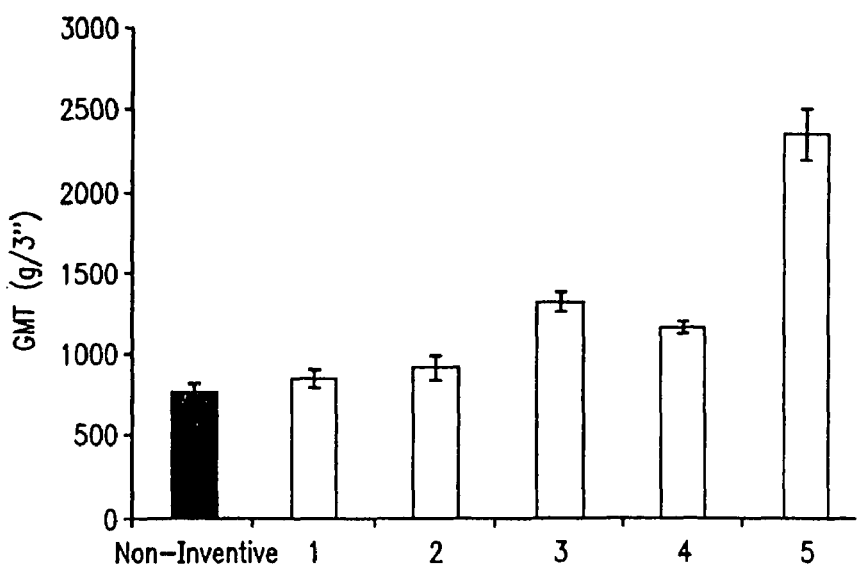
Figure 21:
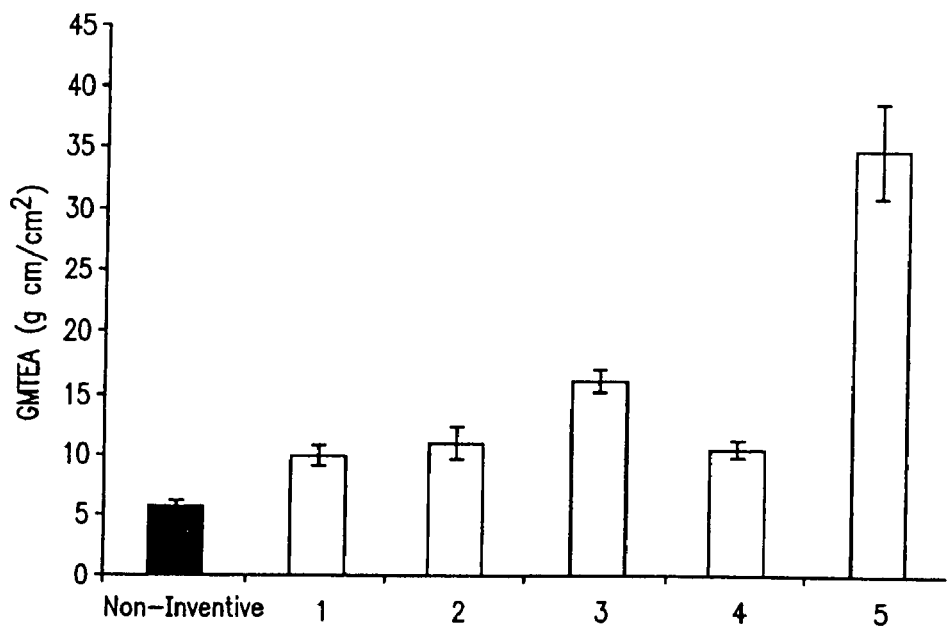
Figure 22:
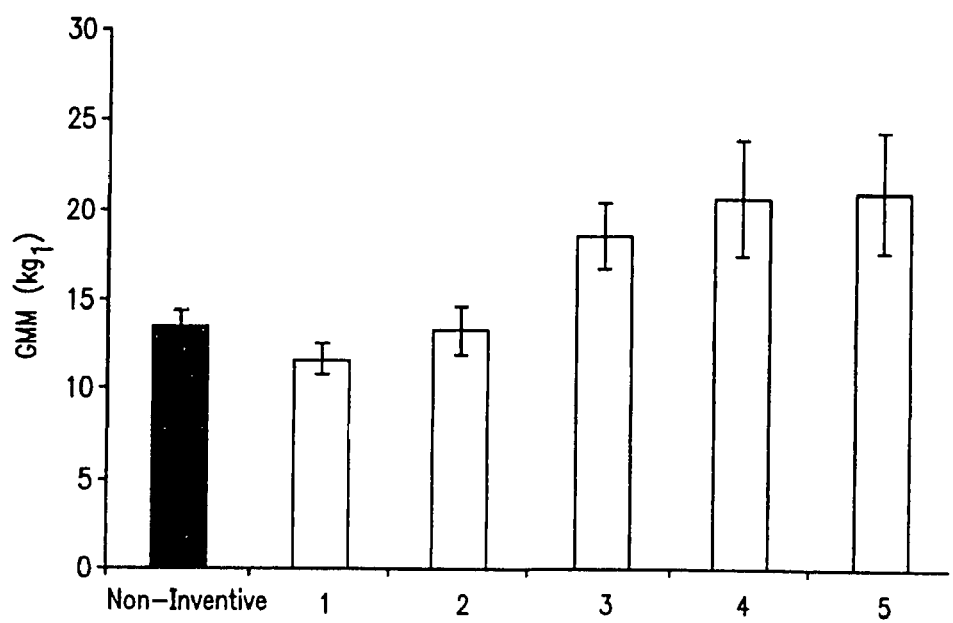
Figure 23:
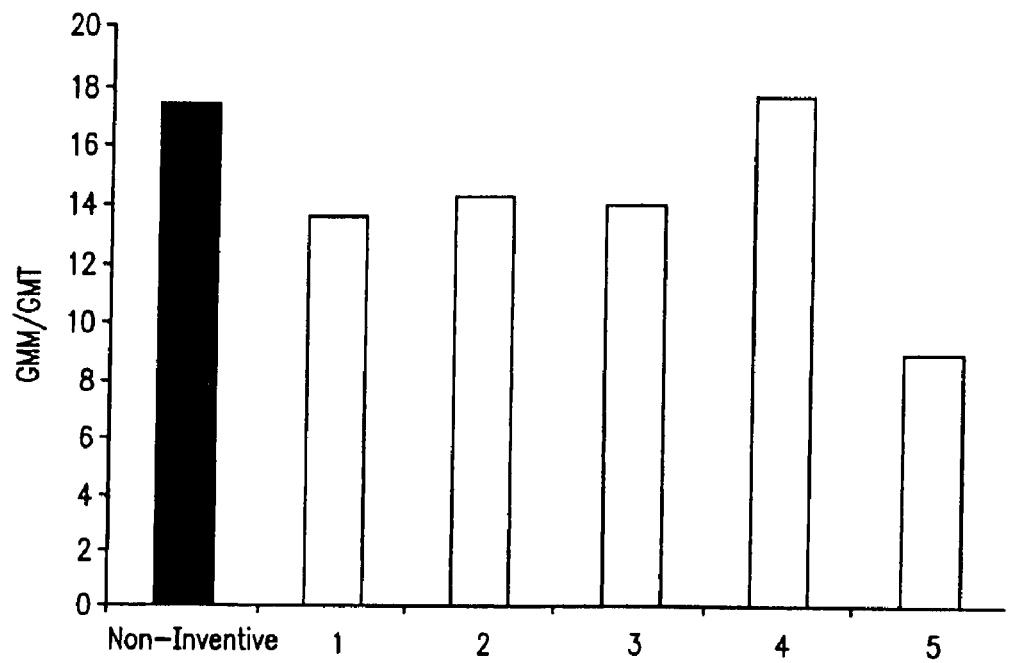
Figure 24:
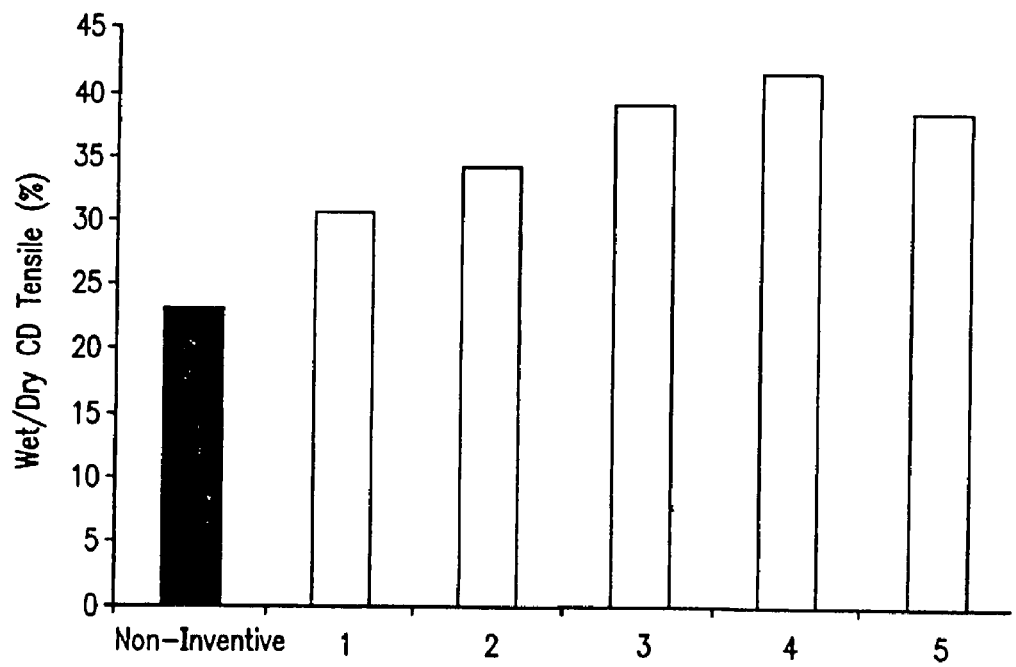

The results of this example are illustrated in FIGS. 20-24. As shown in FIG. 20, for instance, the geometric mean tensile strength of the samples made according to the present disclosure were greater than the non-inventive sample treated with the conventional bonding material. Similar results were also obtained for the geometric mean total energy absorbed.

Figure 25A:
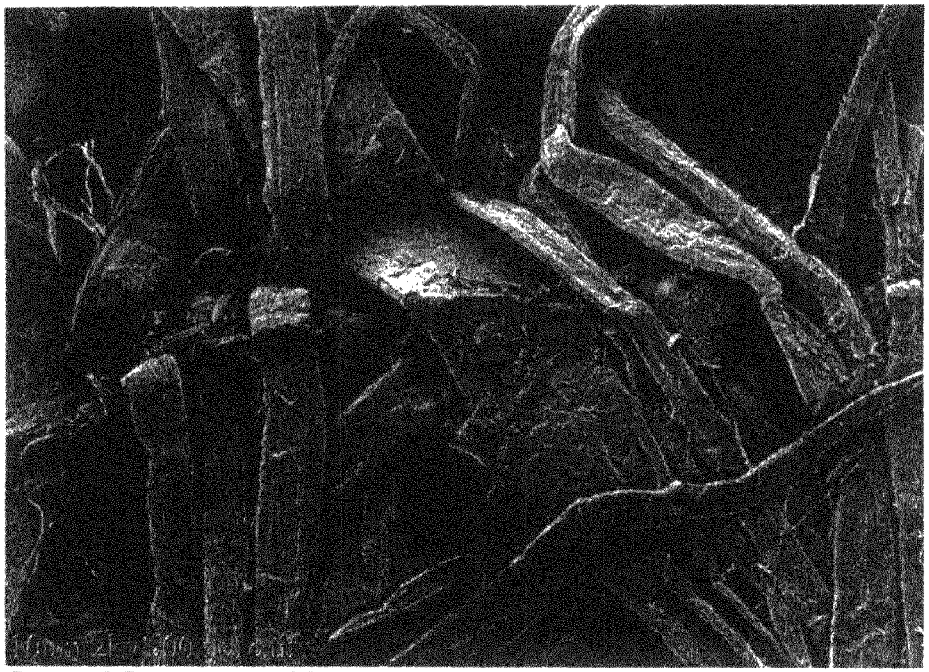
Figure 25B:
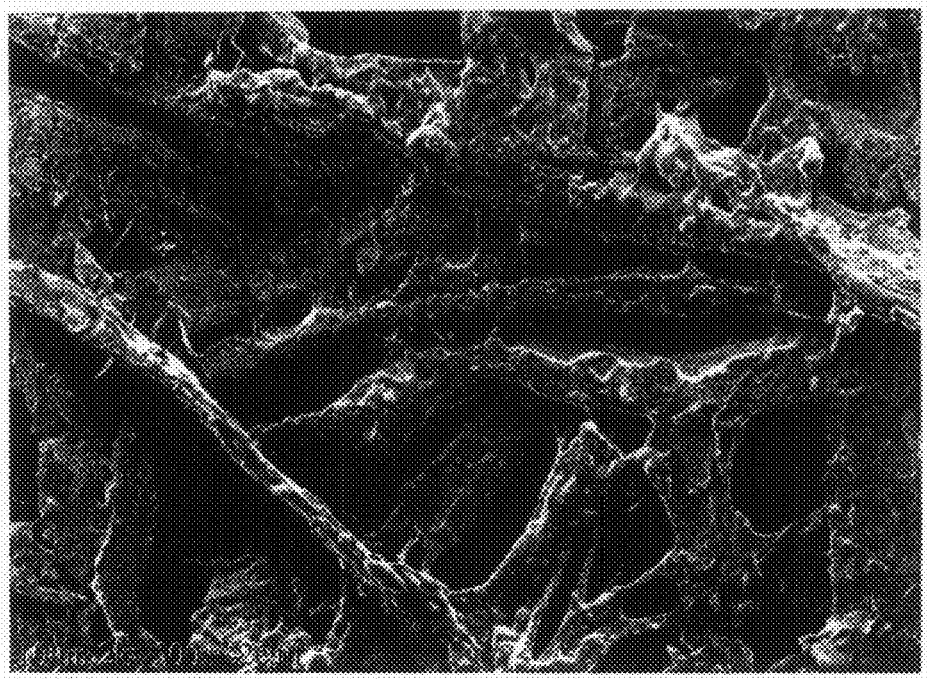
Figure 25C:
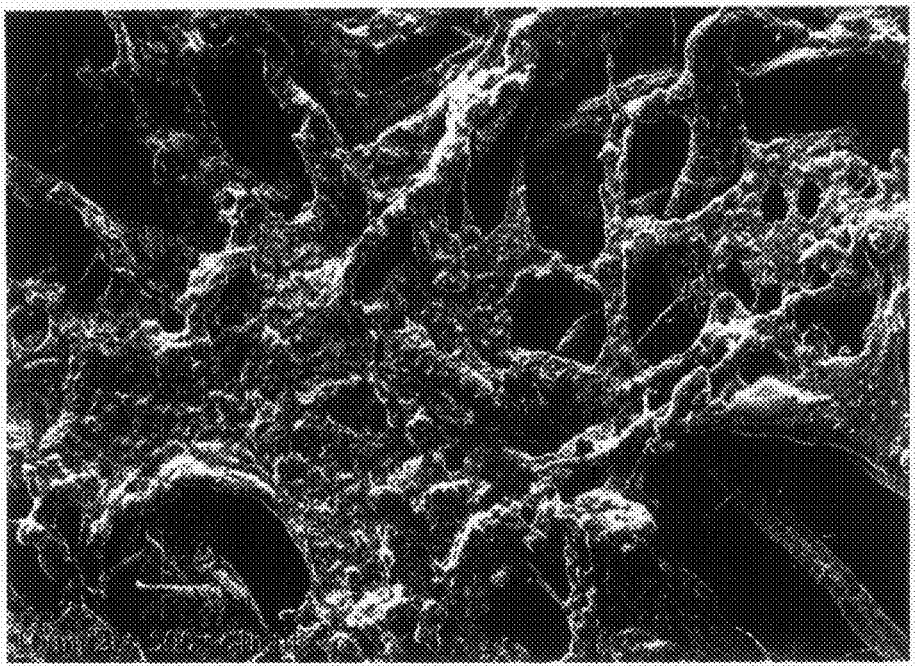
Figure 25D:
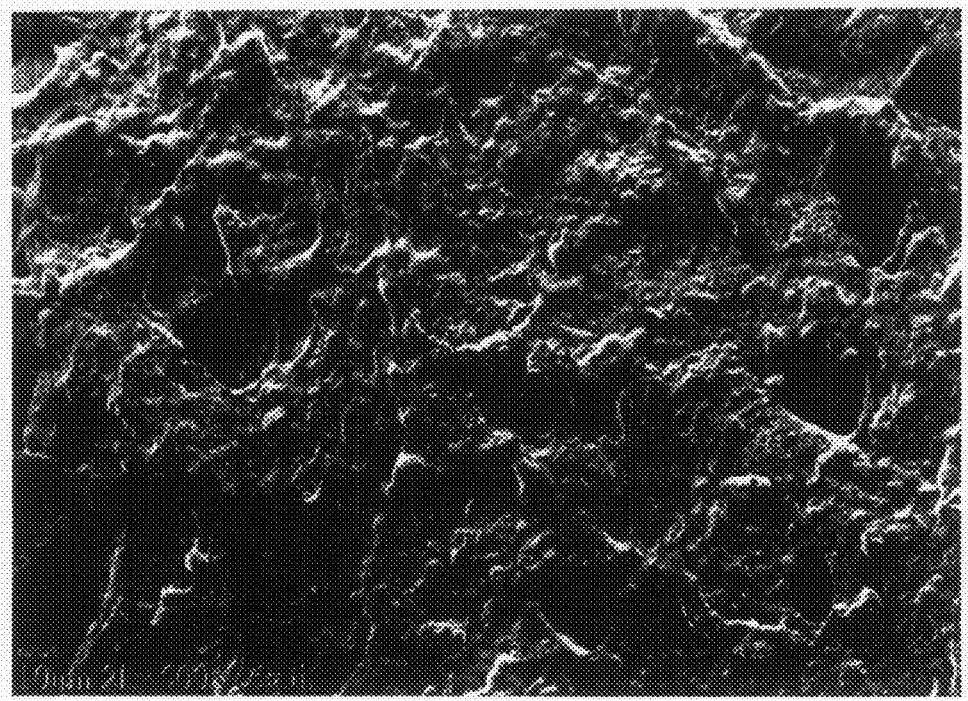

In addition to testing the properties of the samples, some of the samples were also photographed. For instance, referring to FIGS. 25A, 25B, 25C and 25D, four of the samples are shown at 500 times magnification. In particular, FIG. 25A represents a photograph of the non-inventive sample, FIG. 25B is a photograph of Sample No. 1, FIG. 25C is a photograph of Sample No. 3, and FIG. 25D is a photograph of Sample No. 5. As shown, the additive composition of the present disclosure tends to form a discontinuous film over the surface of the tissue web. Further, the greater the solution solids, the greater the amount of film formation. These figures indicate that the additive composition generally remains on the surface of the tissue web.

Figure 26:
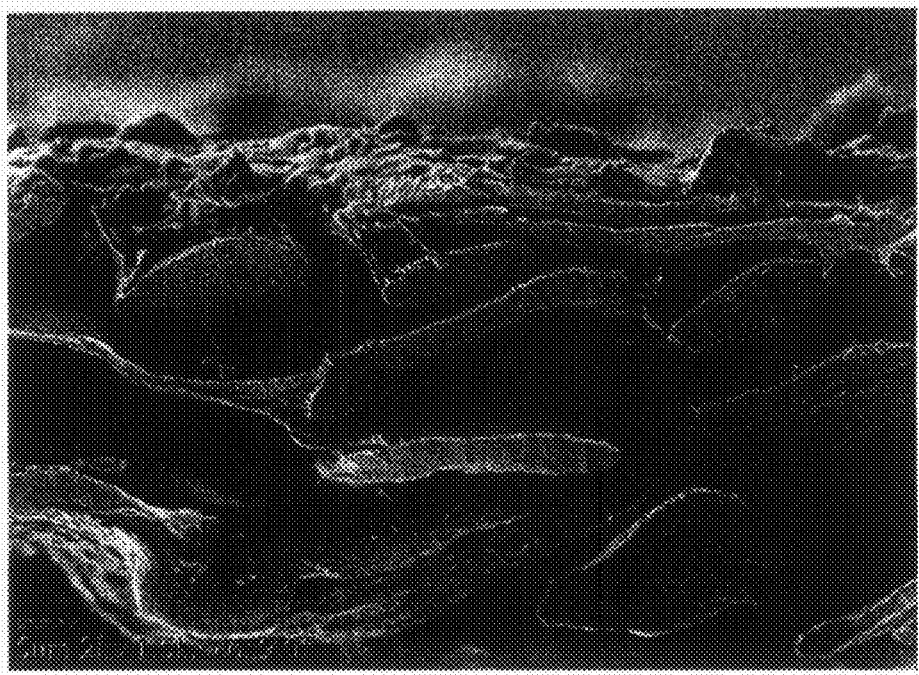

Referring to FIG. 26, a photograph of the cross section of the same sample illustrated in FIG. 25D is shown. As can be seen in the photograph, even at 10% solution solids, most of the additive composition remains on the surface of the tissue web. In this regard, the additive composition penetrates the web in an amount less than about 25% of the thickness of the web, such as less than about 15% of the thickness of the web, such as less than about 5% of the thickness of the web.

In this manner, it is believed that the additive composition provides a significant amount of strength to the tissue web. Further, because the film is discontinuous, the wicking properties of the web are not substantially adversely affected. Of particular advantage, these results are obtained without also a substantial increase in stiffness of the tissue web and without a substantial decrease in the perceived softness.

EXAMPLE 4

In this example, tissue webs made according to the present disclosure were compared to commercially available products. The samples were subjected to various tests. In particular, the samples were subjected to a "Stick-Slip Parameter Test" which measures the perceived softness of the product by measuring the spacial and temporal variation of a drag force as skin simulant is dragged over the surface of the sample.

More particularly, the following tests were performed in this example.

Stick-Slip Test

Stick-slip occurs when the static coefficient of friction ("COF") is significantly higher than the kinetic COF. A sled pulled over a surface by a string will not move until the force in the string is high enough to overcome the static COF times the normal load. However, as soon as the sled starts to move the static COF gives way to the lower kinetic COF, so the pulling force in the string is unbalanced and the sled accelerates until the tension in the string is released and the sled stops (sticks). The tension then builds again until it is high enough to overcome the static COF, and so on. The frequency and amplitude of the oscillations depend upon the difference between the static COF and the kinetic COF, but also upon the length and stiffness of the string (a stiff, short string will let the force drop down almost immediately when the static COF is overcome so that the sled jerks forward only a small distance), and upon the speed of travel. Higher speeds tend to reduce stick-slip behavior.

Static COF is higher than kinetic COF because two surfaces in contact under a load tend to creep and comply with each other and increase the contact area between them. COF is proportional to contact area so more time in contact gives a higher COF. This helps explain why higher speeds give less stick-slip: there is less time after each slip event for the surfaces to comply and for the static COF to rise. For many materials the COF decreases with higher speed sliding because of this reduced time for compliance. However, some materials (typically soft or lubricated surfaces) actually show an increase in COF with increasing speed because the surfaces in contact tend to flow either plastically or viscoelastically and dissipate energy at a rate proportional to the rate at which they are sheared. Materials which have increasing COF with velocity do not show stick-slip because it would take more force to make the sled jerk forward than to continue at a constant slower rate. Such materials also have a static COF equal to their kinetic COF. Therefore, measuring the slope of the COF versus velocity curve is a good means of predicting whether a material is likely to show stick-slip: more negative slopes will stick-slip easily, while more positive slopes will not stick-slip even at very low velocities of sliding.

Figure 27:
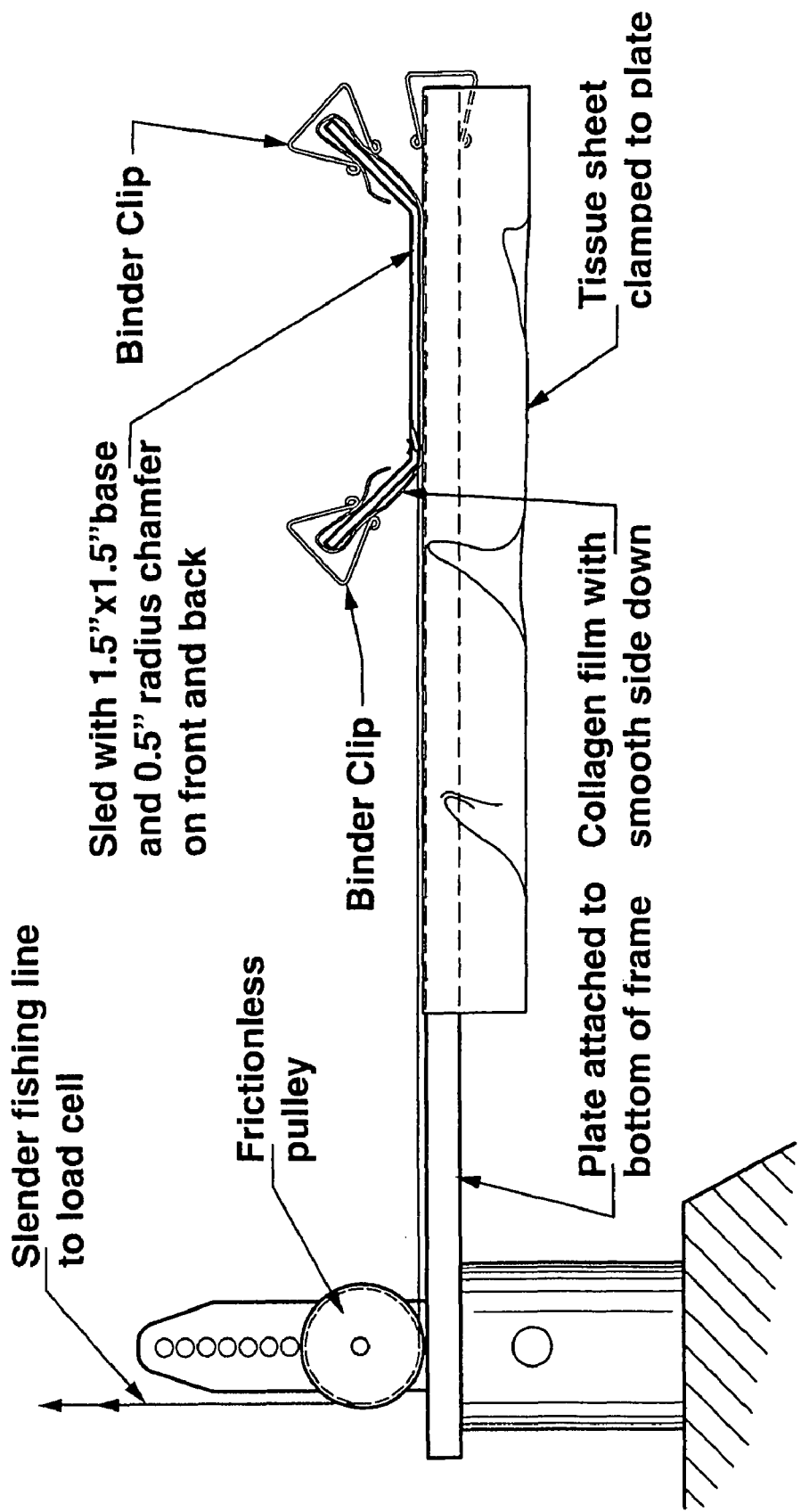
FIG. 27 is a diagram illustrating the equipment used to perform a Stick-Slip Test.

According to the Stick-Slip test, the variation in COF with velocity of sliding is measured using an Alliance RT/1 tensile frame equipped with MTS TestWorks 4 software. A diagram of part of the testing apparatus is shown in FIG. 27. As illustrated, a plate is fixed to the lower part of the frame, and a tissue sheet (the sample) is clamped to this plate. An aluminum sled with a 1.5" by 1.5" flat surface with a ½" radius on the leading and trailing edges is attached to the upper (moving part) of the frame by means of a slender fishing line (30 lb, Stren clear monofilament from Remington Arms Inc, Madison, N.C.) lead though a nearly frictionless pulley up to a 50 N load cell. A 50.8 mm wide sheet of collagen film is clamped flat to the underside of the sled by means of 32 mm binder clips on the front and back of the sled. The total mass of the sled, film and clips is 81.1 g. The film is larger than the sled so that it fully covers the contacting surfaces. The collagen film may be obtained from NATURIN GmbH, Weinhein, Germany, under the designation of COFFI (Collagen Food Film), having a basis weight of 28 gsm. Another suitable film may be obtained from Viscofan USA Inc, 50 County Court, Montgomery Ala. 36105. The films are embossed with a small dot pattern. The flatter side of the film (with the dots dimpled down) should be facing down toward the tissue on the sled to maximize contact area between the tissue and collagen.

The samples and the collagen film should be conditioned at 72 F and 50% RH for at least 6 hours prior to testing.

The tensile frame is programmed to drag the sled at a constant velocity (V) for a distance of 1 cm while the drag force is measured at a frequency of 100 hz. The average drag force measured between 0.2 cm and 0.9 cm is calculated, and kinetic COF is calculated as:

$$COF_V = \frac{f}{81.1} \quad (1)$$

Where f is the average drag force in grams, and 81.1 g is the mass of the sled, clips and film.

For each sample the COF is measured at 5, 10, 25, 50 and 100 cm/min. A new piece of collagen film is used for each sample.

The COF varies logarithmically with velocity, so that the data is described by the expression:

$$COF = a + SSP \ln(V)$$

Where a is the best fit COF at 1 cm/min and SSP is the Stick-Slip Parameter, showing how the COF varies with velocity. A higher value of SSP indicates a more lotiony, less prone to stick-slip sheet. SSP is measured for four tissue sheet samples for each code and the average is reported.

Hercules Size Test (HST)

The "Hercules Size Test" (HST) is a test that generally measures how long it takes for a liquid to travel through a tissue sheet. Hercules size testing was done in general accordance with TAPPI method T 530 PM-89, Size Test for Paper with Ink Resistance. Hercules Size Test data was collected on a Model HST tester using white and green calibration tiles and the black disk provided by the manufacturer. A 2% Napthol Green N dye diluted with distilled water to 1% was used as the dye. All materials are available from Hercules, Inc., Wilmington, Del.

All specimens were conditioned for at least 4 hours at 23+/−1 C and 50+/−2% relative humidity prior to testing. The test is sensitive to dye solution temperature so the dye solution should also be equilibrated to the controlled condition temperature for a minimum of 4 hours before testing.

Six (6) tissue sheets as commercially sold (18 plies for a 3-ply tissue product, 12 plies for a two-ply product, 6 plies for a single ply product, etc.) form the specimen for testing. Specimens are cut to an approximate dimension of 2.5×2.5 inches. The instrument is standardized with white and green calibration tiles per the manufacturer's directions. The specimen (12 plies for a 2-ply tissue product) is placed in the sample holder with the outer surface of the plies facing outward. The specimen is then clamped into the specimen holder. The specimen holder is then positioned in the retaining ring on top of the optical housing. Using the black disk, the instrument zero is calibrated. The black disk is removed and 10+/−0.5 milliliters of dye solution is dispensed into the retaining ring and the timer started while placing the black disk back over the specimen. The test time in seconds (sec.) is recorded from the instrument.

Extraction Method for Determining Additive Content in Tissue

One method for measuring the amount of additive composition in a tissue sample is removal of the additive composition in a suitable solvent. Any suitable solvent may be selected, provided that it can dissolve at least a majority of the additive present in the tissue. One suitable solvent is Xylene.

To begin, a tissue sample containing the additive composition (3 grams of tissue minimum per test) was placed in an oven set at 105° C. overnight to remove all water. The dried tissue was then sealed in a metal can with a lid and allowed to cool in a dessicator containing calcium sulfate dessicant to prevent absorption of water from the air. After allowing the sample to cool for 10 minutes, the weight of the tissue was measured on a balance with an accuracy of ±0.0001 g. and the weight recorded ($W_1$).

The extraction was performed using a soxhlet extraction apparatus. The soxhlet extraction apparatus consisted of a 250 ml glass round bottom flask connected to a soxhlet extraction tube (Corning® no. 3740-M, with a capacity to top of siphon of 85 ml) and an Allihn condenser (Corning® no. 3840-MCO). The condenser was connected to a fresh cold water supply. The round bottom flask was heated from below using an electrically heated mantle (Glas Col, Terre Haute, Ind. USA) controlled by a variable auto transformer (Superior Electric Co., Bristol, Conn. USA).

To conduct an extraction, the pre-weighed tissue containing the additive composition was placed into a 33 mm×80 mm cellulose extraction thimble (Whatman International Ltd, Maidstone, England). The thimble was then put into the soxhlet extraction tube and the tube connected to the round bottom flask and the condenser. Inside the round bottom flask was 150 ml of xylene solvent. The heating mantle was energized and water flow through the condenser was initiated. The variable auto transformer heat control was adjusted such that the soxhlet tube filled with xylene and cycled back into the round bottom flask every 15 minutes. The extraction was conducted for a total of 5 hours (approximately 20 cycles of xylene through the soxhlet tube). Upon completion the thimble containing the tissue was removed from the soxhlet tube and allowed to dry in a hood. The tissue was then transported to an oven set at 150° C. and dried for 1 hour to remove excess xylene solvent. This oven was vented to a hood. The dry tissue was then placed in an oven set at 105° C. overnight. The next day the tissue was removed, placed in a metal can with a lid, and allowed to cool in a desiccator containing calcium sulfate desiccant for 10 minutes. The dry, cooled extracted tissue weight was then measured on a balance with an accuracy of ±0.0001 g. and the weight recorded ($W_2$).

The % xylene extractives was calculated using the equation below:

$$\text{\% xylene extractives} = 100 \times (W_1 - W_2) \div W_1$$

Because not all of the additive composition may extract in the selected solvent, it was necessary to construct a calibration curve to determine the amount of additive composition in an unknown sample. A calibration curve was developed by first applying a known amount of additive to the surface of a pre-weighed tissue ($T_1$) using an air brush. The additive composition was applied evenly over the tissue and allowed to dry in an oven at 105° C. overnight. The weight of the treated tissue was then measured ($T_2$) and the weight % of additive was calculated using the equation below:

$$\text{\% additive} = 100 \times (T_2 - T_1) \div T_1$$

Treated tissues over a range of additive composition levels from 0% to 13% were produced and tested using the soxhlet extraction procedure previously described. The linear regression of % xylene extractives (Y variable) vs. % additive (X variable) was used as the calibration curve.

$$\text{Calibration curve: \% xylene extractives} = m(\text{\% additive}) + b$$

$$\text{or: \% additive} = (\text{\% xylene extractives} - b)/m$$

where: m=slope of linear regression equation
b=y-intercept of linear regression equation After a calibration curve has been established, the additive composition of a tissue sample can be determined. The xylene extractives content of a tissue sample was measured using the soxhlet extraction procedure previously described. The % additive in the tissue was then calculated using the linear regression equation:

$$\text{\% additive} = (\text{\% xylene extractives} - b)/m$$

where: m=slope of linear regression equation
b=y-intercept of linear regression equation A minimum of two measurements were made on each tissue sample and the arithmetic average was reported as the % additive content.

Dispersibility-Slosh Box Measurements

The slosh box used for the dynamic break-up of the samples consists of a 14"W×18"D×12" H plastic box constructed from 0.5" thick Plexiglas with a tightly fitting lid. The box rests on a platform, with one end attached to a hinge and the other end attached to a reciprocating cam. The amplitude of the rocking motion of the slosh box is ±2" (4" range). The speed of the sloshing action is variable but was set to a constant speed of 20 revolutions per minute of the cam, or 40 sloshes per minute. A volume of 2000 mL of either the "tap water" or "soft water" soak solution was added to the slosh box before testing. The tap water solution can contain about 112 ppm $HCO_3^-$, 66 ppm $Ca^{2+}$, 20 ppm $Mg^{2+}$, 65 ppm $Na^+$, 137 ppm $Cl^-$, 100 ppm $SO_4^{2-}$ with a total dissolved solids of 500 ppm and a calculated water hardness of about 248 ppm equivalents $CaCO_3$. The soft water solution, on the other hand, contains about 6.7 ppm $Ca^{2+}$, 3.3 ppm $Mg^{2+}$, and 21.5 ppm $Cl^-$ with a total dissolved solids of 31.5 ppm and a calculated water hardness of about 30 ppm equivalents $CaCO_3$. A sample was unfolded and placed in the slosh box. The slosh box was started and timing was started once the sample was added to the soak solution. The break-up of the sample in the slosh box was visually observed and the time required for break-up into pieces less than about 1" square in area was recorded. At least three replicates of the samples were recorded and averaged to achieve the recorded values. Sample which do not break-up into pieces less than about 1" square in area within 24 h in a particular soak solution are considered non-dispersible in that soak solution by this test method.

In this example, 14 tissue samples were made according to the present disclosure and subjected to at least one of the above tests and compared to various commercially available tissue products.

The first three samples made according to the present disclosure (Sample Nos. 1, 2 and 3 in the table below) were made generally according to the process described in Example 3 above.

Tissue web samples 4 through 7, on the other hand, were made generally according to the process illustrated in FIG. 3. In order to adhere the tissue web to a creping surface, which in this embodiment comprised a Yankee dryer, additive compositions made according to the present disclosure were sprayed onto the dryer prior to contacting the dryer with the web. Two-ply or three-ply tissue products were produced. The samples were then subjected to various standardized tests.

Initially, softwood kraft (NSWK) pulp was dispersed in a pulper for 30 minutes at 4% consistency at about 100 degrees F. Then, the NSWK pulp was transferred to a dump chest and subsequently diluted to approximately 3% consistency. Then, the NSWK pulp was refined at 4.5 hp-days/metric ton. The above softwood fibers were utilized as the inner strength layer in a 3-layer tissue structure. The NSWK layer contributed approximately 34% of the final sheet weight.

Two kilograms KYMENE® 6500, available from Hercules, Incorporated, located in Wilmington, Del., U.S.A., per metric ton of wood fiber was added to the furnish prior to the headbox.

Aracruz ECF, a eucalyptus hardwood Kraft (EHWK) pulp available from Aracruz, located in Rio de Janeiro, RJ, Brazil, was dispersed in a pulper for 30 minutes at about 4% consistency at about 100 degrees Fahrenheit. The EHWK pulp was then transferred to a dump chest and subsequently diluted to about 3% consistency. The EHWK pulp fibers represent the two outer layers of the 3-layered tissue structure. The EHWK layers contributed approximately 66% of the final sheet weight.

Two kilograms KYMENE® 6500 per metric ton of wood fiber was added to the furnish prior to the headbox.

The pulp fibers from the machine chests were pumped to the headbox at a consistency of about 0.1%. Pulp fibers from each machine chest were sent through separate manifolds in the headbox to create a 3-layered tissue structure. The fibers were deposited onto a felt in a Crescent Former, similar to the process illustrated in FIG. 3.

The wet sheet, about 10-20% consistency, was adhered to a Yankee dryer, traveling at about 2500 fpm, (750 mpm) through a nip via a pressure roll. The consistency of the wet sheet after the pressure roll nip (post-pressure roll consistency or PPRC) was approximately 40%. The wet sheet adhered to the Yankee dryer due to the additive composition that is applied to the dryer surface. Spray booms situated underneath the Yankee dryer sprayed the additive composition, described in the present disclosure, onto the dryer surface at an addition level of 100 to 600 mg/m$^2$.

To prevent the felt from becoming contaminated by the additive composition, and to maintain desired sheet properties, a shield was positioned between the spray boom and the pressure roll.

The sheet was dried to about 95%-98% consistency as it traveled on the Yankee dryer and to the creping blade. The creping blade subsequently scraped the tissue sheet and a portion of the additive composition off the Yankee dryer. The creped tissue basesheet was then wound onto a core traveling at about 1970 fpm (600 mpm) into soft rolls for converting. The resulting tissue basesheet had an air-dried basis weight of 14.2 g/m2. Two or three soft rolls of the creped tissue were then rewound and plied together so that both creped sides were on the outside of the 2- or 3-ply structure. Mechanical crimping on the edges of the structure held the plies together. The plied sheet was then slit on the edges to a standard width of approximately 8.5 inches and folded. Tissue samples were conditioned and tested.

The additive composition that was applied to Sample Nos. 4 through 7 and tested is as follows:

| Polymer (wt. ratios in parentheses) | Dispersing Agent | Dispersing Agent conc. (wt. %) |
|---|---|---|
| AFFINITY ™ EG8200/PRIMACOR ™ 5986 (60/40) | PRIMACOR ™ 5986 | 40.0 |

| Polymer Particle size (um) | Poly-dispersity | Solids (wt. %) | pH | Viscosity (cp) | Temp (° C.) | RPM | Spindle |
|---|---|---|---|---|---|---|---|
| 0.71 | 2.12 | 40.0 | 11.3 | 448 | 22.1 | 50 | RV3 |

DOWICIL™ 75 antimicrobial, which is a preservative with the active composition of 96% cis 1-(3-chloroallyl)-3,5,7-triaza-1-azoniaadamantane chloride (also known as Quaternium-15) obtained from The Dow Chemical Company, was also present in each of the additive compositions.

The percent solids in solution for the different additive compositions was varied to deliver 100 to 600 mg/m² spray coverage on the Yankee Dryer. Varying the solids content in solution also varies the amount of solids incorporated into the base web. For instance, at 100 mg/m2 spray coverage on the Yankee Dryer, it is estimated that about 1% additive composition solids is incorporated into the tissue web. At 200 mg/m2 spray coverage on the Yankee Dryer, it is estimated that about 2% additive composition solids is incorporated into the tissue web. At 400 mg/m2 spray coverage on the Yankee Dryer, it is estimated that about 4% additive composition solids is incorporated into the tissue web.

Sample Nos. 8 through 13, on the other hand, were produced according to the process described in Example No. 2 above.

Tissue Sample No. 14, on the other hand, comprised a 2-ply product. Tissue Sample No. 14 was made similar to the process described in Example 3.

The tissue web, however, was substantially dry prior to being attached to the dryer drum using the additive composition.

Prior to testing, all of the samples were conditioned according to TAPPI standards. In particular, the samples were placed in an atmosphere at 50% relative humidity and 72° F. for at least four hours.

The following results were obtained:

| Sample No. | Identification of Control Samples | # plies | Basis Weight - Bone Dry (gsm) | Basis Weight (gsm) | Additive Composition Coverage (mg/m²) | GMT (g/3") | GMT/Ply | HST (seconds) | xylene extraction add-on (%) | Dispersibility Slosh Box (min) | Stick-Slip Result |
|---|---|---|---|---|---|---|---|---|---|---|---|
| Control 1 | PUFF's Plus (Procter & Gamble) | 2 | | | 0 | | | | | | −0.020 |
| Control 2 | CELEB Glycerin Treated Tissue (Nepia) | 2 | | | 0 | | | | | | −0.019 |
| Control 3 | KLEENEX Ultra (Kimberly-Clark) | 3 | 39.21 | | 0 | 880 | 293 | 65.8 | | | −0.018 |
| Control 4 | PUFFS (Procter & Gamble) | 2 | | | 0 | 672 | 336 | | | | −0.018 |
| Control 5 | KLEENEX Lotion (Kimberly-Clark) | 3 | | | 0 | | | | | | −0.017 |
| Control 6 | KLEENEX (Kimberly-Clark) | 2 | 26.53 | | 0 | 622 | 311 | 1.2 | | | −0.012 |
| Control 7 | COTTONELLE Ultra (Kimberly-Clark) | 2 | | | 0 | | | | | 1.1 | −0.013 |
| Control 8 | ANDREX (Kimberly-Clark) | 2 | | | 0 | | | | | 0.1 | −0.017 |
| Control 9 | CHARMIN Ultra (Procter & Gamble) | 2 | | | 0 | | | | | 1.9 | −0.018 |
| Control 10 | CHARMIN Plus (Procter & Gamble) | 2 | | | 0 | | | | | | −0.018 |
| Control 11 | CHARMIN Giant (Procter & Gamble) | 1 | | | 0 | | | | | | −0.021 |
| 1 | | 2 | | | 2804 | | | 1.5 | 23.8 | | 0.058 |
| 2 | | 2 | | | 701 | 927 | 464 | | 6.8 | | 0.054 |
| 3 | | 2 | | | 1402 | 1170 | 585 | | 13.3 | | 0.070 |
| 4 | | 2 | 27.32 | | 200 | 792 | 396 | 4.1 | 1.2 | | 0.000 |
| 5 | | 2 | 26.89 | | 400 | 775 | 388 | 7 | 4.1 | | 0.016 |
| 6 | | 3 | 39.93 | | 400 | 1067 | 356 | 9.8 | 3.3 | | 0.018 |
| 7 | | 2 | | | 431 | 874 | 437 | | 3.2* | | 0.023 |
| 8 | | 1 | | 42.6 | 822 | 387 | | 0.7 | 3.8 | 0 | 0.001 |
| 9 | | 1 | | 41.7 | 800 | 764 | | | | | 0.018 |
| 10 | | 1 | | 29 | 310 | 1087 | | | | | 0.000 |
| 11 | | 1 | | 31.5 | 355 | 1685 | | | | | −0.002 |
| 12 | | 1 | | 36.6 | 2633 | 500 | | | | | 0.059 |
| 13 | | 1 | | 30.8 | 411 | 563 | | | | 0 | 0.0 |
| 14 | | 2 | | 28 | 411 | 1457 | | 1.2 | 1.4 | 0.5 | −0.006 |

As shown above, the samples made according to the present disclosure had good water absorbency rates as shown by the Hercules Size Test. In particular, samples made according to the present disclosure had an HST of well below 60 seconds, such as below 30 seconds, such as below 20 seconds, such as below 10 seconds. In fact, many of the samples had an HST of less than about 2 seconds.

In addition to being very water absorbent, bath tissue samples made according to the present disclosure even containing the additive composition had good dispersibility characteristics. For instance, as shown, the samples had a dispersibility of less than about 2 minutes, such as less than about 1-½ minutes, such as less than about 1 minute.

Figure 28:
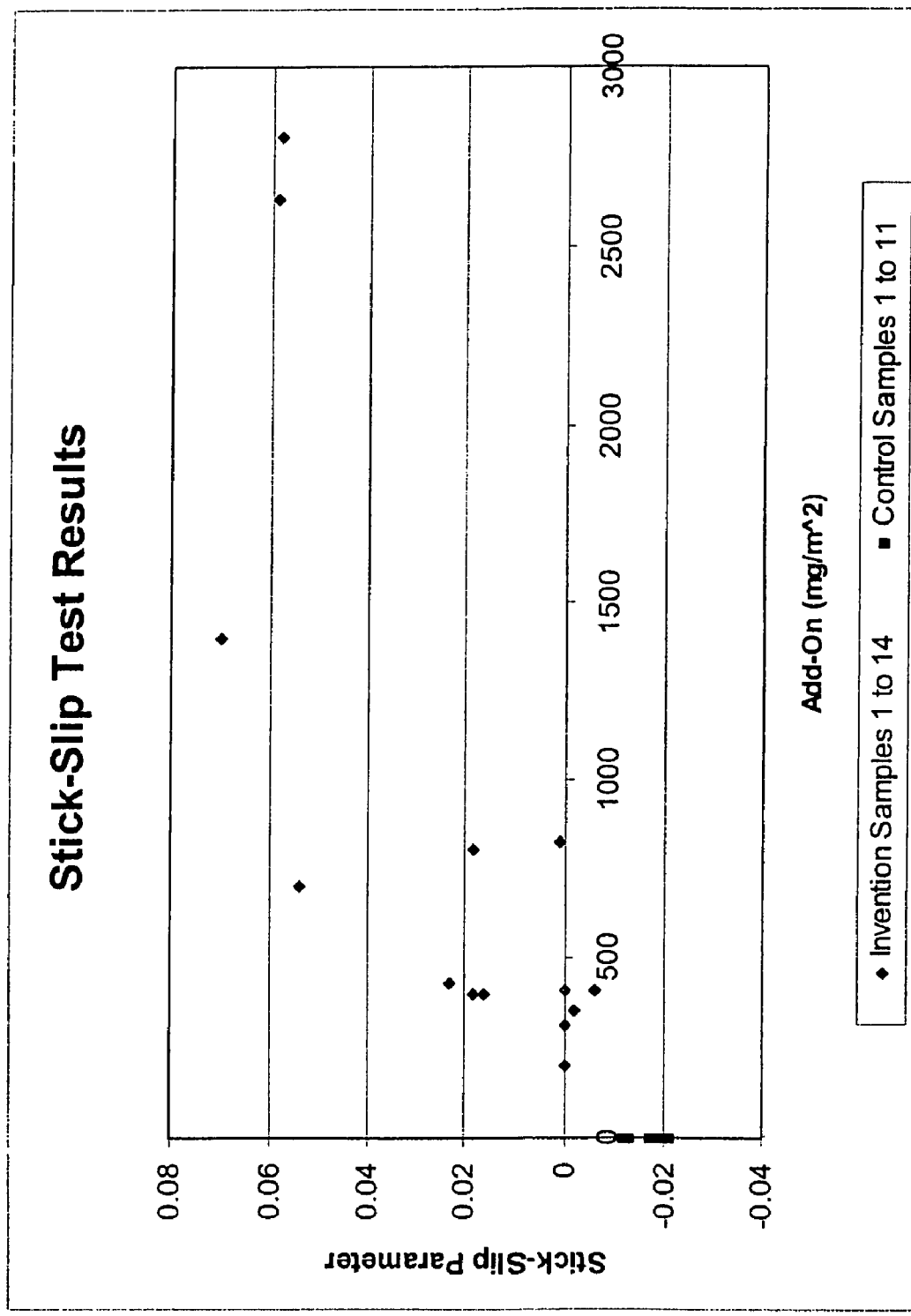

As also shown by the above table, samples made according to the present disclosure had superior stick-slip characteristics. The stick-slip data is also graphically illustrated as FIG. 28. As shown, samples made according to the present disclosure had a stick-slip of from about −0.007 to about 0.1. More particularly, samples made according to the present disclosure had a stick-slip of greater than about −0.006, such as greater than about 0. All of the comparative examples, on the other hand, had lower stick-slip numbers.

EXAMPLE 5

Tissue samples made according to the present disclosure were prepared similar to the process described in Example No. 4 above. In this example, the additive composition was applied to the first sample in a relatively heavy amount and to a second sample in a relatively light amount. In particular, Sample No. 1 contained the additive composition in an amount of 23.8% by weight. Sample No. 1 was made similar to the manner in which Sample No. 1 was produced in Example No. 4 above. Sample No. 2, on the other hand, contained the additive composition in an amount of about 1.2% by weight. Sample No. 2 was made generally in the same manner as Sample No. 4 was made in Example No. 4 above.

After the samples were prepared, one surface of each sample was photographed using a scanning electron microscope.

Figure 29:
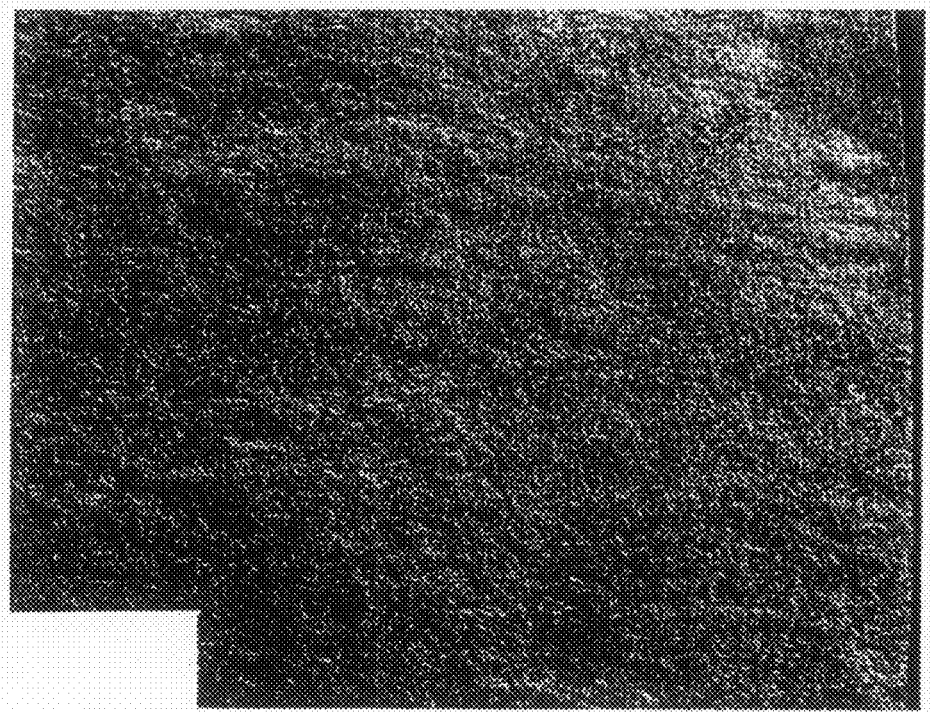
Figure 30:
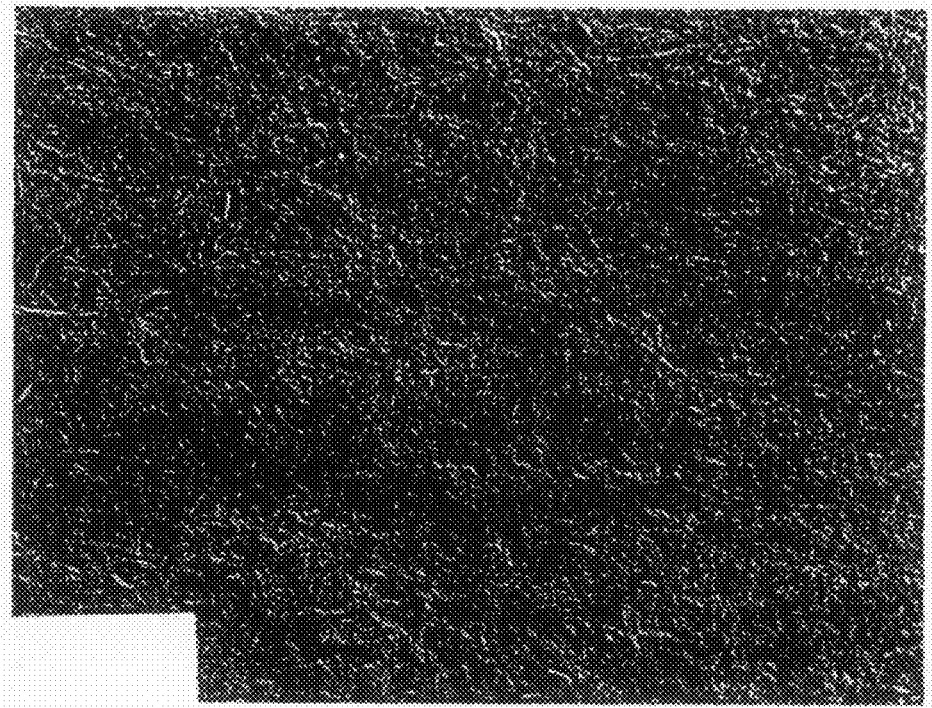
Figure 31:
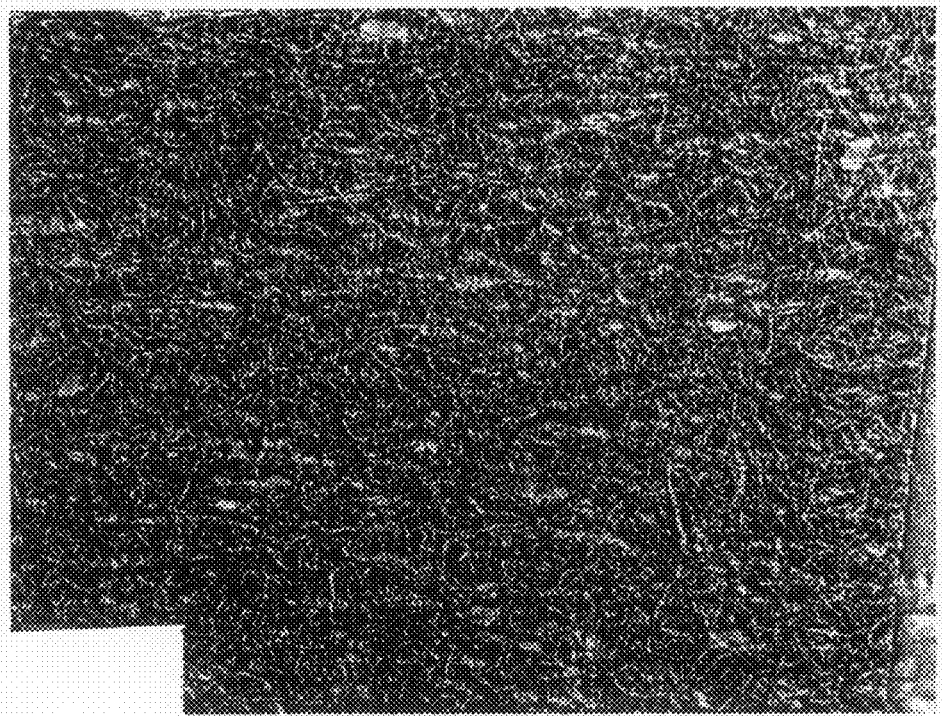
Figure 32:
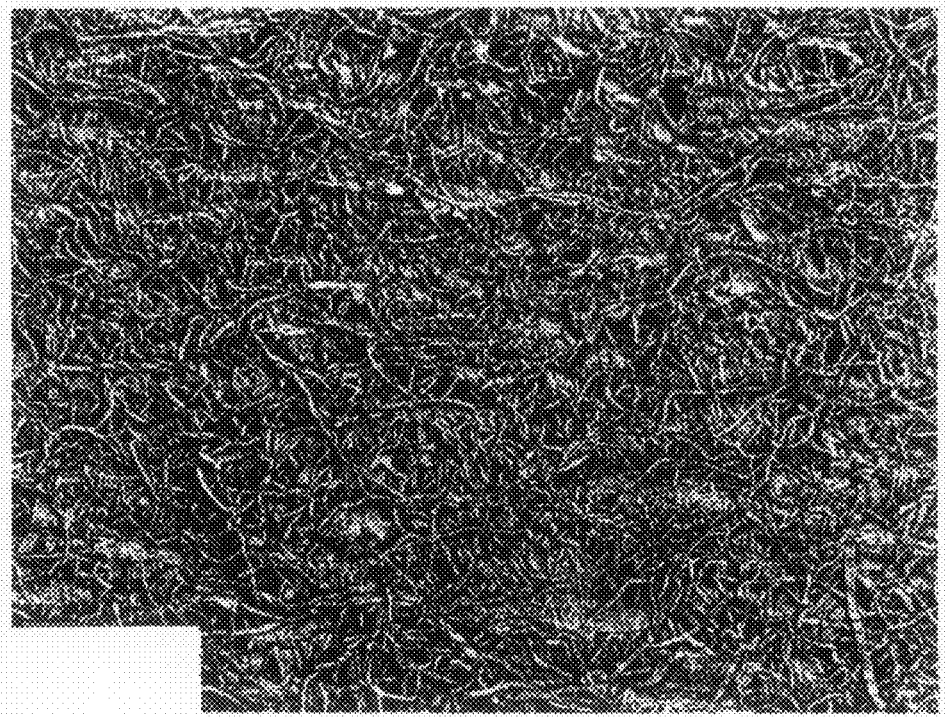
Figure 33:
Figure 34:
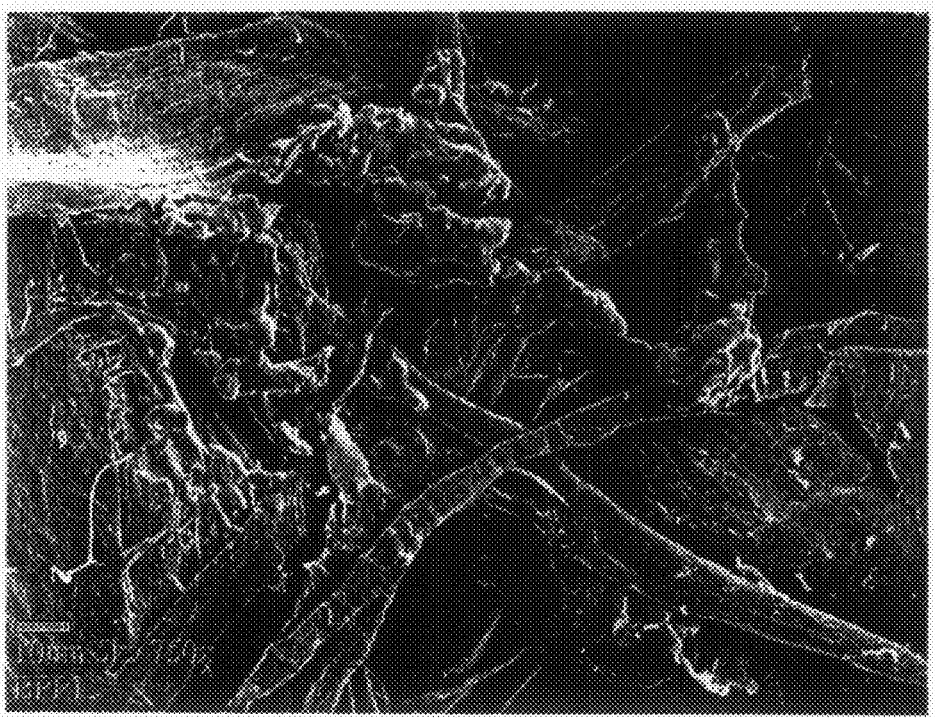

The first sample containing the additive composition in an amount of 23.8% by weight is illustrated in FIGS. 29 and 30. As shown, in this sample, the additive composition forms a discontinuous film over the surface of the product.

FIGS. 31-34, on the other hand, are photographs of the sample containing the additive composition in an amount of about 1.2% by weight. As shown, at relatively low amounts, the additive composition does not form an interconnected network. Instead, the additive composition is present on the surface of the product in discrete and separate areas. Even at the relatively low amounts, however, the tissue product still has a lotiony and soft feel.

EXAMPLE 6

In this example, various compositions were printed onto an uncreped through-air dried (UCTAD) base web according to a pattern and creped from a creping drum. The compositions were used to adhere the base web to the drum.

The samples were then tested for blocking, which refers to the tendency of two adjacent sheets to stick together.

More particularly, the blocking test performed in this example is as follows.

Blocking Test

Figure 38:
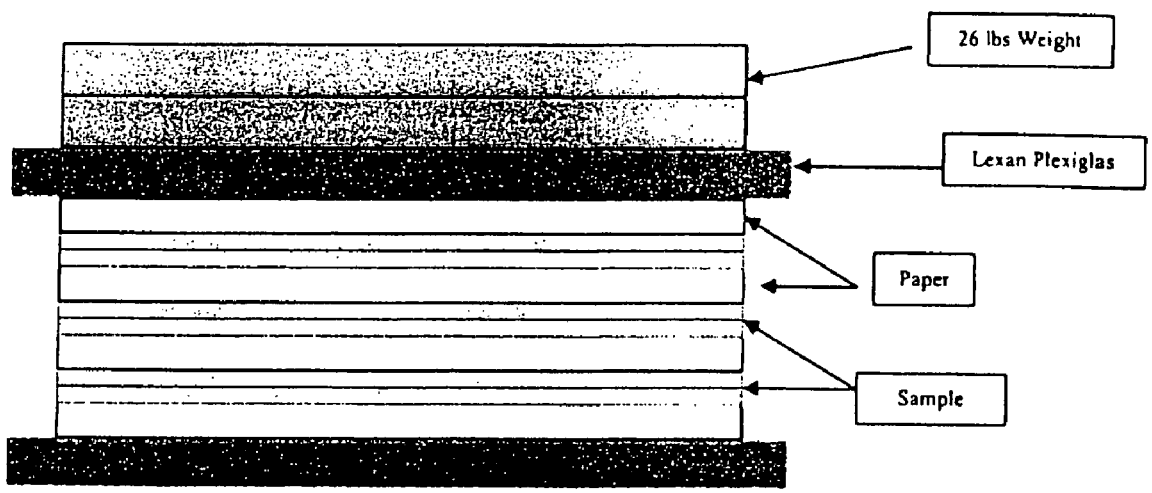
FIG. 38 is a cross sectional view of the sample preparation used to perform a blocking test.

1. Obtain samples of base sheets to be tested. The samples are cut so as to be 3 inches wide and 6 to 7 inches long. The width of the samples is the cross-machine direction while the length is the machine direction of the base sheet.
2. Take two identical samples and place one on top of the other. When testing creped tissue sheets, the uncreped side of each sheet faces upwards. Thus, the uncreped side of the bottom sheet is placed in contact with the creped side of the top sheet.
3. Repeat step 2 above until five samples or stacks have been prepared.
4. Place a piece of LEXAN PLEXIGLAS on a flat surface. The LEXAN PLEXIGLAS has a thickness of ¼ inch. A piece of printing and copying paper, twenty pound, of dimensions 8.5 inches×11 inches and 98 brightness is placed on top of the LEXAN PLEXIGLAS.
5. Place the stacked samples on top of each other on the PLEXIGLAS. Each stacked sample is separated by the copy paper as shown in FIG. 38.
6. A piece of the printing and copying paper, twenty pound, of dimensions 8.5 inches×11 inches and 98 brightness is then placed on the top sample and the resulting stack is topped with another piece of the LEXAN PLEXIGLAS as also shown in FIG. 38.
7. A 26-pound weight is placed on the top piece of PLEXIGLAS as also shown in FIG. 38. The entire structure is then placed in an aging chamber controlled at 40° C. and 75% relative humidity for five days.
8. After aging, each sample is then removed from the structure shown in FIG. 38. Each sample is then placed in a tensile tester equipped with a computerized data-acquisition system that is capable of calculating an average peel strength in grams force. The tensile tester is a Sintech Tensile Tester loaded with TESTWORKS software. In the TESTWORKS software, the 640-W peel method is used in which the jaw spacing is set to one inch.
9. Take the first sample and gently begin to separate the two tissue sheets along a top edge. Place one sheet of the sample in the lower jaw and the other sheet of the sample in the upper jaw of the tensile tester. When using creped tissue sheets, the creped side of the sample is visible and facing out.
10. Start the test to measure the blocking force. In particular, the tensile tester peels the two sheets apart. Peeling occurs along the length (machine direction) of the sample. The test is repeated for all five samples produced and the blocking force is measured and averaged for the five samples.

In this example, the uncreped through-air dried base webs were formed in a process similar to the process shown in FIG. 2. The base sheets had a basis weight of from 42.7 gsm to 44.5 gsm. The base sheet was made from 100% northern softwood kraft pulp.

As described above, after being formed, the base sheets were then subjected to a print creping process. The print creping process is generally illustrated in FIG. 8. The sheet was fed into a gravure printing line where a creping composition was printed onto the surface of the sheet similar to the process described in Example 2 above.

In a first set of samples, a conventional creping adhesive was applied to the base sheet. An additive composition made in accordance with the present disclosure was then added in different amounts to the conventional creping adhesive. Finally, samples were made containing only the additive composition made in accordance with the present disclosure.

The conventional creping adhesive used was AIRFLEX 426 binder obtained from Air Products, Inc. of Allentown, Pa.

AIRFLEX 426 is a flexible, non-crosslinking carboxylated vinyl acetate-ethylene terpolymer emulsion.

The additive composition made according to the present disclosure was as follows:

| Polymer (wt. ratios in parentheses) | Dispersing Agent | Dispersing Agent conc. (wt. %) |
|---|---|---|
| AFFINITY ™ EG8200/PRIMACOR ™ 5986i (60/40) | PRIMACOR ™ 5986i | 40.0 |

| Polymer Particle size (um) | Poly-dispersity | Solids (wt. %) | pH | Viscosity (cp) | Temp (° C.) | RPM | Spindle |
|---|---|---|---|---|---|---|---|
| 0.71 | 2.12 | 40.0 | 11.3 | 448 | 22.1 | 50 | RV3 |

The following samples were produced containing the conventional creping adhesive and the additive composition in the following percentages:

| Sample No. | % Conventional Creping Adhesive | % Additive Composition |
|---|---|---|
| 1 | 100 | 0 |
| 2 | 98 | 2 |
| 3 | 90 | 10 |
| 4 | 75 | 25 |
| 5 | 0 | 100 |

Figure 39:
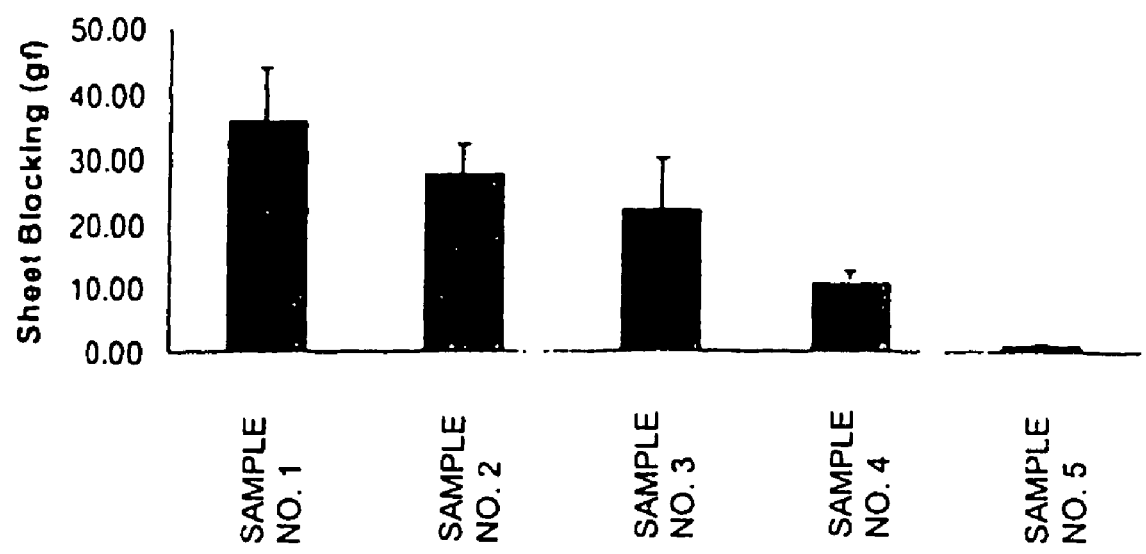
FIGS. 39, 40 and 41 are the results obtained in Example No. 6 below.

Sheet blocking was tested for each of the above samples according to the process described above. The blocking results are illustrated in FIG. 39. The samples were also tested for GMT, GMTEA, GMM/GMT and for wet/dry tensile in the cross direction. The following results were obtained.

| Sample No. | GMT(gf) | GMTEA (J/m2) | GMMod/GMT | Cross Direction W/D(%) |
|---|---|---|---|---|
| 1 | 1720 | 36.8 | 3.71 | 55 |
| Untreated | 1055 | 21.4 | 4.02 | 34 |
| 2 | 1061 | 22.3 | 3.83 | 33 |
| 3 | 1224 | 23.8 | 4.09 | 34 |
| 4 | 1416 | 25.8 | 4.84 | 30 |
| 5 | 2783 | 41.5 | 6.54 | 45 |

As shown in FIG. 39, sheet blocking drastically reduced as the amount of the additive composition increased in the creping composition. In fact, sheet blocking was substantially non-existent in Sample No. 5 that did not contain any of the conventional creping adhesive.

As shown in the above table, the additive composition according to the present disclosure also significantly increases the geometric mean tensile strength of the base sheet in comparison to the substantially identical but untreated sample. For instance, the geometric mean tensile strength more than doubled between the untreated sample and Sample No. 5 that contained only the additive composition.

In this regard, based on various factors, the geometric mean tensile strength of base sheets treated in accordance with the present disclosure may increase more than 10%, more than 25%, more than 50%, more than 75%, more than 100%, more than 125%, more than 150%, more than 175%, and even more than 200% in comparison to a substantially identical untreated sample.

As also shown from the above table, various other properties of the base sheet were improved when the base sheet was treated with the additive composition made in accordance with the present disclosure in comparison to the untreated sample.

In the next set of samples, various other additives were combined with the conventional creping adhesive. In particular, the conventional creping adhesive mixture in addition to the AIRFLEX 426 binder contained KYMENE 6500 available from Hercules, Incorporated. KYMENE 6500 is a wet strength agent. The conventional creping adhesive mixture also contained HERCOBOND available from Hercules, Incorporated, PROTOCOL CB2008 defoamer available from Hercules, Incorporated and sodium hydroxide.

| Chemistry | % of Composition |
|---|---|
| AIRFLEX 426 | 43.3 |
| Protocol CB2008 | 0.2 |
| Water | 32 |
| Kymene 6500 | 13.6 |
| Hercobond 1366 | 9.1 |
| NaOH (10%) | 1.8 |

The following samples were produced containing combinations of the conventional creping adhesive mixture and the additive composition made in accordance with the present disclosure:

| Sample No. | % Conventional Creping Adhesive Mixture | % Additive Composition |
|---|---|---|
| 6 | 100 | 0 |
| 7 | 97.5 | 2.5 |
| 8 | 95 | 5 |
| 9 | 25 | 75 |

The above samples produced the following results.

| Sample No. | GMT(gf) | GMTEA (J/m2) | GMMod/GMT | Cross Direction W/D(%) |
|---|---|---|---|---|
| 6 | 1720 | 36.8 | 3.71 | 55 |
| 7 | 1511 | 30.2 | 4.04 | 60 |

-continued

| Sample No. | GMT(gf) | GMTEA (J/m2) | GMMod/GMT | Cross Direction W/D(%) |
|---|---|---|---|---|
| 8 | 1478 | 31 | 4.16 | 53 |
| 9 | 2343 | 37.9 | 9.26 | 43 |

Figure 40:
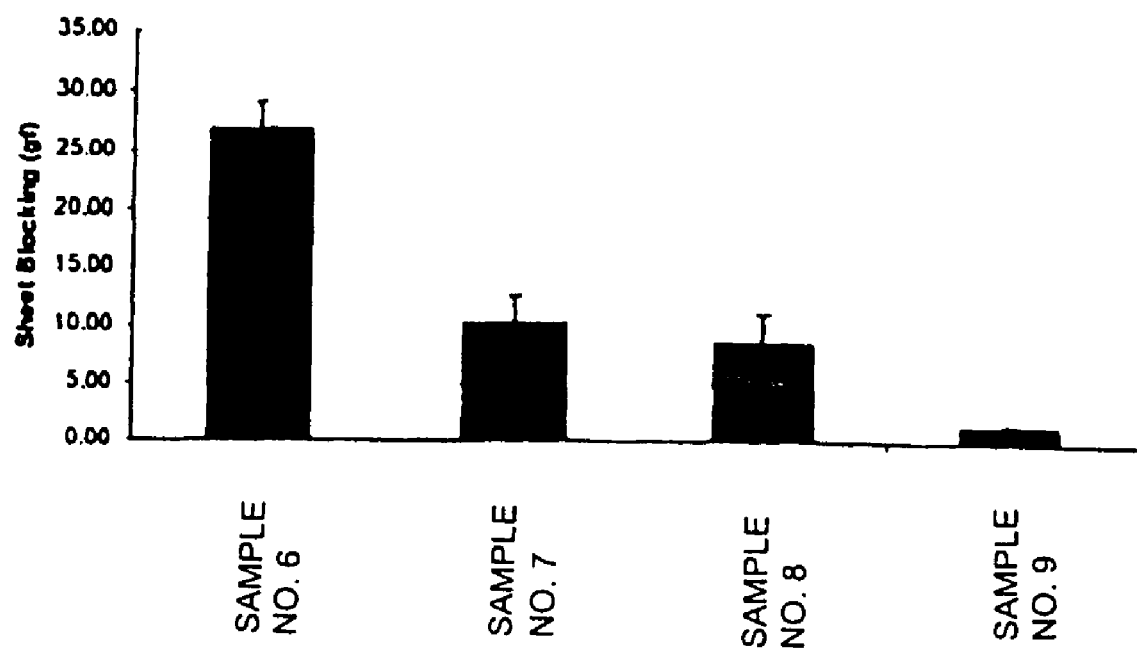

The blocking results are shown in FIG. 40. As shown, blocking dramatically decreases as greater amounts of the additive composition are contained in the creping adhesive.

It was noticed during these tests that the conventional creping mixture containing the KYMENE 6500 had a tendency to cause the additive composition to fall out of solution. As a result, further samples were made in which the conventional creping adhesive mixture did not contain the KYMENE 6500 product. In particular, the following samples were produced:

| Sample No. | % Conventional Creping Adhesive Mixture | % Additive Composition |
|---|---|---|
| 10 | 100 | 0 |
| 11 | 98 | 2 |
| 12 | 90 | 10 |
| 13 | 75 | 25 |
| 14 | 25 | 75 |
| 15 | 0 | 100 |

The above samples produced the following results.

| Sample No. | GMT(gf) | GMTEA (J/m2) | GMMod/GMT | Cross Direction W/D(%) |
|---|---|---|---|---|
| 10 | 2163 | 43.7 | 4.08 | 31 |
| 11 | 2197 | 43.4 | 3.95 | 30 |
| 12 | 1956 | 37 | 4.28 | 33 |
| 13 | 1642 | 31.5 | 4.88 | 32 |
| 14 | 2133 | 32.8 | 7.93 | 44 |
| 15 | 2783 | 41.5 | 6.54 | 45 |

Figure 41:
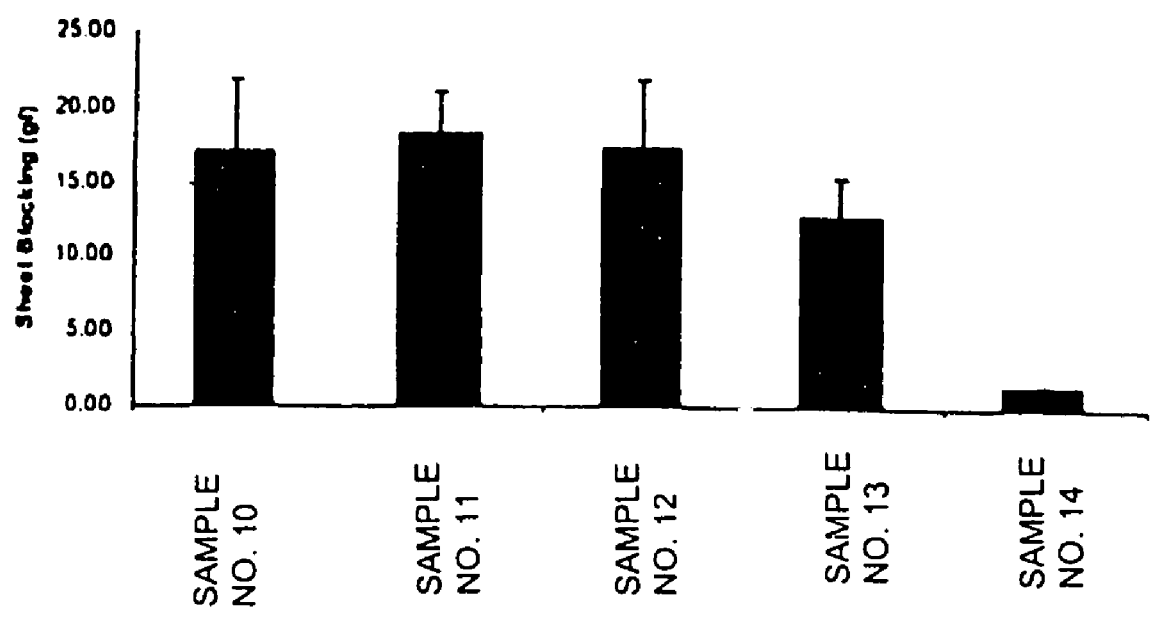

The blocking results are illustrated in FIG. 41. As shown, blocking reduced as greater amounts of the additive composition were present.

As shown above, sheet blocking can be less than 15 gf, such as less than 10 gf, such as even less than 5 gf when the creping adhesive contains the additive composition made according to the present disclosure.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A wiping product comprising:
   a sheet having a first side and a second side, wherein said sheet comprises from 0 to 49 percent by weight of cellulosic materials;
   a coating derived from an aqueous polyolefin dispersion, wherein said coating is present on at least the first side of the sheet, and wherein said coating has a thickness in the range of from 0.01 microns to 10 microns, and wherein said coating comprises an interconnected network with openings or said coating comprises discrete areas, and wherein said polyolefin dispersion comprises (a) a thermoplastic polymer comprising an alpha olefin interpolymer of ethylene or propylene and at least one comonomer, each comonomer being selected from the group consisting of octene, heptene, hexene, decene, and dodecene; (b) a dispersing agent, wherein said dispersing agent is a polar polymer; and (c) water, and wherein said aqueous polyolefin dispersion has an average particle size in the range of from 0.05 µ to 5 µm and a pH in a range of from 7 to 11, and wherein said dispersion comprises more than 25 percent by weight of water; and
   wherein the product has a wet/dry CD tensile of at least about 25% and, when stacked with an identical product, has a sheet blocking of less than 15 gf.

2. The wiping product of claim 1, wherein the wiping product has a bulk of less than 3 cc/g.

3. The wiping product of claim 1, wherein said sheet comprises a non-cellulosic material.

4. The wiping product of claim 1, wherein the first side of the tissue sheet has a stick slip of greater than about −0.01.

5. The wiping product of claim 1, wherein the product has a geometric mean tensile strength of at least 600 g/3 inches.

6. The wiping product of claim 1, wherein the sheet contains at least one base web that defines the first side and wherein the dispersion has been applied to the first side of the base web and the base web has been creped after the dispersion has been applied thereby forming said coating.

7. The wiping product of claim 1, wherein the sheet contains at least one base web that defines the first side and wherein the dispersion has been first applied to a creping surface and then the first side of the base web is contacted with the creping surface in order to apply the dispersion to the first side of the base web prior to creping the base web thereby forming said coating.

8. The wiping product of claim 6, wherein said dispersion has been applied to the first side of the base web according to a pattern and the base web has been creped after the dispersion has been applied thereby forming said coating.

9. The wiping product of claim 1, wherein the sheet contains a temporary wet strength agent.

10. The wiping product of claim 1, wherein the sheet contains a permanent wet strength agent.

11. The wiping product of claim 1, wherein the sheet has a dispersibility of less than about 2 minutes.

12. The wiping product of claim 1, wherein the sheet is comprised of only a single ply of a base web.

13. The wiping product of claim 1, wherein the sheet contains multiple plies.

14. The wiping product of claim 1, wherein the wiping product contains multiple, individual sheets that are in a stacked arrangement.

15. The wiping product of claim 1, wherein the wiping product contains multiple sheets spirally wound together, and each of the sheets is separated by a line of weakness.

16. The wiping product of claim 1, wherein the product has a HST value of less than about 100 seconds.

17. The wiping product of claim 1, wherein the product has a HST value of less than about 30 seconds.

18. The wiping product of claim 1, wherein the product is substantially dry.

19. The wiping product of claim 1, wherein the product contains less than 10% by weight moisture.

20. The wiping product of claim 1, wherein the presence of the coating derived from the aqueous dispersion increases the geometric mean tensile strength of the sheet by at least 10% in comparison to a substantially identical untreated sheet.

21. The wiping product of claim 1, wherein the presence of the coating derived from the aqueous dispersion increases the geometric mean tensile strength of the sheet by at least 25% in comparison to a substantially identical untreated sheet.

22. A wiping product comprising:

a base web, wherein said base web comprises from 0 to 49 percent by weight of cellulosic materials; and a coating derived from an aqueous polyolefin dispersion, wherein said coating is present on at least the first side of the sheet, wherein said coating has a thickness in the range of from 0.01 microns to 10 microns, and wherein said polyolefin dispersion comprises (a) a thermoplastic polymer comprising an alpha olefin interpolymer of ethylene or propylene and at least one comonomer, each comonomer being selected from the group consisting of octene, heptene, hexene, decene, and dodecene; (b) a dispersing agent comprising an ethylene-carboxylic acid copolymer; and water and wherein the wiping product when stacked with an identical product has a sheet blocking of less than about 15 gf.

* * * * *